US008637435B2

(12) United States Patent
Wang et al.

(10) Patent No.: US 8,637,435 B2
(45) Date of Patent: Jan. 28, 2014

(54) EUKARYOTIC CELL DISPLAY SYSTEMS

(75) Inventors: Kevin Caili Wang, Lansdale, PA (US); Peter Peizhi Luo, Lansdale, PA (US); Pingyu Zhong, Blue Bell, PA (US); Jian Wang, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 793 days.

(21) Appl. No.: 12/291,889

(22) Filed: Nov. 14, 2008

(65) Prior Publication Data
US 2009/0163379 A1  Jun. 25, 2009

Related U.S. Application Data

(60) Provisional application No. 61/003,413, filed on Nov. 16, 2007.

(51) Int. Cl.
  *C40B 40/02* (2006.01)
  *C40B 50/06* (2006.01)

(52) U.S. Cl.
  USPC .............................................. 506/26; 506/14

(58) Field of Classification Search
  None
  See application file for complete search history.

(56) References Cited

U.S. PATENT DOCUMENTS

| | | | |
|---|---|---|---|
| 4,816,567 A | 3/1989 | Cabilly et al. | |
| 4,888,281 A | 12/1989 | Schochetman et al. | |
| 5,037,750 A | 8/1991 | Schochetman et al. | |
| 5,700,678 A | 12/1997 | Toyoshima et al. | |
| 5,714,377 A | 2/1998 | Tanner et al. | |
| 5,733,757 A | 3/1998 | Barbas, III et al. | |
| 5,843,708 A | 12/1998 | Hardman et al. | |
| 5,874,247 A | 2/1999 | Toyoshima et al. | |
| 5,985,626 A | 11/1999 | Barbas, III et al. | |
| 6,114,147 A | 9/2000 | Frenken et al. | |
| 6,180,370 B1 | 1/2001 | Queen et al. | |
| 6,300,065 B1 | 10/2001 | Kieke et al. | |
| 6,368,839 B1 | 4/2002 | Barbas, III et al. | |
| 6,423,538 B1 | 7/2002 | Wittrup et al. | |
| 6,632,927 B2 | 10/2003 | Adair et al. | |
| 6,696,251 B1 | 2/2004 | Wittrup et al. | |
| 6,699,658 B1 | 3/2004 | Wittrup et al. | |

(Continued)

FOREIGN PATENT DOCUMENTS

| | | |
|---|---|---|
| EP | 1743938 | 1/2007 |
| WO | 9732017 | 9/1994 |

(Continued)

OTHER PUBLICATIONS

Holler, "In vitro evolution of a T cell receptor . . . ", PNAS (2000), vol. 97, pp. 5387-5392.

(Continued)

*Primary Examiner* — Ardin Marschel
*Assistant Examiner* — Christian Boesen
(74) *Attorney, Agent, or Firm* — Patricia L. Chisholm; Immac J. Thampoe

(57) ABSTRACT

The present invention provides expression vectors and helper display vectors which can be used in various combinations as vector sets for display of polypeptides on the outer surface of eukaryotic host cells. The expression vector of the invention can be used alone for soluble expression without having to change or reengineer the display vectors. The display systems of the invention are particularly useful for displaying a genetically diverse repertoire or library of polypeptides on the surface of yeast cells, and mammalian cells.

6 Claims, 24 Drawing Sheets

(56) References Cited

U.S. PATENT DOCUMENTS

| | | | |
|---|---|---|---|
| 6,833,441 | B2 | 12/2004 | Wang et al. |
| 6,872,392 | B2 | 3/2005 | Nakamura et al. |
| 6,919,183 | B2 | 7/2005 | Fandl et al. |
| 6,949,372 | B2 | 9/2005 | Betenbaugh et al. |
| 7,029,872 | B2 | 4/2006 | Gerngross |
| 7,105,554 | B2 | 9/2006 | Orchard et al. |
| 7,117,096 | B2 | 10/2006 | Luo et al. |
| 7,132,273 | B1 | 11/2006 | Choi et al. |
| 7,166,423 | B1 | 1/2007 | Miltenyi et al. |
| 7,175,983 | B2 * | 2/2007 | Wang et al. ............. 435/6.13 |
| 7,198,921 | B2 | 4/2007 | Miura et al. |
| 7,205,136 | B1 | 4/2007 | Schochetman et al. |
| 7,259,007 | B2 | 8/2007 | Bobrowicz et al. |
| 7,429,652 | B2 | 9/2008 | Wang et al. |
| 7,700,302 | B2 | 4/2010 | Hua et al. |
| 7,910,350 | B2 | 3/2011 | Wang et al. |
| 8,067,339 | B2 | 11/2011 | Prinz et al. |
| 2002/0068325 | A1 | 6/2002 | Ng et al. |
| 2003/0104355 | A1 * | 6/2003 | Wang et al. ............... 435/5 |
| 2003/0186374 | A1 * | 10/2003 | Hufton et al. ............. 435/69.1 |
| 2004/0018590 | A1 | 1/2004 | Gerngross et al. |
| 2004/0074458 | A1 | 4/2004 | Nakamura et al. |
| 2004/0219611 | A1 | 11/2004 | Racher |
| 2004/0230042 | A1 | 11/2004 | Hamilton |
| 2005/0142562 | A1 | 6/2005 | Zhu et al. |
| 2005/0170452 | A1 | 8/2005 | Wildt et al. |
| 2005/0191706 | A1 | 9/2005 | Zhao et al. |
| 2005/0196406 | A1 | 9/2005 | Daughtery et al. |
| 2005/0216958 | A1 | 9/2005 | Yamane et al. |
| 2005/0260729 | A1 | 11/2005 | Hamilton |
| 2006/0040353 | A1 | 2/2006 | Davidson et al. |
| 2006/0211085 | A1 | 9/2006 | Bobrowicz |
| 2007/0020260 | A1 | 1/2007 | Presta |
| 2007/0037248 | A1 | 2/2007 | Bobrowicz et al. |
| 2007/0072262 | A1 | 3/2007 | Nett et al. |
| 2007/0105199 | A1 | 5/2007 | Yan et al. |
| 2008/0032399 | A1 | 2/2008 | Harney et al. |
| 2009/0082221 | A1 * | 3/2009 | Wang et al. ............... 506/14 |
| 2010/0033192 | A1 | 2/2010 | Somfalvy |
| 2010/0075326 | A1 | 3/2010 | Jin et al. |
| 2010/0331192 | A1 | 12/2010 | Zha et al. |
| 2011/0009280 | A1 | 1/2011 | Hufton et al. |

FOREIGN PATENT DOCUMENTS

| | | |
|---|---|---|
| WO | 2004/057002 | 7/2004 |
| WO | 2007/061631 | 5/2007 |
| WO | WO 2007/130520 A2 * | 11/2007 |
| WO | 2008/006554 | 1/2008 |
| WO | 2009/105357 | 8/2009 |
| WO | 2009111183 | 11/2009 |
| WO | 2012074948 | 7/2012 |

OTHER PUBLICATIONS

Heyman, "Feedback regulaton by IgG antibodies", Immunol. Letters (2003). vol. 88, pp. 157-161.
Hamilton, "Humanization of yeast to produce complex terminally . . . ", Science (2006), vol. 313, pp. 1441-1443.
Hamilton, "Production of complex human glycoproteins . . . ", Science (2003), vol. 301, pp. 1244-1246.
Jacobs, "Pichia surface display: Display of proteins on the surface . . . ", Pichia Protein Expression Conference (2006), San Diego, CA, Abstract T23, pp. 1-9 and 37.
Huo, "Co-expression of human protein disulfide isomerase . . . ", Protein Exp. and Purif. (2007), vol. 54, pp. 234-239.
Inan, "Enhancement of protein secretion in Pichia pastoris . . . ", Biotech. and Bioeng. (2006), vol. 93, pp. 771-778.
Jabet, "NMR studies of the Pbx1 TALE homeodomain protein . . . ", J. Mol. Biol. (1999), vol. 291, pp. 521-530.
Jacobs, "Pichia surface display: Display of proteins on the surface . . . ", Biotech. Letters (2008), vol. 30, pp. 2173-2181.
Jordan, "G-protein-coupled receptor heterodimerization . . . ", Nature (1999), vol. 399, pp. 697-700.
Kammerer, "Heterodimerization of a functional GABA . . . ", Biochemistry (1999), vol. 38, pp. 13263-13269.
Kanda, "Comparison of biological activity among nonfucosylated . . . ", Glycobiology (2006), vol. 17, pp. 104-118.
Kanda, "Comparison of cell lines for stable production . . . ", Biotech. and Bioeng. (2006), vol. 94, pp. 680-688.
Keizer-Gunnink, "Accumulation of properly folded human type III . . . ", Matrix Biology (2000), vol. 19, pp. 29-36.
Kennard, "GPI-anchored fusion proteins", Methods in Biotech. (1999), vol. 8, pp. 187-200.
Kohler, "Continuous cultures of fused cells . . . ", Nature (1975), vol. 256, pp. 495-497.
Kuner, "Role of heteromer formation in GABA . . . ", Science (1999), vol. 283, pp. 74-77.
Ladner, "Constrained peptides as binding entities", Trends in Biotech. (1995), vol. 13, pp. 426-430.
Li, "Optimization of humanized IgGs in glycoengineered . . . ", Nature Biotech. (2006), vol. 24, pp. 210-215.
Lowman, "Selecting high-affinity binding proteins by monovalent . . . ", Biochemistry (1991), vol. 30, pp. 10832-10838.
Maras, "Filamentous fungi as production organisms . . . ", Glycoconjugate Journal (1999), vol. 16, pp. 99-107.
Markland, "Selection for protease inhibitors using bacteriophage . . . ", Methods in Enzymology (1996), vol. 267, pp. 28-51.
Marks, "Human antibodies from V-gene libraries . . . ", J. Mol. Biol. (1991), vol. 222, pp. 581-597.
Matthews, "Substrate phage: Selection of protease subtrates . . . ", Science (1993), vol. 260, pp. 1113-1117.
Mille, "Identification of a new family of genes involved in . . . ", J. Biol. Chem. (2008), vol. 283, pp. 9724-9736.
Nakabeppu, "DNA binding activities of three murine Jun proteins: . . . ", Cell (1988), vol. 55, pp. 907-915.
Nett, "Cloning and disruption of the PpURA5 gene and construction . . . ", Yeast (2003), vol. 20, pp. 1279-1290.
Nett, "Cloning and disruption of the Pichia pastoris ARG1 . . . ", Yeast (2005), vol. 22, pp. 295-304.
Phizicky, "Protein-protein interactions: Methods for detection . . . ", Microbiol. Rev. (1995), vol. 59, pp. 94-123.
Piper, "Structure of a HoxB1-Pbx1 heterodimer bound to DNA: . . . ", Cell (1999), vol. 96, pp. 587-597.
Rehberg, "Specific molecular activities of recombinant . . . ", J. Biol. Chem. (1982), vol. 257, pp. 11497-11502.
Ravetch, "Fc receptors", Curr. Opin. Immunol. (1997), vol. 9, pp. 121-125.
Riechmann, "Phage display and selection of a site-directed randomized . . . ", Biochemistry (1993), vol. 32, pp. 8848-8855.
Ren, "Display of adenoregulin with a novel Pichia pastoris . . . ", Molecular Biotech. (2007), vol. 35, pp. 103-108.
Roberts, "The biochemistry and genetics of capsular polysaccharide . . . ", Ann. Rev. Microbiol. (1996), vol. 50, pp. 285-315.
Sblattero, "Exploiting recombination in single bacteria . . . ", Nature Biotech. (2000), vol. 18, pp. 75-80.
Smeal, "Different requirements for formation of Jun: . . . ", Genes and Develop. (1989) vol. 3, pp. 2091-2100.
Boder, "Yeast surface display for screening combinatorial polypeptide libraries", Nature Biotech., (1997), vol. 15, pp. 553-557.
Lin, "A novel fragment of antigen binding (fab) surface display platform using glycoengineered Pichia pastoris", J. Immunol. Methods, (2012), vol. 375, pp. 159-165.
Weaver-Feldhaus, "Directed evolution for the development of confirmation-specific affinity reagents using yeast display", Protein Eng. Design and Selection, (2005), vol. 18, pp. 527-536.
Van De Vaart, "Comparison of cell wall proteins of Sacchromyces cerevisiae as anchors for cell surface expression of heterologous proteins", Applied and Environ. Microbio., (1997), vol. 63, pp. 615-620.
Krebber, "Co-selection of cognate antibody-antigen pairs by selectively infective phages", FEBS Letters (1995), vol. 377, pp. 227-231.
Crameri, "Cloning Aspergillus fumigatus allergens by the pJuFo filamentous phage display system", Int. Arch. of Allergy and Immunol., (1996), vol. 110, pp. 41-45.
Palzkill, "Mapping protein-ligand interactions using whole genome phage display libraries", Gene (1998) vol. 221, pp. 79-83.

(56) References Cited

OTHER PUBLICATIONS

Shimazu, "Cell surface display of organophosphorous hydrolase using ice nucleation protein", Biotech. Progress, (2001), vol. 17(1), pp. 76-80.
Zwick, "Homodimerice peptides displayed by the major coat protein of filamenous phage", J. Mol. Bio. (2000), vol. 300(2), pp. 307-320.
Slugg, "Baclofen inhibits guinea pig magnocellular neurones . . . ", J. Physiol. (2003), vol. 551.1, pp. 295-308.
Waterhouse, "Combinatorial infection and in vivo recombination: . . . ", Nucleic Acid Res., (1993), vol. 21, pp. 2265-2266.
Ryckaert, "Fishing for lectins for diverse sequence libraries: . . . ", Abstracts BVBMB Meeting (2005), 191st meeting of the Belgian Society of Biochemistry and Molecular Biology, Brussels, Belgium.
Abel, "Action of leucine zippers," Nature (1989), vol. 341, pp. 24-25.
Belshaw, "Controlling protein association and subcellular localization . . . ", PNAS (1996), vol. 93, pp. 4604-4607.
Berens, "Gene regulation by tetracylines", Eur. J. Biochem. (2003), vol. 270, pp. 3109-3121.
Bobrowicz, "Isolation of three contiguous genes . . . ", Yeast (1997), vol. 13, pp. 819-828.
Bobrowicz, "Engineering of an artificial glycosylation pathway . . . ", Glycobiology (2004), vol. 14, pp. 757-766.
Boder, "Directed evolution of antibody fragments with monovalent . . . ", PNAS (2000), vol. 97, pp. 10701-10705.
Frank, "A distinct seven-residue trigger sequence . . . ", J. Biol. Chem. (2000), vol. 275, pp. 11672-11677.
Caldas, "Design and synthesis of germline-based hemi-humanized . . . ", Protein Engineering (2000), vol. 13, pp. 353-360.
Songyang, "SI12 domains recognize specific phosphopeptide sequences", Cell (1993), vol. 72, pp. 767-778.
Chiba, "Production of human compatible high mannose-type . . . ", J. Biol. Chem. (1998), vol. 273, pp. 26298-26304.
Choi, "Use of combinatorial genetic libraries to humanize . . . ", PNAS (2003), vol. 100, pp. 5022-5027.
Choo, "Designing DNA-binding proteins on the surface . . . ", Curr. Opin. in Biotech. (1995), vol. 6, pp. 431-436.
Cohen, "The product of a fos-related gene, fra-1, binds cooperatively . . . ". Genes & Develop. (1989), vol. 3, pp. 173-184.
Cox, "Phagocytic signaling strategies: . . . ", Immunology (2001), vol. 13, pp. 339-345.
Daeron, "Fc receptor biology", Ann. Rev. Immunol. (1997), vol. 15, pp. 203-234.
Damasceno, "Cooverexpression of chaperones for enhanced secretion . . . ", Appl. Microbiol. Biotechnol. (2007), vol. 74, pp. 381-389.
Mergler, "Development of a bisphenol A-adsorbing yeast by surface display . . . ", Appl. Microbiol. Biotechnol. (2004), vol. 63, pp. 418-421.
Daugherty, "Quantitative analysis of the effect of the mutation . . . ", PNAS (2000), vol. 97, pp. 2029-2034.
De Groot, "Genome-wide identification of fungal GPI proteins", Yeast (2003), vol. 20, pp. 781-796.
DiRienzo, "The outer membrane proteins of gram-negative bacteria: . . . ", Ann. Rev. Biochem. (1978), vol. 47, pp. 481-532.
Ellman, "Combinatorial thinking in chemistry and biology", PNAS (1997), vol. 94, pp. 2779-2782.
Francisco, "Production and fluorescence-activated cell sorting . . . ", PNAS (1993), vol. 90, pp. 10444-10448.
Gentz, "Parallel association of Fos and Jun leucine zippers . . . ", Science (1989), vol. 243, pp. 1695-1699.
Geoffroy, "A new phage display system to construct multicombinatorial . . . ", Gene (1994), vol. 15, pp. 109-113.
Georgiou, "Display of heterologous proteins on the surface . . . ", Nature Biotech. (1997), vol. 15, pp. 29-34.
Gomes, "Heterodimerization of mu and beta opioid receptors: . . . ", J. of Neuroscience (2000), vol. 20, pp. 1-5.
Hoogenboom, "Designing and optimizing library selection strategies . . . ", Trends in Biotech. (1997), vol. 15, pp. 62-70.
Songyang, "A single point mutation switches the specificity . . . ", J. Biol. Chem. (1995), vol. 270, pp. 26029-26032.
Stemmer, "Rapid evolution of a protein in vitro by DNA shuffling", Nature (1994), vol. 370, pp. 389-391.
Stemmer, "DNA shuffling by random fragmentation and reassembly: . . . ", PNAS (1994), vol. 91, 10747-10751.
Streuli, "Target cell specificity of two species of human interferon-alpha . . . ", PNAS (1981), vol. 78, pp. 2848-2852.
Swers, "Shuffled antibody libraries created by in vivo homologous . . . ", Nucleic Acid Res. (2004), vol. 32, pp. 1-8.
Tanino, "Construction of a *Pichia pastoris* cell-surface display . . . ", Biotechnol. Prog. (2006), vol. 22, pp. 989-993.
Toman, "Production of recombinant human Type I procollagen . . . ", J. Biol. Chem. (2000), vol. 275, pp. 23303-23309.
Ulrich, "Expression studies of catalytic antibodies", PNAS (1995), vol. 92, pp. 11907-11911.
Vad, "Engineering of a *Pichia pastoris* expression system for secretion . . . ", J. of Biotech. (2005), vol. 116, pp. 251-260.
Walker, "Effect of redox environment on the in vitro and in vivo . . . ", J. Biol. Chem. (1994), vol. 269, pp. 28487-28493.
Wang, "Phage display of proteases and macromolecular inhibitors", Methods in Enzymology (1996), vol. 267, pp. 52-68.
Wang, "A new yeast display vector permitting free scFv amino . . . ", Protein Engineering, Design & Selection (2005), vol. 18, pp. 337-343.
White, "Heterodimerization is required for the formation . . . ", Nature (1998), vol. 396, pp. 679-682.
Wildt, "The humanization of N-glycosylation pathways in yeast", Nature Rev. (2005), p. 119-128.
Wolf, MultiCoil: A program for predicting two- and three-stranded coiled coils, Protein Science (1997), vol. 6, pp. 1179-1189.
Vvysocki, "The *Saccharomyces cerevisiae* ACR3 gene encodes . . . ", J. Biol. Chem. (1997), vol. 272, pp. 30061-30066.
Yamane-Ohnuki, "Establishment of FUT8 knockout Chinese hamster . . . ", Biotech. and Bioeng. (2004), vol. 87, pp. 614-622.
Zhang, "Enhanced secretion of heterologous proteins in *Pichia pastoris* . . . ", Biotech. Prog. (2006), vol. 22, pp. 1090-1095.
Ward, "The effector functions of immunoglobulins: . . . ", Therapeutic Immunol. (1995), vol. 2, p. 77-94.
Knappik, "Engineered turns of a recombinant antibody . . . ", Protein Engineering (1995), vol. 8, pp. 81-89.

\* cited by examiner

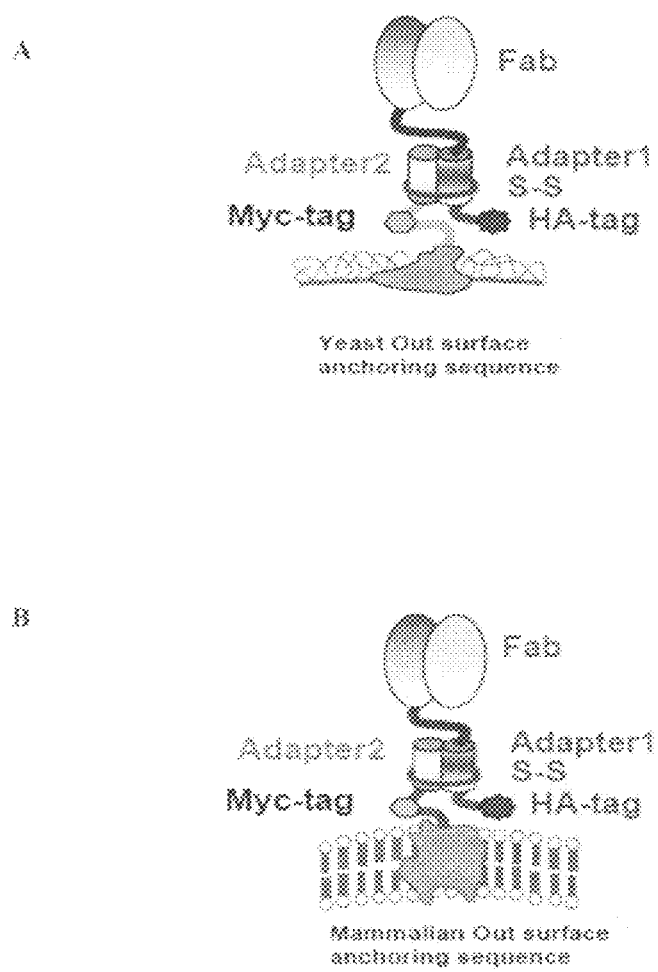

Anti-HA staining (adapter1, green)    Anti-Myc staining (adapter2, red)    Merged staining (green + red= yellow)

Figure 10

SEQ ID NO: 1 gaggagaagtcccggctgttggagaaggagaaccgtgaactggaaaagatcattgctgagaaagaggagcgtgtctctgaactgcgccatcaactcca
gtctgtaggaggttgt

SEQ ID NO: 2 acatcccgcttggaaggtttgcaatctgaaaaccacagattgagaatgaagattactgaattggacaaggacttggaagaagttactatgcaattgcaaga
cgttggtggttgt

SEQ ID NO: 10
EEKSRLLEKENRELEKIIAEKEERVSELRHQLQSVGGC

SEQ ID NO: 11
TSRLEGLSEQNHRLRMKITELDKDLEEVTMQLQDVGGC

Figure 11

SEQ. ID. NO 3 atgcggtttagtacgacactggcgacagcagcaacagcactttcttcacagcaagtcaggtaagcgcgagctccgaggtgcagctggtgcagagcgg
cggcggcgtggtgcagccgggcggcagcctgcgtctgagctgcgccgcgagcggctacaccttcaccaactacggcatgaactggattcgtcaggcc
cccgggaagggcctggagtgggtgggctggatcaacacctacaccggcgagccgacctacgcagctgacttcaagcgtcgtgtcaccttcagcctcg
acaccagcaagagcacggcgtacctgcaactgaacagcctgaggggccgaggacactgcagtttactactgcgcgaaataccgtactactacggtcgt
agccactggtacttcgacgtctggggccaagggacccttgtcaccgtctcgagcggcggtggcggttctggtggtggtggctctggtggcggcggatcc
gatatcgtgatgacccagagcccgagcaccctgagcgcgagtccgggtgagcgcgcgaccatcacctgcagtgcgagccagagcatcagcacctac
ctggcgtggtatcagcagaaaccaggtcaagcgccgcaagtgctgatctacgctgcgagcaacctggcgtccggagtgccgaaccgtttcagcggtag
ccgtagcgggaccgatttcaccctgaccatcagcagcttgcagccggaagacttcgcggtgtactactgccagcagtactacagcacccgtggacctt
cggtggtggtaccaaagtggaaatcaaagcggccgcttatccatacgacgtaccagactacgcaggaggtcatcaccatcatcaccatgtcgacggatc
tggaggaggtgaggagaagtcccggctgttggagaaggagaaccgtgaactggaaaagatcattgctgagaaagaggagcgtgtctctgaactgcgc
catcaactccagtctgtaggaggttgt

Figure 12A

SEQ. ID. NO 4 gacgtcaattcgcgttaaattttgttaaatcagctcattttttaaccaataggccgaaatccccaaaatcccttataaatcaaaagaatagaccgagatagg ttgagtgttgttccagtttggaacaagagtccactattaaagaacgtggactccaacgtcaaagggcgaaaaaccgtctatcagggcgatggcccactac gtgaaccatcaccctaatcaagttttttggggtcgaggtgccgtaaagcactaaatcggaaccctaaagggatgccccgatttagagcttgacggggaaa gccggcgaacgtggcgagaaaggaagggaagaaagcgaaaggagcgggcgctagggcgctggcaagtgtagcggtcacgctgcgcgtaaccacc acacccgccgcgcttaatgcgccgctacagggcgcgtttaattaaacggattagaagccgccgagcgggtgacagccctccgaaggaagactctcctc cgtgcgtcctcgtcttcaccggtcgcgttcctgaaacgcagatgtgcctcgcgccgcactgctccgaacaataaagattctacaatactagcttttatggtta tgaagaggaaaaattggcagtaacctggccccacaaaccttcaaatgaacgaatcaaattaacaaccataggatgataatgcgattagttttttagccttatt tctggggtaattaatcagcgaagcgatgattttgatctattaacagatatataaatgcaaaaactgcataaccactttaactaatactttcaacattttcggtttg tattacttcttattcaaatgtaataaaagtatcaacaaaaaattgttaatatacctctatactttaacgtcaaggagaaaaaacccggatcggactactagcct aggtaaacatgcggtttagtacgacactggcgacagcagcaacagcacttttcttcacagcaagtcaggtaagcgcgagctccgaggtgcagctggtgc agagcggcggcggcgtggtgcagccgggcggcagcctgcgtctgagctgcgccgcgagcggctacaccttcaccaactacggcatgaactggattc gtcaggcccccgggaagggcctggagtgggtgggctggatcaacacctacaccggcgagccgacctacgcagctgacttcaagcgtcgtgtcaccttt cagcctcgacaccagcaagagcacggcgtacctgcaactgaacagcctgagggccgaggacactgcagtttactactgcgcgaaataccgtactact acggtcgtagccactggtacttcgacgtctggggccaagggacccttgtcaccgtctcgagcggcggtggcggttctggtggtggtggctctggtggcg gcggatccgatatcgtgatgacccagagcccgagcaccctgagcgcgagtccgggtgagcgcgcgaccatcacctgcagtgcgagccagagcatca gcacctacctggcgtggtatcagcagaaaccaggtcaagcgccgcaagtgctgatctacgctgcgagcaacctggcgtccggagtgccgaaccgtttc agcggtagccgtagcgggaccgatttcacccctgaccatcagcagcttgcagccggaagacttcgcggtgtactactgccagcagtactacagcaccc gtggaccttcggtggtggtaccaaagtggaaatcaaagcggccgcttatccatacgacgtaccagactacgcaggaggtcatcaccatcatcaccatgt cgacggatctggaggaggtgaggagaagtcccggctgttggagaaggagaaccgtgaactggaaaagatcattgctgagaaagaggagcgtgtctct gaactgcgccatcaactccagtctgtaggaggttgttaataagtcgactaatgaccgcggatcatgtaattagttatgtcacgcttacattcacgccctcccc ccacatccgctctaaccgaaaaggaaggagttagacaacctgaagtctaggtccctattattttttatagttatgttagtattaagaacgttatttatatttcaa attttcttttttttctgtacagacgcgtgtacgcatgtaacattatactgaaaaccttgcttgagaaggttttgggacgctcgaaggctttaatttgcaagctgcg cgcgggtccttttcatcacgtgctataaaaataattataatttaaattttttaatataaatatataaattaaaaatagaaagtaaaaaaagaaattaaagaaaaaa tagtttttgttttccgaagatgtaaaagactctaggggggatcgccaacaaatactaccttttatcttgctcttcctgctctcaggtattaatgccgaattgtttcat cttgtctgtgtagaagaccacacacgaaaatcctgtgatttacattttacttatcgttaatcgaatgtatatctatttaatctgcttttcttgtctaataaatatatat gtaaagtacgcttttgttgaaattttttaaacctttgtttatttttttttcttcattccgtaactcttctacctttcttatttacttctaaaatccaaatacaaaacataaa aataaataaacacagagtaaattcccaaattattccatcattaaaagatacgaggcgcgtgtaagttacaggcaagcgatccgtcctaagaaaccattatta tcatgacattaacctataaaaataggcgtatcacgaggccctttcgtcttcaagaaattcggtcgaaaaaagaaaaggagagggccaagagggaggggca ttggtgactattgagcacgtgagtatacgtgattaagcacacaaaggcagcttggagtatgtctgttattaatttcacaggtagtctggtccattggtgaaag tttgcggcttgcagagcacagaggccgcagaatgtgctctagattccgatgctgacttgctgggtattatatgtgtgcccaatagaaagagaacaattgac ccggttattgcaaggaaaatttcaagtcttgtaaaagcatataaaaatagttcaggcactccgaaatacttggttggcgtgtttcgtaatcaacctaaggagg atgttttggctctggtcaatgattacggcattgatatcgtccaactgcacggagatgagtcgtggcaagaataccaagagttcctcggtttgccagttattaa aagactcgtatttccaaaagactgcaacatactactcagtgcagcttcacagaaacctcattcgtttattcccttgtttgattcagaagcaggtgggacaggt

Figure 12B gaacttttggattggaactcgatttctgactgggttggaaggcaagagagccccgagagcttacattttatgttagctggtggactgacgccagaaaatgtt
ggtgatgcgcttagattaaatggcgttattggtgttgatgtaagcggaggtgtggagacaaatggtgtaaaagactctaacaaaatagcaaatttcgtcaaa
aatgctaagaaataggttattactgagtagtatttatttaagtattgtttgtgcacttgccccgaatttcttatgatttatgatttttattattaaataagttataaaaaa
aataagtgtatacaaattttaaagtgactcttaggttttaaaacgaaaattcttattcttgagtaactctttcctgtaggtcaggttgctttctcaggtatagcatga
ggtcgctcacatgtgagcaaaaggccagcaaaaggccaggaaccgtaaaaaggccgcgttgctggcgttttttccataggctccgcccccctgacgagc
atcacaaaaatcgacgctcaagtcagaggtggcgaaacccgacaggactataaagataccaggcgtttccccctggaagctccctcgtgcgctctcctg
ttccgaccctgccgcttaccggatacctgtccgcctttctcccttcgggaagcgtggcgctttctcatagctcacgctgtaggtatctcagttcggtgtaggt
cgttcgctccaagctgggctgtgtgcacgaaccccccgttcagcccgaccgctgcgccttatccggtaactatcgtcttgagtccaacccggtaagacac
gacttatcgccactggcagcagccactggtaacaggattagcagagcgaggtatgtaggcggtgctacagagttcttgaagtggtggcctaactacggct
acactagaaggacagtatttggtatctgcgctctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgatcttttctacggggtctgacgctcagtggaac
gaaaactcacgttaagggattttggtcatgagattatcaaaaaggatcttcacctagatcctttaaattaaaaatgaagttttaaatcaatctaaagtatatatg
agtaaacttggtctgacagttaccaatgcttaatcagtgaggcacctatctcagcgatctgtctatttcgttcatccatagttgcctgactccccgtcgtgtaga
taactacgatacgggagggcttaccatctggccccagtgctgcaatgataccgcgagacccacgctcaccggctccagatttatcagcaataaaccagc
cagccggaagggccgagcgcagaagtggtcctgcaactttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagctccggttcccaacgatcaaggcgag
ttacatgatcccccatgttgtgcaaaaaagcggttagctccttcggtcctccgatcgttgtcagaagtaagttggccgcagtgttatcactcatggttatggca
gcactgcataattctcttactgtcatgccatccgtaagatgcttttctgtgactggtgagtactcaaccaagtcattctgagaatagtgtatgcggcgaccgag
ttgctcttgcccggcgtcaatacgggataataccgcgccacatagcagaactttaaaagtgctcatcattggaaaacgttcttcggggcgaaaactctcaa
ggatcttaccgctgttgagatccagttcgatgtaacccactcgtgcacccaactgatcttcagcatcttttactttcaccagcgtttctgggtgagcaaaaaca
ggaaggcaaaatgccgcaaaaaagggaataagggcgacacggaaatgttgaatactcatactcttcctttttcaatattattgaagcatttatcaggggttatt
gtctcatgagcggatacatatttgaatgtatttagaaaaataaacaatagggggttccgcgcacatttccccgaaaagtgccacct

Figure 13A
SEQ. ID. NO 5 gacgtccactcaaccctatctcggtctattcttttgatttataagggattttgccgatttcggcctattggttaaaaaatgagctgatttaacaaaaatttaacgc
gaattttaacaaaatattaacgtttacaatttcctgatgcggtatttctccttacgcatctgtgcggtatttcacaccgcatagggtaataactgatataattaaa
ttgaagctctaatttgtgagtttagtatacatgcatttacttataatacagttttttagttttgctggccgcatcttctcaaatatgcttcccagcctgcttttctgtaa
cgttcaccctctaccttagcatcccttcccttgcaaatagtcctcttccaacaataataatgtcagatcctgtagagaccacatcatccacggttctatactgtt
gacccaatgcgtctcccttgtcatctaaacccacaccgggtgtcataatcaaccaatcgtaaccttcatctcttccacccatgtctctttgagcaataaagcc
gataacaaaatctttgtcgctcttcgcaatgtcaacagtacccttagtatattctccagtagatagggagcccttgcatgacaattctgctaacatcaaaagg
cctctaggttcctttgttacttcttctgccgcctgcttcaaaccgctaacaatacctgggcccaccacaccgtgtgcattcgtaatgtctgcccattctgctatt
ctgtatacaccgcagagtactgcaatttgactgtattaccaatgtcagcaaattttctgtcttcgaagagtaaaaaattgtacttggcggataatgcctttagc
ggcttaactgtgccctccatggaaaaatcagtcaagatatccacatgagttttagtaaacaaattttgggacctaatgcttcaactaactccagtaattccttg
gtggtacgaacatccaatgaagcacacaagtttgtttgcttttcgtgcatgatattaaatagcttggcagcaacaggactaggatgagtagcagcacgttcc
ttatatgtagctttcgacatgatttatcttcgtttcctgcaggttttgttctgtgcagttgggttaagaatactgggcaatttcatgtttcttcaacactacatatgc
gtatatataccaatctaagtctgtgctccttccttcgttcttccttctgttcggagattaccgaatcaaaaaaattcaaagaaaccgaaatcaaaaaaaagaat
aaaaaaaaaatgatgaattgaattgaaaagctgtggtatggtgcactctcagtacaatctgctctgatgccgcatagttaagccagccccgacacccgcca
acaccgctgacgcgccctgacgggcttgtctgctcccggcatccgcttacagacaagctgtgaccgtctccgggagctgcatgtgtcagaggttttcac
cgtcatcaccgaaacgcgcgaggctagccccacacaccatagcttcaaaatgtttctactccttttttactcttccagatttctcggactccgcgcatcgcc
gtaccacttcaaaacacccaagcacagcatactaaattttccctctttcttcctctagggtgtcgttaattaccgtactaaaggtttggaaaagaaaaaaga
gaccgcctcgtttcttttcttcgtcgaaaaaggcaataaaaattttttatcacgtttcttttcttgaaatttttttttttagtttttttctctttcagtgacctccattgata
tttaagttaataaacggtcttcaatttctcaagtttcagtttcattttcttgttctattacaactttttttacttcttgttcattagaaagaaagcatagcaatctaatct
aaggggcggtgttgacaattaatcatcggcatagtatatcggcatagtataatacgacaaggtgaggaactaaaccatggccaagttgaccagtgccgtt
ccggtgctcaccgcgcgcgatgtcgccggagcggtcgagttctggaccgaccggctcgggttctcccgggacttcgtggaggacgacttcgccggtgt
ggtccgggacgacgtgaccctgttcatcagcgcgcgtccaggaccaggtggtgccggacaacaccctggcctgggtgtgggtgcgcggcctggacga
gctgtacgccgagtggtcggaggtcgtgtccacgaacttccgggacgcctccgggccggccatgaccgagatcggcgagcagccgtgggggcggg
agttcgccctgcgcgacccggccggcaactgcgtgcacttcgtggccgaggagcaggactgacacgtccgacggcggcccacgggtcccaggcctc
ggagatccgtcccctttccttgtcgatatcatgtaattagttatgtcacgcttacattcacgccctcccccacatccgctctaaccgaaaaggaaggag
ttagacaacctgaagtctaggtccctatttatttttatagttatgttagtattaagaacgttatttatatttcaaattttttttttttttctgtacagacgcgtgtacgc
atgtaacattatactgaaaaccttgcttgagaaggttttgggacgctcgaaggctttaatttgcaagctgaattcacggattagaagccgccgagcgggtga
cagccctccgaaggaagactctcctccgtgcgtcctcgtcttcaccggtcgcgttcctgaaacgcagatgtgcctcgcgccgcactgctccgaacaataa
agattctacaatactagcttttatggttatgaagaggaaaaattggcagtaacctggccccacaaaccttcaaatgaacgaatcaaattaacaaccatagga
tgataatgcgattagtttttagcctattctggggtaattaatcagcgaagcgatgatttttgatctattaacagatatataaatgcaaaaactgcataaccact
ttaactaatactttcaacattttcggtttgtattacttcttattcaaatgtaataaaagtatcaacaaaaaattgttaatatacctctatactttaacgtcaaggagaa
aaaaccccggatcggactactagcagctgtaatacgactcactatagggaatattaagctaattctacttcatacattttcaattaagtttaaaccatgacaat
gcctcatcgctatatgtttttggcagtctttacacttctggcactaactagtgtggcctcaggagccacttctagattggaaggtttgcaatctgaaaaccaca
gattgagaatgaagattactgaattggacaaggacttggaagaagttactatgcaattgcaagacgttggtggttgtgcggccgctgaacaaaagttgattt

Figure 13B ctgaagaagacttgagctccggtggtggttctggtggtggttccggttctggtggtggtggttccggtggtggttccggatcccaggaactgacaactatat
gcgagcaaatcccctcaccaactttagaatcgacgccgtactctttgtcaacgactactattttggccaacgggaaggcaatgcaaggagtttttgaatatt
acaaatcagtaacgtttgtcagtaattgcggttctcacccctcaacaactagcaaaggcagccccataaacacacagtatgttttttaagcttgttattactga
gtagtatttatttaagtattgtttgtgcacttgccccgaatttcttatgatttatgattttttattattaaataagttataaaaaaaataagtgtatacaaattttaaagtg
actcttaggttttaaaacgaaaattcttattcttgagtaactctttcctgtaggtcaggttgctttctcaggtatagcatgaggtcgctcacatgtgagcaaaagg
ccagcaaaaggccaggaaccgtaaaaaggccgcgttgctggcgttttccataggctccgcccccctgacgagcatcacaaaaatcgacgctcaagtc
agaggtggcgaaacccgacaggactataaagataccaggcgtttccccctggaagctccctcgtgcgctctcctgttccgaccctgccgcttaccggat
acctgtccgccttctcccttcgggaagcgtggcgctttctcatagctcacgctgtaggtatctcagttcggtgtaggtcgttcgctccaagctgggctgtgt
gcacgaaccccccgttcagcccgaccgctgcgccttatccggtaactatcgtcttgagtccaacccggtaagacacgacttatcgccactggcagcagc
cactggtaacaggattagcagagcgaggtatgtaggcggtgctacagagttcttgaagtggtggcctaactacggctacactagaaggacagtatttggt
atctgcgctctgctgaagccagttaccttcggaaaaagagttggtagctcttgatccggcaaacaaaccaccgctggtagcggtggtttttttgtttgcaagc
agcagattacgcgcagaaaaaaaggatctcaagaagatcctttgatctttctacggggtctgacgctcagtggaacgaaaactcacgttaagggattttg
gtcatgagattatcaaaaaggatcttcacctagatcctttaaattaaaaatgaagttttaaatcaatctaaagtatatatgagtaaacttggtctgacagttacc
aatgcttaatcagtgaggcacctatctcagcgatctgtctatttcgttcatccatagttgcctgactccccgtcgtgtagataactacgatacgggagggctta
ccatctggccccagtgctgcaatgataccgcgagacccacgctcaccggctccagatttatcagcaataaaccagccagccggaagggccgagcgca
gaagtggtcctgcaactttatccgcctccatccagtctattaattgttgccgggaagctagagtaagtagttcgccagttaatagtttgcgcaacgttgttgcc
attgctacaggcatcgtggtgtcacgctcgtcgtttggtatggcttcattcagctccggttcccaacgatcaaggcgagttacatgatcccccatgttgtgca
aaaaagcggttagctccttcggtcctccgatcgttgtcagaagtaagttggccgcagtgttatcactcatggttatggcagcactgcataattctcttactgtc
atgccatccgtaagatgcttttctgtgactggtgagtactcaaccaagtcattctgagaatagtgtatgcggcgaccgagttgctcttgcccggcgtcaatac
gggataataccgcgccacatagcagaactttaaaagtgctcatcattggaaaacgttcttcggggcgaaaactctcaaggatcttaccgctgttgagatcc
agttcgatgtaacccactcgtgcacccaactgatcttcagcatcttttactttcaccagcgtttctgggtgagcaaaaacaggaaggcaaaatgccgcaaa
aaagggaataagggcgacacggaaatgttgaatactcatactcttccttttcaatattattgaagcatttatcagggttattgtctcatgagcggatacatattt
gaatgtatttagaaaaataaacaataggggttccgcgcacatttccccgaaaagtgccacct

Figure 14A

SEQ. ID. NO 6 gacgtccactcaaccctatctcggtctattcttttgatttataagggattttgccgatttcggcctattggttaaaaaatgagctgatttaacaaaaatttaacgc
gaattttaacaaaatattaacgtttacaatttcctgatgcggtattttctccttacgcatctgtgcggtatttcacaccgcatagggtaataactgatataattaaa
ttgaagctctaatttgtgagtttagtatacatgcatttacttataatacagttttttagttttgctggccgcatcttctcaaatatgcttcccagcctgcttttctgtaa
cgttcaccctctaccttagcatcccttcccttgcaaatagtcctcttccaacaataataatgtcagatcctgtagagaccacatcatccacggttctatactgtt
gacccaatgcgtctcccttgtcatctaaacccacaccgggtgtcataatcaaccaatcgtaaccttcatctcttccacccatgtctctttgagcaataaagcc
gataacaaaatctttgtcgctcttcgcaatgtcaacagtacccttagtatattctccagtagataggggagcccttgcatgacaattctgctaacatcaaaagg
cctctaggttcctttgttacttcttctgccgcctgcttcaaaccgctaacaatacctgggcccaccacaccgtgtgcattcgtaatgtctgcccattctgctatt
ctgtatacacccgcagagtactgcaatttgactgtattaccaatgtcagcaaatttctgtcttcgaagagtaaaaaattgtacttggcggataatgcctttagc
ggcttaactgtgccctccatggaaaaatcagtcaagatatccacatgagtttttagtaaacaaattttgggacctaatgcttcaactaactccagtaattccttg
gtggtacgaacatccaatgaagcacacaagtttgtttgcttttcgtgcatgatattaaatagcttggcagcaacaggactaggatgagtagcagcacgttcc
ttatatgtagctttcgacatgatttatcttcgtttcctgcaggttttttgttctgtgcagttgggttaagaatactgggcaatttcatgtttcttcaacactacatatgc
gtatatataccaatctaagtctgtgctccttccttcgttcttccttctgttcggagattaccgaatcaaaaaaattcaaagaaaccgaaatcaaaaaaaagaat
aaaaaaaaaatgatgaattgaattgaaaagctgtggtatggtgcactctcagtacaatctgctctgatgccgcatagttaagccagccccgacacccgcca
acaccgctgacgcgccctgacgggcttgtctgctcccggcatccgcttacagacaagctgtgaccgtctccgggagctgcatgtgtcagaggttttcac
cgtcatcaccgaaacgcgcgaggctagccccacacaccatagcttcaaaatgtttctactccttttttactcttccagatttctcggactccgcgcatcgcc
gtaccacttcaaaacacccaagcacagcatactaaattttccctctttcttcctctagggtgtcgttaattacccgtactaaaggtttggaaaagaaaaaaga
gaccgcctcgtttcttttcttcgtcgaaaaaggcaataaaaattttatcacgtttctttttcttgaaatttttttttttagttttttttctctttcagtgacctccattgata
tttaagttaataaacggtcttcaatttctcaagtttcagtttcattttcttgttctattacaactttttttacttcttgttcattagaaagaaagcatagcaatctaatct
aaggggcggtgttgacaattaatcatcggcatagtatatcggcatagtataatacgacaaggtgaggaactaaaccatggccaagttgaccagtgccgtt
ccggtgctcaccgcgcgcgatgtcgccggagcggtcgagttctggaccgaccggctcggttctcccgggacttcgtggaggacgacttcgccggtgt
ggtccgggacgacgtgaccctgttcatcagcgcggtccaggaccaggtggtgccggacaacaccctggcctgggtgtgggtgcgcggcctggacga
gctgtacgccgagtggtcggaggtcgtgtccacgaacttccgggacgcctccgggccggccatgaccgagatcggcgagcagccgtgggggcggg
agttcgccctgcgcgacccggccggcaactgcgtgcacttcgtggccgaggagcaggactgacacgtccgacggcggcccacgggtcccaggcctc
ggagatccgtcccccttttccttgtcgatatcatgtaattagttatgtcacgcttacattcacgccctcccccacatccgctctaaccgaaaaggaaggag
ttagacaacctgaagtctaggtccctatttattttttatagttatgttagtattaagaacgttatttatatttcaaatttttcttttttttctgtacagacgcgtgtacgc
atgtaacattatactgaaaaccttgcttgagaaggttttgggacgctcgaaggctttaatttgcaagctgaattcacggattagaagccgccgagcgggtga
cagccctccgaaggaagactctcctccgtgcgtcctcgtcttcaccggtcgcgttcctgaaacgcagatgtgcctcgcgccgcactgctccgaacaataa
agattctacaatactagcttttatggttatgaagaggaaaaattggcagtaacctggccccacaaaccttcaaatgaacgaatcaaattaacaaccatagga
tgataatgcgattagttttttagccttatttctggggtaattaatcagcgaagcgatgattttgatctattaacagatatataaatgcaaaaactgcataaccact
ttaactaatactttcaacattttcggtttgtattacttcttattcaaatgtaataaaagtatcaacaaaaaattgttaatatacctctatactttaacgtcaaggagaa
aaaacccccggatcggactactagcagctgtaatacgactcactatagggaatattaagctaattctacttcatacatttttcaattaagtttaaaccatgacaat
gcctcatcgctatatgttttggcagtctttacacttctggcactaactagtgtggcctcaggagccacttctagattggaaggtttgcaatctgaaaaccaca
gattgagaatgaagattactgaattggacaaggacttggaagaagttactatgcaattgcaagacgttggtggttgtgcggccgctgaacaaaagttgattt

Figure 14B ctgaagaagacttgagctccggtggtggttctggtggtggttccggttctggtggtggtggttccggtggtggttccggatcctcaagtttgtcatcatcatct
tcaggacaaatcaccagctctatcacgtcttcgcgtccaattattacccattctatcctagcaatggaacttctgtgatttcttcctcagtaatttcttcctcagt
cacttcttctctattcacttcttctccagtcatttcttcctcagtcatttcttcttctacaacaacctccacttctatatttctgaatcatctaaatcatccgtcattcc
aaccagtagttccacctctggttcttctgagagcgaaacgagttcagctggttctgtctcttcttcctcttttatctcttctgaatcatcaaaatctcctacatattc
ttcttcatcattaccacttgttaccagtgcgacaacaagccaggaaactgcttcttcattaccacctgctaccactacaaaaacgagcgaacaaaccacttt
ggttaccgtgacatcctgcgagtctcatgtgtgcactgaatccatctccctgcgattgtttccacagctactgttactgttagcggcgtcacaacagagtat
accacatggtgccctatttctactacagagacaacaaagcaaaccaaagggacaacagagcaaaccacagaaacaacaaaacaaaccacggtagtta
caatttcttcttgtgaatctgacgtatgctctaagactgcttctccagccattgtatctacaagcactgctactattaacggcgttactacagaatacacaacat
ggtgtcctatttccaccacagaatcgaggcaacaaacaacgctagttactgttacttcctgcgaatctggtgtgtgttccgaaactgcttcacctgccattgtt
tcgacggccacggctactgtaatgatgttgttacggtctatcctacatggaggccacagactgcgaatgaagagtctgtcagctctaaaatgaacagtgc
taccggtgagacaacaaccaatactttagctgctgaaacgactaccaatactgtagctgctgagacgattaccaatactggagctgctgccatttctcaaat
cactgacggtcaaatccaagctactaccactgctaccaccgaagctaccaccactgctgccccatcttccaccgttgaaactgtttctccatccagcaccg
aaactatctctcaacaaactgaaaatggtgctgctaaggccgctgtcggtatgggtgccggtgctctagctgctgctgctatgttgttataagcttgttattact
gagtagtatttatttaagtattgtttgtgcacttgccccgaatttcttatgatttatgattttattattaaataagttataaaaaaaataagtgtatacaaattttaaag
tgactcttaggttttaaaacgaaaattcttattcttgagtaactctttcctgtaggtcaggttgctttctcaggtatagcatgaggtcgctcacatgtgagcaaaa
ggccagcaaaaggccaggaaccgtaaaaaggccgcgttgctggcgttttttccataggctccgcccccctgacgagcatcacaaaatcgacgctcaag
tcagaggtggcgaaacccgacaggactataaagataccaggcgtttccccctggaagctccctcgtgcgctctcctgttccgaccctgccgcttaccgg
ataccctgtccgcctttctcccttcgggaagcgtggcgctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaaggacagtatttg
gtatctgcgctctgctgaagccagttaccttcggaaaaagagttggtagctcttgatccggcaaacaaaccaccgctggtagcggtggtttttttgtttgcaa
gcagcagattacgcgcagaaaaaaaggatctcaagaagatcctttgatctttctacggggtctgacgctcagtggaacgaaaactcacgttaagggattt
tggtcatgagattatcaaaaaggatcttcacctagatccttttaaattaaaaatgaagtttaaatcaatctaaagtatatatgagtaaacttggtctgacagtta
ccaatgcttaatcagtgaggcacctatctcagcgatctgtctatttcgttcatccatagttgcctgactccccgtcgtgtagataactacgatacgggagggc
ttaccatctggccccagtgctgcaatgataccgcgagacccacgctcaccggctccagatttatcagcaataaaccagccagccggaagggccgagcg
cagaagtggtcctgcaactttatccgcctccatccagtctattaattgttgccgggaagctagagtaagtagttcgccagttaatagtttgcgcaacgttgttg
ccattgctacaggcatcgtggtgtcacgctcgtcgtttggtatggcttcattcagctccggttcccaacgatcaaggcgagttacatgatcccccatgttgtg
caaaaaagcggttagctccttcggtcctccgatcgttgtcagaagtaagttggccgcagtgttatcactcatggttatggcagcactgcataattctcttactg
tcatgccatccgtaagatgcttttctgtgactggtgagtactcaaccaagtcattctgagaatagtgtatgcggcgaccgagttgctcttgcccggcgtcaat
acgggataataccgcgccacatagcagaactttaaaagtgctcatcattggaaaacgttcttcggggcgaaaactctcaaggatcttaccgctgttgagat
ccagttcgatgtaacccactcgtgcacccaactgatcttcagcatcttttactttcaccagcgtttctgggtgagcaaaaacaggaaggcaaaatgccgca
aaaaagggaataagggcgacacggaaatgttgaatactcatactcttccttttcaatattattgaagcatttatcagggttattgtctcatgagcggatacata
tttgaatgtatttagaaaaataaacaatagggggttccgcgcacatttccccgaaaagtgccacct

Figure 15A

SEQ. ID. NO 7 gacgtcaattcgcgttaaattttgttaaatcagctcattttttaaccaataggccgaaatccccaaaatcccttataaatcaaaagaatagaccgagatagg ttgagtgttgttccagtttggaacaagagtccactattaaagaacgtggactccaacgtcaaagggcgaaaaaccgtctatcagggcgatggcccactac gtgaaccatcaccctaatcaagttttttggggtcgaggtgccgtaaagcactaaatcggaaccctaaagggatgccccgatttagagcttgacggggaaa gccggcgaacgtggcgagaaaggaagggaagaaagcgaaaggagcgggcgctagggcgctggcaagtgtagcggtcacgctgcgcgtaaccacc acaccgccgcgcttaatgcgccgctacagggcgcgtttaattaaacggattagaagccgccgagcgggtgacagccctccgaaggaagactctcctc cgtgcgtcctcgtcttcaccggtcgcgttcctgaaacgcagatgtgcctcgcgccgcactgctccgaacaataaagattctacaatactagcttttatggtta tgaagaggaaaaattggcagtaacctggccccacaaaccttcaaatgaacgaatcaaattaacaaccataggatgataatgcgattagttttttagccttatt tctggggtaattaatcagcgaagcgatgattttgatctattaacagatatataaatgcaaaaactgcataaccactttaactaatactttcaacattttcggtttg tattacttcttattcaaatgtaataaaagtatcaacaaaaaattgttaatatacctctatactttaacgtcaaggagaaaaaacccggatcggactactagcct aggtatgtagcgcaacgcaattaatgtgagttagctcactcattactaaccccaggctttacactttatgcttccagctcgtatgttgtgtggaattgtgagcg gataacaatttagtaaggagatctaaaaaatgcggtttagtacgacactggcgacagcagcaacagcactttcttcacagcaagtcaggtaagcgcgag ctccgaagtgcagctggtgcagagcggtgcggaagtgaaaaaccgggtgaaagcctgaaaatcagctgcaaaggttccggatacaccttcagccgct actgggttggctgggtgcgtcagatgcccgggaaaggtctggaatggatgggtgggatctatccgggtgacggttatacccactacaacccgaaattcc agggtcaggtgaccatctctgcagataaaagcatcagcaccgcgtacttgcagtggagcagcctgaaagctagcgataccgcgatgtactactgtgcgc gcttcccgaactggggtagcttcgattactggggccaaggcacccctggtgaccgtctcgagcgcaagcaccaaaggcccatcggtattccccctggca ccctcctccaagagcacctctgggggcacagcggccctgggctgcctggtcaaggactacttccccgagccggtgacggtgtcgtggaactcaggcg ctctgaccagcggcgtgcacaccttcccggctgtcctacagtcctcaggactctactccctcagcagcgtggtgactgtgccctccagcagcttgggcac ccagacctacatctgcaacgtgaatcacaagcccagcaacactaaggtggacaagaaagttgagcccaaatcttgtgacaaaactcacacagcggccg cttatccatacgacgtaccagactacgcaggaggtcatcaccatcatcaccatgtcgacggatctggaggaggtgaggagaagtcccggctgttggaga aggagaaccgtgaactggaaaagatcattgctgagaaagaggagcgtgtctctgaactgcgccatcaactccagtctgtaggaggttgttgagtcgacta ataggcctcgaatttcttatgatttatgatttttattattaaataagttataaaaaaaataagtgtatacaaattttaaagtgactcttaggttttaaaacgaaaattc ttattcttgagtaactctttcctgtaggtcaggttgctttctcaggtatagcatgaggtcgctcggcgcgccacggattagaagccgccgagcgggtgacag ccctccgaaggaagactctcctccgtgcgtcctcgtcttcaccggtcgcgttcctgaaacgcagatgtgcctcgcgccgcactgctccgaacaataaaga ttctacaatactagcttttatggttatgaagaggaaaaattggcagtaacctggccccacaaaccttcaaatgaacgaatcaaattaacaaccataggatga taatgcgattagttttttagccttatttctggggtaattaatcagcgaagcgatgattttgatctattaacagatatataaatgcaaaaactgcataaccactttta actaatactttcaacattttcggtttgtattacttcttattcaaatgtaataaaagtatcaacaaaaaattgttaatatacctctatactttaacgtcaaggagaaaa aaccctcagcgtatgtagcgcaacgcaattaatgtgagttagctcactcattactaaccccaggctttacactttatgcttccagctcgtatgttgtgtggaatt gtgagcggataacaatttagtaaggagatcgataaaatgcggtttagtacgacactggcgacagcagcaacagcactttcttcacagcaagtcaggtaa gcgctggatccgaaatcgtgctgacccagtctccgggcaccctgagcctgtcaccaggtgaacgtgcgaccctgtcttgcaaagcctctcagtctctttct cctacttacctgcactggtatcagcagaaaccgggtcaggcgccgcgtctgctgatctacggtgcgagcagccgtgcgaccggtatcccggaccgtttc agcgggtagcgggtagcggcaccgatttcaccctgaccatcagccgtctggaaccggaagacttcgcggtgtactactgccagcactacgagaccttcggt cagggtaccaaagtggagatcaaacgtacggtggctgcaccatctgtcttcatcttcccgccatctgatgagcagttgaaatctggaactgcctctgttgtg tgcctgctgaataacttctatcccagagaggccaaagtacagtggaaggtggataacgccctccaatcgggtaactccaggagagtgtcacagagcag

Figure 15B gacagcaaggacagcacctacagcctcagcagcaccctgacgctgagcaaagcagactacgagaaacacaaagtctacgcctgcgaagtcacccat
cagggcctgagttcgcccgtcacaaagagcttcaacaggggagagtgttaatgaccgcggatcatgtaattagttatgtcacgcttacattcacgccctcc
ccccacatccgctctaaccgaaaaggaaggagttagacaacctgaagtctaggtccctatttatttttttatagttatgttagtattaagaacgttatttatatttc
aaatttttctttttttctgtacagacgcgtgtacgcatgtaacattatactgaaaaccttgcttgagaaggttttgggacgctcgaaggctttaatttgcaagctg
cgcgcgggtccttttcatcacgtgctataaaaataattataattttaaattttttaatataaatatataaattaaaaatagaaagtaaaaaaagaaattaaagaaaa
aatagtttttgttttccgaagatgtaaaagactctaggggggatcgccaacaaatactacctttatcttgctcttcctgctctcaggtattaatgccgaattgtttc
atcttgtctgtgtagaagaccacacacgaaaatcctgtgattttacattttacttatcgttaatcgaatgtatatctatttaatctgcttttcttgtctaataaatatat
atgtaaagtacgcttttgttgaaatttttaaacctttgtttattttttttcttcattccgtaactcttctaccttctttatttactttctaaaatccaaatacaaaacata
aaaataaataaacacagagtaaattcccaaattattccatcattaaaagatacgaggcgcgtgtaagttacaggcaagcgatccgtcctaagaaaccatta
ttatcatgacattaacctataaaaataggcgtatcacgaggcccttcgtcttcaagaaattcggtcgaaaaagaaaaggagagggccaagagggagg
gcattggtgactattgagcacgtgagtatacgtgattaagcacacaaaggcagcttggagtatgtctgttattaatttcacaggtagttctggtccattggtga
aagtttgcggcttgcagagcacagaggccgcagaatgtgctctagattccgatgctgacttgctgggtattatatgtgtgcccaatagaaagagaacaatt
gacccggttattgcaaggaaaatttcaagtcttgtaaaagcatataaaaatagttcaggcactccgaaatacttggttggcgtgtttcgtaatcaacctaagg
aggatgttttggctctggtcaatgattacggcattgatatcgtccaactgcacggagatgagtcgtggcaagaataccaagagttcctcggtttgccagttat
taaaagactcgtatttccaaaagactgcaacatactactcagtgcagcttcacagaaacctcattcgtttattccctttgtttgattcagaagcaggtgggaca
ggtgaacttttggattggaactcgatttctgactgggttggaaggcaagagagccccgagagcttacattttatgttagctggtggactgacgccagaaaat
gttggtgatgcgcttagattaaatggcgttattggtgttgatgtaagcggaggtgtggagacaaatggtgtaaaagactctaacaaaatagcaaatttcgtca
aaaatgctaagaaataggttattactgagtagtatttatttaagtattgtttgtgcacttgccccgaatttcttatgatttatgattttattattaaataagttataaaa
aaaataagtgtatacaaattttaaagtgactcttaggttttaaaacgaaaattcttattcttgagtaactctttcctgtaggtcaggttgctttctcaggtatagcat
gaggtcgctcacatgtgagcaaaaggccagcaaaaggccaggaaccgtaaaaaggccgcgttgctggcgtttttccataggctccgcccccctgacga
gcatcacaaaaatcgacgctcaagtcagaggtggcgaaacccgacaggactataaagataccaggcgtttccccctggaagctccctcgtgcgctctcc
tgttccgaccctgccgcttaccggatacctgtccgcctttctcccttcggggaagcgtggcgctttctcatagctcacgctgtaggtatctcagttcggtgtag
gtcgttcgctccaagctgggctgtgtgcacgaaccccccgttcagcccgaccgctgcgccttatcggtaactatcgtcttgagtccaacccggtaagac
acgacttatcgccactggcagcagccactggtaacaggattagcagagcgaggtatgtaggcggtgctacagagttcttgaagtggtggcctaactacg
gctacactagaaggacagtatttggtatctgcgctctgctgaagccagttaccttcggaaaaagagttggtagctcttgatccggcaaacaaaccaccgct
ggtagcggtggtttttttgtttgcaagcagcagattacgcgcagaaaaaaaggatctcaagaagatcctttgatcttttctacggggtctgacgctcagtgga
acgaaaactcacgttaagggattttggtcatgagattatcaaaaaggatcttcacctagatccttttaaattaaaaatgaagttttaaatcaatctaaagtatata
tgagtaaacttggtctgacagttaccaatgcttaatcagtgaggcacctatctcagcgatctgtctatttcgttcatccatagttgcctgactccccgtcgtgta
gataactacgatacgggagggcttaccatctggccccagtgctgcaatgataccgcgagacccacgctcaccggctccagatttatcagcaataaacca
gccagccggaagggccgagcgcagaagtggtcctgcaactttatccgcctccatccagtctattaattgttgccgggaagctagagtaagtagttcgcca
gttaatagtttgcgcaacgttgttgccattgctacaggcatcgtggtgtcacgctcgtcgtttggtatggcttcattcagctccggttcccaacgatcaaggcg
agttacatgatccccatgttgtgcaaaaaagcggttagctccttcggtcctccgatcgttgtcagaagtaagttggccgcagtgttatcactcatggttatg
gcagcactgcataattctcttactgtcatgccatccgtaagatgcttttctgtgactggtgagtactcaaccaagtcattctgagaatagtgtatgcggcgacc
gagttgctcttgcccggcgtcaatacgggataataccgcgccacatagcagaactttaaaagtgctcatcattggaaaacgttcttcggggcgaaaactct
caaggatcttaccgctgttgagatccagttcgatgtaacccactcgtgcacccaactgatcttcagcatcttttactttcaccagcgtttctgggtgagcaaaa
acaggaaggcaaaatgccgcaaaaaagggaataagggcgacacggaaatgttgaatactcatactcttcctttttcaatattattgaagcatttatcagggt
tattgtctcatgagcggatacatatttgaatgtatttagaaaaataaacaaataggggttccgcgcacatttccccgaaaagtgccacct

Figure 16A
SEQ. ID. NO 8 tcgcgcgtttcggtgatgacggtgaaaacctctgacacatgcagctcccggagacggtcacagcttgtctgtaagcggatgccgggagcagacaagcc cgtcagggcgcgtcagcgggtgttggcgggtgtcggggctggcttaactatgcggcatcagagcagattgtactgagagtgcaccatatgcggtgtgaa ataccgcacagatgcgtaaggagaaaataccgcatcaggcgccattcgccattcaggctgcgcaactgttgggaagggcgatcggtgcgggcctcttc gctattacgccagctggcgaaaggggggatgtgctgcaaggcgattaagttgggtaacgccagggttttcccagtcacgacgttgtaaaacgacggccag tgaattcgcgttaaattttgttaaatcagctcattttttaaccaataggccgaaatcccaaaatccctataaatcaaaagaatagaccgagataggggttga gtgttgttccagtttggaacaagagtccactattaaagaacgtggactccaacgtcaaagggcgaaaaaccgtctatcagggcgatggcccactacgtga accatcaccctaatcaagttttttggggtcgaggtgccgtaaagcactaaatcggaaccctaaagggatgccccgatttagagcttgacggggaaagccg gcgaacgtggcgagaaaggaagggaagaaagcgaaaggagcgggcgctagggcgctggcaagtgtagcggtcacgctgcgcgtaaccaccacac ccgccgcgcttaatgcgccgctacagggcgcgtttaattaactctagttattaatagtaatcaattacggggtcattagttcatagcccatatatggagttccg cgttacataacttacggtaaatggcccgcctggctgaccgcccaacgaccccgcccattgacgtcaataatgacgtatgttcccatagtaacgccaata gggactttccattgacgtcaatggtggagtatttacggtaaactgcccacttggcagtacatcaagtgtatcatatgccaagtacgccccctattgacgtca atgacggtaaatggcccgcctggcattatgcccagtacatgaccttatgggactttcctacttggcagtacatctacgtattagtcatcgctattaccatgcat ggtcgaggtgagccccacgttctgcttcactctccccatctcccccccctcccaccccaattttgtatttatttattttttaattatttgtgcagcgatgggg gcggggggggggggggcgcgcgccaggcggggcggggcggggcgagggcggggcggggcgaggcggagaggtgcggcggcagccaa tcagagcggcgcgctccgaaagtttccttttatggcgaggcggcggcggcggcggccctataaaaagcgaagcgcgcggcgggcgggagtcgtgcg cgctgccttcgccccgtgcccgctccgccgccgcctcgcgccgcccgccccggctctgactgaccgcgttactcccacaggtgagcgggcgggac ggcccttctccttcgggctgtaattagcgcttggtttaatgacggcttgtttctttctgtggctgcgtgaaagccttgagggggctccggggagggcccttttgtg cggggggagcggctcggggctgtccgcggggggacggctgccttcggggggggacggggcaggggcggggttcggcttctggcgtgtgaccggcgg ctctagagcctctgctaaccatgttcatgccttcttcttttttcctacagctcctgggcaacgtgctggttattgtgctgtctcatcattttggcaaagaattggatc ggaccgaagcttgcgcaacgcaattaatgtgagttagctcactcattaggcaccccaggctttacactttatgcttccggctcgtatgttgtgtggaattgtg agcggataacaatttcacactaaggagggttttaaaccatggctacaggctcccggacgagtctgctcctggcttttggcctgctctgcctgccctggcttcaa gagggatccgcgagctccgaggtgcagctggtgcagagcggcggcggcgtggtgcagccgggcggcagcctgcgtctgagctgcgccgcgagcg gctacaccttcaccaactacggcatgaactggattcgtcaggcccccgggaagggcctggagtggggtgggctggatcaacacctacaccggcgagcc gacctacgcagctgacttcaagcgtcgtgtcaccttcagcctcgacaccagcaagagcacggcgtacctgcaactgaacagcctgagggccgaggac actgcagtttactactgcgcgaaataccccgtactactacggtcgtagccactggtacttcgacgtctggggccaagggaccccttgtcaccgtctcgagcg gcggtggcggttctggtggtggtggctctggtggcggcggatccgatatcgtgatgacccagagcccgagcaccctgagcgcgagtccgggtgagcg cgcgaccatcacctgcagtgcgagccagagcatcagcacctacctggcgtggtatcagcagaaaccaggtcaagcgccgcaagtgctgatctacgct gcgagcaacctggcgtccggagtgccgaaccgttcagcggtagccgtagcgggaccgatttcaccctgaccatcagcagcttgcagccggaagactt cgcggtgtactactgccagcagtactacagcaccccgtggaccttcggtggtggtaccaaagtggaaatcaaagcggccgcttatccatacgacgtacc agactacgcaggaggtcatcaccatcatcaccatgtcgacggatctggaggaggtgaggagaagtcccggctgttggagaaggagaaccgtgaactg gaaaagatcattgctgagaaagaggagcgtgtctctgaactgcgccatcaactccagtctgtaggaggttgttaataagtcgactaatgaagatctattaac ctcaggtgcaggctgcctatcagaaggtggtggctggtgtggccaatgccctggctcacaaataccactgagatcgatcttttttccctctgccaaaaattat ggggacatcatgaagccccttgagcatctgacttctggctaataaaggaaatttattttcattgcaatagtgtgttggaattttttgtgtctctcactcggaagg acatatgggagggcaaatcatttaaaacatcagaatgagttttggtttagagtttggcaacatatgcccatatgtaactagcataaccccttggggcctcta

Figure 16B aacgggtcttgaggggtttttgatatccagacatgataagatacattgatgagtttggacaaaccacaactagaatgcagtgaaaaaaatgctttatttgtga
aatttgtgatgctattgctttatttgtaaccattataagctgcaataaaacaagttggggtgggcgaagaactccagcatgagatccccgcgctggaggatcat
ccagccggcgtcccggaaaacgattccgaagcccaaccttttcatagaaggcggcggtggaatcgaaatctcgtgatggcaggttgggcgtcgcttggt
cggtcatttcgcgaaccccagagtcccgctcagaagaactcgtcaagaaggcgatagaaggcgatgcgctgcgaatcgggagcggcgataccgtaaa
gcacgaggaagcggtcagcccattcgccgccaagctcttcagcaatatcacgggtagccaacgctatgtcctgatagcggtccgccacacccagccgg
ccacagtcgatgaatccagaaaagcggccattttccaccatgatattcggcaagcaggcatcgccatgggtcacgacgagatcctcgccgtcgggcatg
cgcgccttgagcctggcgaacagttcggctggcgcgagccctgatgctcttcgtccagatcatcctgatcgacaagaccggcttccatccgagtacgtg
ctcgctcgatgcgatgtttcgcttggtggtcgaatgggcaggtagccggatcaagcgtatgcagccgccgcattgcatcagccatgatggatactttctcg
gcaggagcaaggtgagatgacaggagatcctgccccggcacttcgcccaatagcagccagtcccttcccgcttcagtgacaacgtcgagcacagctg
cgcaaggaacgcccgtcgtggccagccacgatagccgcgctgcctcgtcctgcagttcattcagggcaccggacaggtcggtcttgacaaaaagaac
cggggcgcccctgcgctgacagccggaacacggcggcatcagagcagccgattgtctgttgtgcccagtcatagccgaatagcctctccacccaagcg
gccggagaacctgcgtgcaatccatcttgttcaatcatgcgaaacgatcctcatcctgtctcttgatcagatccgaaaatggatatacaagctcccgggag
cttttttgcaaaagcctaggcctccaaaaaagcctcctcactacttctggaatagctcagaggcagaggcggcctcggcctctgcataaataaaaaaaatta
gtcagccatgggggcggagaatgggcggaactgggcggagttaggggcgggatgggcggagttaggggcgggactatggttgctgactaattgagatg
catgctttgcatacttctgcctgctggggagcctggggactttccacacctggttgctgactaattgagatgcatgctttgcatacttctgcctgcctgggga
gcctggggacttccacaccctaactgacacacattccacagacatgtgagcaaaaggccagcaaaaggccaggaaccgtaaaaaggccgcgttgct
ggcgtttttccataggctccgcccccctgacgagcatcacaaaaatcgacgctcaagtcagaggtggcgaaacccgacaggactataagataccagg
cgtttccccctggaagctccctcgtgcgctctcctgttccgaccctgccgcttaccggatacctgtccgcctttctcccttcgggaagcgtggcgctttctca
tagctcacgctgtaggtatctcagttcggtgtaggtcgttcgctccaagctgggctgtgtgcacgaaccccccgttcagcccgaccgctgcgccttatccg
gtaactatcgtcttgagtccaacccggtaagacacgacttatcgccactggcagcagccactggtaacaggattagcagagcgaggtatgtaggcggtg
ctacagagttcttgaagtggtggcctaactacggctacactagaaggacagtatttggtatctgcgctctgctgaagccagttaccttcggaaaaagagttg
gtagctcttgatccggcaaacaaaccaccgctggtagcggtggtttttttgtttgcaagcagcagattacgcgcagaaaaaaaggatctcaagaagatcct
ttgatcttttctacggggtctgacgctcagtggaacgaaaactcacgttaagggattttggtcatgagattatcaaaaaggatcttcacctagatccttttaaat
taaaaatgaagttttaaatcaatctaaagtatatatgagtaaacttggtctgacagttaccaatgcttaatcagtgaggcacctatctcagcgatctgtctatttc
gttcatccatagttgcctgactccccgtcgtgtagataactacgatacgggagggcttaccatctggccccagtgctgcaatgataccgcgagacccacg
ctcaccggctccagatttatcagcaataaaccagccagccggaagggccgagcgcagaagtggtcctgcaactttatccgcctccatccagtctattaatt
gttgccgggaagctagagtaagtagttcgccagttaatagtttgcgcaacgttgttgccattgctacaggcatcgtggtgtcacgctcgtcgtttggtatggc
ttcattcagctccggttcccaacgatcaaggcgagttacatgatccccatgttgtgcaaaaaagcggttagctccttcggtcctccgatcgttgtcagaagt
aagttggccgcagtgttatcactcatggttatggcagcactgcataattctcttactgtcatgccatccgtaagatgcttttctgtgactggtgagtactcaacc
aagtcattctgagaatagtgtatgcggcgaccgagttgctcttgcccggcgtcaatacgggataataccgcgccacatagcagaactttaaaagtgctcat
cattggaaaacgttcttcggggcgaaaactctcaaggatcttaccgctgttgagatccagttcgatgtaacccactcgtgcacccaactgatcttcagcatc
ttttactttcaccagcgtttctgggtgagcaaaaacaggaaggcaaaatgccgcaaaaaagggaataagggcgacacggaaatgttgaatactcatactc
ttccttttcaatattattgaagcatttatcaggttattgtctcatgagcggatacatatttgaatgtatttagaaaaataaacaaataggggttccgcgcacatt
tccccgaaaagtgccacctgacgtctaagaaaccattattatcatgacattaacctataaaaataggcgtatcacgaggccctttcgtc

Figure 17A

SEQ. ID. NO 9 tcgcgcgtttcggtgatgacggtgaaaacctctgacacatgcagctcccggagacggtcacagcttgtctgtaagcggatgccgggagcagacaagcc
cgtcagggcgcgtcagcgggtgttggcgggtgtcggggctggcttaactatgcggcatcagagcagattgtactgagagtgcaccatatgcggtgtgaa
ataccgcacagatgcgtaaggagaaaataccgcatcaggcgccattcgccattcaggctgcgcaactgttgggaagggcgatcggtgcgggcctcttc
gctattacgccagctggcgaaaggggggatgtgctgcaaggcgattaagttgggtaacgccagggttttcccagtcacgacgttgtaaaacgacggccag
tgaattcggatcgggagatctcccgatccctatggtcgactctcagtacaatctgctctgatgccgcatagttaagccagtatctgctccctgcttgtgtgtt
ggaggtcgctgagtagtgcgcgagcaaaatttaagctacaacaaggcaaggcttgaccgacaattgcatgaagaatctgcttagggttaggcgttttgcg
ctgcttcgcgatgtacgggccagatatacgcgttgacattgattattgactagttattaatagtaatcaattacggggtcattagttcatagcccatatatggag
ttccgcgttacataacttacggtaaatggcccgcctggctgaccgcccaacgaccccgcccattgacgtcaataatgacgtatgttcccatagtaacgcc
aatagggactttccattgacgtcaatgggtggactatttacggtaaactgcccacttggcagtacatcaagtgtatcatatgccaagtacgccccctattgac
gtcaatgacggtaaatggcccgcctggcattatgcccagtacatgaccttatgggactttcctacttggcagtacatctacgtattagtcatcgctattaccat
ggtgatgcggttttggcagtacatcaatgggcgtggatagcggtttgactcacggggatttccaagtctccaccccattgacgtcaatgggagtttgttttgg
caccaaaatcaacgggactttccaaaatgtcgtaacaactccgccccattgacgcaaatgggcggtaggcgtgtacggtgggaggtctatataagcaga
gctctctggctaactagagaacccactgcttactggcttatcgaaattaatacgactcactatagggagacccaagctggctagcaccatgcgaccctccg
ggacggccggggcagcgctcctggcgctgctggctgcgctctgcccggcgtctagagctaccagccgcctggagggcctgcagagcgagaaccac
cgcctgcgcatgaagatcaccgagctggacaaggacctggaggaggtgaccatgcagctgcaggacgtgggcggctgcgcggccgccgagcagaa
gctgatcagcgaggaggacctgaccggtggaggctccggaggaggtagcggatccggtacgaatgggcctaagatcccgtccatcgccactgggat
ggtgggggccctcctcttgctgctggtggtggccctggggatcggcctcttcatgcgaaggcgccacatcgttcggaagcgcacgctgcggaggctgct
gcaggagagggagcttgtggagcctcttacacccagttgataagcttgtttaaaccgctgatcagcctcgactgtgccttctagttgccagccatctgttgt
ttgcccctcccccgtgccttccttgaccctggaaggtgccactcccactgtcctttcctaataaaatgaggaaattgcatcgcattgtctgagtaggtgtcatt
ctattctggggggtggggtggggcaggacagcaaggggggaggattgggaagacaatagcaggcatgctggggatgcggtgggctctatggcttctga
ggcggaaagaaccagctggggctctaggggggtatccccggcgcgccaatttaacgcgaattaattctgtggaatgtgtgtcagttagggtgtggaaagtc
cccaggctccccagcaggcagaagtatgcaaagcatgcatctcaattagtcagcaaccaggtgtggaaagtcccccaggctccccagcaggcagaagt
atgcaaagcatgcatctcaattagtcagcaaccatagtcccgcccctaactccgcccatcccgcccctaactccgcccagttccgcccattctccgcccc
atggctgactaattttttttatttatgcagaggccgaggccgcctctgcctctgagctattccagaagtagtgaggaggcttttttggaggcctaggcttttgca
aaaagctcccgggagcttgtatatccatttttcggatctgatcagcacgtgttgacaattaatcatcggcatagtatatcggcatagtataatacgacaaggtg
aggaactaaaccatggccaagttgaccagtgccgttccggtgctcaccgcgcgcgacgtcgccggagcggtcgagttctggaccgaccggctcgggtt
ctcccgggacttcgtggaggacgacttcgccggtgtggtccgggacgacgtgaccctgttcatcagcgcggtccaggaccaggtggtgccggacaac
accctggcctgggtgtgggtgcgcggcctggacgagctgtacgccgagtggtcggaggtcgtgtccacgaacttccgggacgcctccgggccggcca
tgaccgagatcggcgagcagccgtgggggcgggagttcgccctgcgcgacccggccggcaactgcgtgcacttcgtggccgaggagcaggactga
cacgtgctacgagatttcgattccaccgccgccttctatgaaaggttgggcttcggaatcgttttccgggacgccggctggatgatcctccagcgcgggg
atctcatgctggagttcttcgcccaccccaacttgtttattgcagcttataatggttacaaataaagcaatagcatcacaaatttcacaaataaagcatttttttc
actgcattctagttgtggtttgtccaaactcatcaatgtatcttatcatgtctgtataccgtcgacctctagctagagcttggcgtaatcatggtcatagctgtttc
ctgtgtgaaattgttatccgctcacaattccacacaacatacgagccggaagcataaagtgtaaagcctggggtgcctaatgagtgagctaactcacatta
attgcgttgcgctcactgcccgctttccagtcgggaaacctgtcgtgccagctgcattaatgaatcggccaacgcgcggggagaggcggtttgcgtattg

Figure 17B ggcgctcttccgcttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctggcgtttttccataggc
tccgcccccctgacgagcatcacaaaaatcgacgctcaagtcagaggtggcgaaacccgacaggactataaagataccaggcgtttccccctggaag
ctccctcgtgcgctctcctgttccgaccctgccgcttaccggatacctgtccgcctttctcccttcgggaagcgtggcgctttctcatagctcacgctgtagg
tatctcagttcggtgtaggtcgttcgctccaagctgggctgtgtgcacgaaccccccgttcagcccgaccgctgcgccttatccggtaactatcgtcttgag
tccaacccggtaagacacgacttatcgccactggcagcagccactggtaacaggattagcagagcgaggtatgtaggcggtgctacagagttcttgaag
tggtggcctaactacggctacactagaaggacagtatttggtatctgcgctctgctgaagccagttaccttcggaaaaagagttggtagctcttgatccggc
aaacaaaccaccgctggtagcggtggtttttttgtttgcaagcagcagattacgcgcagaaaaaaaggatctcaagaagatcctttgatcttttctacggg
tctgacgctcagtggaacgaaaactcacgttaagggattttggtcatgagattatcaaaaaggatcttcacctagatccttttaaattaaaaatgaagttttaa
atcaatctaaagtatatatgagtaaacttggtctgacagttaccaatgcttaatcagtgaggcacctatctcagcgatctgtctatttcgttcatccatagttgcc
tgactccccgtcgtgtagataactacgatacgggagggcttaccatctggccccagtgctgcaatgataccgcgagacccacgctcaccggctccagat
ttatcagcaataaaccagccagccggaagggccgagcgcagaagtggtcctgcaactttatccgcctccatccagtctattaattgttgccgggaagcta
gagtaagtagttcgccagttaatagtttgcgcaacgttgttgccattgctacaggcatcgtggtgtcacgctcgtcgtttggtatggcttcattcagctccggtt
cccaacgatcaaggcgagttacatgatccccatgttgtgcaaaaaagcggttagctccttcggtcctccgatcgttgtcagaagtaagttggccgcagtg
ttatcactcatggttatggcagcactgcataattctcttactgtcatgccatccgtaagatgcttttctgtgactggtgagtactcaaccaagtcattctgagaat
agtgtatgcggcgaccgagttgctcttgcccggcgtcaatacgggataataccgcgccacatagcagaactttaaaagtgctcatcattggaaaacgttct
tcggggcgaaaactctcaaggatcttaccgctgttgagatccagttcgatgtaacccactcgtgcacccaactgatcttcagcatcttttactttcaccagcg
tttctgggtgagcaaaaacaggaaggcaaaatgccgcaaaaaagggaataagggcgacacggaaatgttgaatactcatactcttcctttttcaatattatt
gaagcatttatcagggttattgtctcatgagcggatacatatttgaatgtatttagaaaaataaacaaatagggggttccgcgcacatttccccgaaaagtgcc
acctgacgtctaagaaaccattattatcatgacattaacctataaaaataggcgtatcacgaggccctttcgtc

```
                       SEQUENCE LISTING

<160> NUMBER OF SEQ ID NOS: 11

<210> SEQ ID NO 1
<211> LENGTH: 114
<212> TYPE: DNA
<213> ORGANISM: Artificial Sequence
<220> FEATURE:
<223> OTHER INFORMATION: GABAB Receptor 1

<400> SEQUENCE: 1
gaggagaagt cccggctgtt ggagaaggag aaccgtgaac tggaaaagat cattgctgag      60
aaagaggagc gtgtctctga actgcgccat caactccagt ctgtaggagg ttgt           114

<210> SEQ ID NO 2
<211> LENGTH: 114
<212> TYPE: DNA
<213> ORGANISM: Artificial Sequence
<220> FEATURE:
<223> OTHER INFORMATION: GABAB 5 Receptor 2

<400> SEQUENCE: 2
acatcccgct tggaaggttt gcaatctgaa aaccacagat tgagaatgaa gattactgaa     60
ttggacaagg acttggaaga agttactatg caattgcaag acgttggtgg ttgt          114

<210> SEQ ID NO 3
<211> LENGTH: 1005
<212> TYPE: DNA
<213> ORGANISM: Artificial Sequence
<220> FEATURE:
<223> OTHER INFORMATION: Anti-VEGF scFv-GABAB  Receptor 1

<400> SEQUENCE: 3
atgcggttta gtacgacact ggcgacagca gcaacagcac tttctcttcac agcaagtcag     60 gtaagcgcga gctccgaggt gcagctggtg cagagcggcg gcggcgtggt gcagccgggc    120
ggcagcctgc gtctgagctg cgccgcgagc ggctacacct tcaccaacta cggcatgaac   180
tggattcgtc aggcccccgg gaagggcctg gagtgggtgg gctggatcaa cacctacacc   240
ggcgagccga cctacgcagc tgacttcaag cgtcgtgtca ccttcagcct cgacaccagc    300
```

```
aagagcacgg cgtacctgca actgaacagc ctgagggccg aggacactgc agtttactac      360
tgcgcgaaat acccgtacta ctacggtcgt agccactggt acttcgacgt ctggggccaa      420
gggacccttg tcaccgtctc gagcggcggt ggcggttctg gtggtggtgg ctctggtggc      480
ggcggatccg atatcgtgat gacccagagc ccgagcaccc tgagcgcgag tccgggtgag      540
cgcgcgacca tcacctgcag tgcgagccag agcatcagca cctacctggc gtggtatcag      600
cagaaaccag gtcaagcgcc gcaagtgctg atctacgctg cgagcaacct ggcgtccgga      660
gtgccgaacc gtttcagcgg tagccgtagc gggaccgatt tcaccctgac catcagcagc      720
ttgcagccgg aagacttcgc ggtgtactac tgccagcagt actacagcac cccgtggacc      780
ttcggtggtg gtaccaaagt ggaaatcaaa cgggccgctt atccatacga cgtaccagac      840
tacgcaggag gtcatcacca tcatcaccat gtcgacggat ctggaggagg tgaggagaag      900
tcccggctgt tggagaagga gaaccgtgaa ctggaaaaga tcattgctga gaaagaggag      960
cgtgtctctg aactgcgcca tcaactccag tctgtaggag gttgt                    1005
```

<210> SEQ ID NO 4
<211> LENGTH: 5602
<212> TYPE: DNA
<213> ORGANISM: Artificial Sequence
<220> FEATURE:
<223> OTHER INFORMATION: construction yeast expression vector pMAT12

<400> SEQUENCE: 4

```
gacgtcaatt cgcgttaaat ttttgttaaa tcagctcatt ttttaaccaa taggccgaaa       60
tccccaaaat cccttataaa tcaaaagaat agaccgagat agggttgagt gttgttccag      120 tttgaacaa gagtccacta ttaaagaacg tggactccaa cgtcaaaggg cgaaaaaccg      180
tctatcaggg cgatggccca ctacgtgaac catcacccta atcaagtttt tggggtcga      240 ggtgccgtaa agcactaaat cggaacccta aagggatgcc ccgatttaga gcttgacggg      300
gaaagccggc gaacgtggcg agaaaggaag ggaagaaagc gaaaggagcg ggcgctaggg      360
cgctggcaag tgtagcggtc acgctgcgcg taaccaccac acccgccgcg cttaatgcgc      420
cgctacaggg cgcgtttaat taaacggatt agaagccgcc gagcgggtga cagccctccg      480
aaggaagact ctcctccgtg cgtcctcgtc ttcaccggtc gcgttcctga aacgcagatg      540
tgcctcgcgc cgcactgctc cgaacaataa agattctaca atactagctt ttatggttat      600
gaagaggaaa aattggcagt aacctggccc cacaaacctt caaatgaacg aatcaaatta      660
acaaccatag gatgataatg cgattagttt tttagcctta tttctggggt aattaatcag      720
cgaagcgatg attttgatc tattaacaga tatataaatg caaaaactgc ataaccactt      780
taactaatac tttcaacatt ttcggtttgt attacttctt attcaaatgt aataaaagta      840
tcaacaaaaa attgttaata tacctctata ctttaacgtc aaggagaaaa accccggat      900 cggactacta gcctaggtaa acatgcggtt tagtacgaca ctggcgacag cagcaacagc      960
acttttcttc acagcaagtc aggtaagcgc gagctccgag gtgcagctgg tgcagagcgg     1020
cggcggcgtg gtgcagccgg gcggcagcct gcgtctgagc tgcgccgcga gcggctacac     1080
cttcaccaac tacggcatga actggattcg tcaggccccc gggaagggcc tggagtgggt     1140
gggctggatc aacacctaca ccggcgagcc gacctacgca gctgacttca gcgtcgtgt      1200 cacccttcagc ctcgacacca gcaagagcac ggcgtacctg caactgaaca gcctgagggc     1260
cgaggacact gcagtttact actgcgcgaa ataccgtac tactacggtc gtagccactg      1320
gtacttcgac gtctggggcc aagggaccct tgtcaccgtc tcgagcggcg gtggcggttc     1380
```

```
tggtggtggt ggctctggtg gcggcggatc cgatatcgtg atgacccaga gcccgagcac    1440
cctgagcgcg agtccgggtg agcgcgcgac catcacctgc agtgcgagcc agagcatcag    1500
cacctacctg gcgtggtatc agcagaaacc aggtcaagcg ccgcaagtgc tgatctacgc    1560
tgcgagcaac ctggcgtccg gagtgccgaa ccgtttcagc ggtagccgta gcgggaccga    1620 tttcacccctg accatcagca gcttgcagcc ggaagacttc gcggtgtact actgccagca    1680
gtactacagc accccgtgga ccttcggtgg tggtaccaaa gtggaaatca aagcggccgc    1740
ttatccatac gacgtaccag actacgcagg aggtcatcac catcatcacc atgtcgacgg    1800
atctggagga ggtgaggaga agtcccggct gttggagaag gagaaccgtg aactggaaaa    1860
gatcattgct gagaagagg agcgtgtctc tgaactgcgc catcaactcc agtctgtagg    1920
aggttgttaa taagtcgact aatgaccgcg gatcatgtaa ttagttatgt cacgcttaca    1980
ttcacgccct ccccccacat ccgctctaac cgaaaggaa ggagttagac aacctgaagt    2040
ctaggtccct atttattttt ttatagttat gttagtatta agaacgttat ttatatttca    2100 aattttctt tttttctgt acagacgcgt gtacgcatgt aacattatac tgaaaacctt    2160
gcttgagaag gttttgggac gctcgaaggc tttaatttgc aagctgcgcg cgggtccttt    2220
tcatcacgtg ctataaaaat aattataatt taaattttt aatataaata tataaattaa    2280
aaatagaaag taaaaaaga aattaaagaa aaaatagttt ttgttttccg aagatgtaaa    2340
agactctagg gggatcgcca acaaatacta cctttatct tgctcttcct gctctcaggt    2400
attaatgccg aattgtttca tcttgtctgt gtagaagacc acacgaaa atcctgtgat    2460 tttacatttt acttatcgtt aatcgaatgt atatctattt aatctgcttt tcttgtctaa    2520
taaatatata tgtaaagtac gcttttgtt gaaatttttt aaacctttgt ttatttttt    2580 ttcttcattc cgtaactctt ctaccttctt tatttacttt ctaaaatcca aatacaaaac    2640
ataaaaataa ataaacacag agtaaattcc caaattattc catcattaaa agatacgagg    2700
cgcgtgtaag ttacaggcaa gcgatccgtc ctaagaaacc attattatca tgacattaac    2760
ctataaaaat aggcgtatca cgaggcccctt tcgtcttcaa gaaattcggt cgaaaaaga    2820 aaggagagg gccaagaggg agggcattgg tgactattga gcacgtgagt atacgtgatt    2880
aagcacacaa aggcagcttg gagtatgtct gttattaatt tcacaggtag ttctggtcca    2940
ttggtgaaag tttgcggctt gcagagcaca gaggccgcag aatgtgctct agattccgat    3000
gctgacttgc tgggtattat atgtgtgccc aatagaaaga gaacaattga cccggttatt    3060
gcaaggaaaa tttcaagtct tgtaaaagca tataaaaata gttcaggcac tccgaaatac    3120
ttggttggcg tgtttcgtaa tcaacctaag gaggatgttt tggctctggt caatgattac    3180
ggcattgata tcgtccaact gcacggagat gagtcgtggc aagaatacca agagttcctc    3240
ggtttgccag ttattaaaag actcgtattt ccaaaagact gcaacatact actcagtgca    3300
gcttcacaga aacctcattc gtttattccc ttgtttgatt cagaagcagg tgggacaggt    3360
gaacttttgg attggaactc gatttctgac tgggttggaa ggcaagagag ccccgagagc    3420 ttacattta tgttagctgg tggactgacg ccagaaaatg ttggtgatgc gcttagatta    3480
aatggcgtta ttggtgttga tgtaagcgga ggtgtggaga caaatggtgt aaaagactct    3540
aacaaaatag caaatttcgt caaaaatgct aagaaatagg ttattactga gtagtattta    3600
tttaagtatt gtttgtgcac ttgccccgaa tttcttatga tttatgattt ttattattaa    3660
ataagttata aaaaaataa gtgtatacaa attttaaagt gactcttagg ttttaaaacg    3720
aaaattctta ttcttgagta actctttcct gtaggtcagg ttgctttctc aggtatagca    3780
```

```
tgaggtcgct cacatgtgag caaaaggcca gcaaaaggcc aggaaccgta aaaaggccgc    3840
gttgctggcg ttttttccata ggctccgccc ccctgacgag catcacaaaa atcgacgctc    3900
aagtcagagg tggcgaaacc cgacaggact ataaagatac caggcgtttc ccctggaag     3960 ctccctcgtg cgctctcctg ttccgaccct gccgcttacc ggatacctgt ccgcctttct    4020
cccttcggga agcgtggcgc tttctcatag ctcacgctgt aggtatctca gttcggtgta    4080
ggtcgttcgc tccaagctgg gctgtgtgca cgaaccccc gttcagcccg accgctgcgc    4140
cttatccggt aactatcgtc ttgagtccaa cccggtaaga cacgacttat cgccactggc    4200
agcagccact ggtaacagga ttagcagagc gaggtatgta ggcggtgcta cagagttctt    4260
gaagtggtgg cctaactacg gctacactag aaggacagta tttggtatct gcgctctgct    4320
gaagccagtt accttcggaa aaagagttgg tagctcttga tccggcaaac aaaccaccgc    4380
tggtagcggt ggtttttttg tttgcaagca gcagattacg cgcagaaaaa aaggatctca    4440
agaagatcct ttgatctttt ctacgggtc tgacgctcag tggaacgaaa actcacgtta    4500
agggattttg gtcatgagat tatcaaaaag gatcttcacc tagatccttt taaattaaaa    4560
atgaagtttt aaatcaatct aaagtatata tgagtaaact tggtctgaca gttaccaatg    4620
cttaatcagt gaggcaccta tctcagcgat ctgtctattt cgttcatcca tagttgcctg    4680
actccccgtc gtgtagataa ctacgatacg ggagggctta ccatctggcc ccagtgctgc    4740
aatgataccg cgagacccac gctcaccggc tccagattta tcagcaataa accagccagc    4800
cggaagggcc gagcgcagaa gtggtcctgc aactttatcc gcctccatcc agtctattaa    4860
ttgttgccgg gaagctagag taagtagttc gccagttaat agtttgcgca acgttgttgc    4920
cattgctaca ggcatcgtgg tgtcacgctc gtcgtttggt atggcttcat tcagctccgg    4980
ttcccaacga tcaaggcgag ttacatgatc ccccatgttg tgcaaaaaag cggttagctc    5040
cttcggtcct ccgatcgttg tcagaagtaa gttggccgca gtgttatcac tcatggttat    5100
ggcagcactg cataattctc ttactgtcat gccatccgta agatgctttt ctgtgactgg    5160
tgagtactca accaagtcat tctgagaata gtgtatgcgg cgaccgagtt gctcttgccc    5220
ggcgtcaata cgggataata ccgcgccaca tagcagaact ttaaaagtgc tcatcattgg    5280
aaaacgttct cggggcgaaa actctcaag gatcttaccg ctgttgagat ccagttcgat    5340
gtaacccact cgtgcaccca actgatcttc agcatctttt actttcacca gcgtttctgg    5400
gtgagcaaaa acaggaaggc aaaatgccgc aaaaaaggga ataagggcga cacggaaatg    5460
ttgaatactc atactcttcc ttttcaata ttattgaagc atttatcagg gttattgtct    5520
catgagcgga tacatatttg aatgtattta gaaaaataaa caaatagggg ttccgcgcac    5580
atttccccga aaagtgccac ct                                              5602
```

<210> SEQ ID NO 5
<211> LENGTH: 5749
<212> TYPE: DNA
<213> ORGANISM: Artificial Sequence
<220> FEATURE:
<223> OTHER INFORMATION: yeast helper vector pMAT7

<400> SEQUENCE: 5

```
gacgtccact caaccctatc tcggtctatt cttttgattt ataagggatt ttgccgattt      60
cggcctattg gttaaaaaat gagctgattt aacaaaaatt taacgcgaat tttaacaaaa    120
tattaacgtt tacaatttcc tgatgcggta ttttctcctt acgcatctgt gcggtatttc    180
acaccgcata gggtaataac tgatataatt aaattgaagc tctaatttgt gagtttagta    240
```

```
tacatgcatt tacttataat acagtttttt agttttgctg gccgcatctt ctcaaatatg    300
cttcccagcc tgcttttctg taacgttcac cctctacctt agcatccctt cccttttgcaa    360 atagtcctct tccaacaata taatgtcag atcctgtaga gaccacatca tccacggttc    420
tatactgttg acccaatgcg tctcccttgt catctaaacc cacaccgggt gtcataatca    480
accaatcgta accttcatct cttccaccca tgtctctttg agcaataaag ccgataacaa    540
aatctttgtc gctcttcgca atgtcaacag taccccttagt atattctcca gtagataggg    600
agcccttgca tgacaattct gctaacatca aaaggcctct aggttccttt gttacttctt    660
ctgccgcctg cttcaaaccg ctaacaatac ctgggcccac cacaccgtgt gcattcgtaa    720
tgtctgccca ttctgctatt ctgtatacac ccgcagagta ctgcaatttg actgtattac    780
caatgtcagc aaattttctg tcttcgaaga gtaaaaaatt gtacttggcg ataatgcct    840 ttagcggctt aactgtgccc tccatggaaa aatcagtcaa gatatccaca tgagttttta    900
gtaaacaaat tttgggacct aatgcttcaa ctaactccag taattccttg gtggtacgaa    960
catccaatga agcacacaag tttgtttgct tttcgtgcat gatattaaat agcttggcag    1020
caacaggact aggatgagta gcagcacgtt cctatatgt agctttcgac atgatttatc    1080
ttcgtttcct gcaggttttt gttctgtgca gttgggttaa gaatactggg caatttcatg    1140
tttcttcaac actacatatg cgtatatata ccaatctaag tctgtgctcc ttccttcgtt    1200
cttccttctg ttcggagatt accgaatcaa aaaatttca agaaaccga aatcaaaaaa    1260 aagaataaaa aaaaatgat gaattgaatt gaaaagctgt ggtatggtgc actctcagta    1320
caatctgctc tgatgccgca tagttaagcc agccccgaca cccgccaaca cccgctgacg    1380
cgccctgacg ggcttgtctg ctcccggcat ccgcttacag acaagctgtg accgtctccg    1440
ggagctgcat gtgtcagagg ttttcaccgt catcaccgaa acgcgcgagg ctagccccac    1500
acaccatagc ttcaaaatgt ttctactcct tttttactct tccagatttt ctcggactcc    1560
gcgcatcgcc gtaccacttc aaaacaccca agcacagcat actaaatttt ccctctttct    1620
tcctctaggt gtcgttaat tacccgtact aaaggtttgg aaaagaaaaa agagaccgcc    1680
tcgtttcttt ttcttcgtcg aaaaaggcaa taaaaatttt tatcacgttt ctttttcttg    1740 aaatttttt ttttagtttt tttctctttc agtgacctcc attgatattt aagttaataa    1800
acggtcttca atttctcaag tttcagtttc attttcttg ttctattaca acttttttta    1860
cttcttgttc attagaaaga aagcatagca atctaatcta aggggcggtg ttgacaatta    1920
atcatcggca tagtatatcg gcatagtata atacgacaag gtgaggaact aaaccatggc    1980
caagttgacc agtgccgttc cggtgctcac cgcgcgcgat gtcgccggag cggtcgagtt    2040
ctggaccgac cggctcgggt tctcccggga cttcgtggag gacgacttcg ccggtgtggt    2100
ccgggacgac gtgaccctgt tcatcagcgc ggtccaggac caggtggtgc cggacaacac    2160
cctggcctgg gtgtgggtgc gcggcctgga cgagctgtac gccgagtggt cggaggtcgt    2220
gtccacgaac ttccgggacg cctccggggcc ggccatgacc gagatcggcg agcagccgtg    2280
ggggcgggag ttcgccctgc gcgacccggc cggcaactgc gtgcacttcg tggccgagga    2340
gcaggactga cacgtccgac ggcggcccac gggtcccagg cctcggagat ccgtcccct    2400 tttccttgt cgatatcatg taattagtta tgtcacgctt acattcacgc cctccccca    2460 catccgctct aaccgaaaag gaaggagtta gacaacctga agtctaggtc cctatttatt    2520 ttttatagt tatgttagta ttaagaacgt tatttatatt tcaaattttt cttttttttc    2580
tgtacagacg cgtgtacgca tgtaacatta tactgaaaac cttgcttgag aaggttttgg    2640
```

```
gacgctcgaa ggctttaatt tgcaagctga attcacggat tagaagccgc cgagcgggtg   2700
acagccctcc gaaggaagac tctcctccgt gcgtcctcgt cttcaccggt cgcgttcctg   2760
aaacgcagat gtgcctcgcg ccgcactgct ccgaacaata aagattctac aatactagct   2820
tttatggtta tgaagaggaa aaattggcag taacctggcc ccacaaacct tcaaatgaac   2880
gaatcaaatt aacaaccata ggatgataat gcgattagtt ttttagcctt atttctgggg   2940
taattaatca gcgaagcgat gattttttgat ctattaacag atatataaat gcaaaaactg   3000
cataaccact ttaactaata cttttcaacat tttcggtttg tattacttct tattcaaatg   3060
taataaaagt atcaacaaaa aattgttaat atacctctat actttaacgt caaggagaaa   3120
aaaccccgga tcggactact agcagctgta atacgactca ctatagggaa tattaagcta   3180
attctacttc atacattttc aattaagttt aaaccatgac aatgcctcat cgctatatgt   3240
ttttggcagt cttacacttt ctggcactaa ctagtgtggc ctcaggagcc acttctagat   3300
tggaaggttt gcaatctgaa aaccacagat tgagaatgaa gattactgaa ttggacaagg   3360
acttggaaga agttactatg caattgcaag acgttggtgg ttgtgcggcc gctgaacaaa   3420
agttgatttc tgaagaagac ttgagctccg gtggtggttc tggtggtggt tccggttctg   3480
gtggtggtgg ttccggtggt ggttccggat cccaggaact gacaactata tgcgagcaaa   3540 tccctcacc aactttagaa tcgacgccgt actctttgtc aacgactact attttggcca   3600
acgggaaggc aatgcaagga gtttttgaat attacaaatc agtaacgttt gtcagtaatt   3660
gcggttctca cccctcaaca actagcaaag gcagccccat aaacacacag tatgtttttt   3720
aagcttgtta ttactgagta gtatttattt aagtattgtt tgtgcacttg ccccgaattt   3780
cttatgattt atgattttta ttattaaata agttataaaa aaaataagtg tatacaaatt   3840
ttaaagtgac tcttaggttt taaaacgaaa attcttattc ttgagtaact cttttcctgta   3900 ggtcaggttg ctttctcagg tatagcatga ggtcgctcac atgtgagcaa aaggccagca   3960
aaaggccagg aaccgtaaaa aggccgcgtt gctggcgttt ttccataggc tccgcccccc   4020
tgacgagcat cacaaaaatc gacgctcaag tcagaggtgg cgaaacccga caggactata   4080
aagataccag gcgtttcccc ctggaagctc cctcgtgcgc tctcctgttc cgaccctgcc   4140
gcttaccgga tacctgtccg cctttctccc ttcgggaagc gtggcgcttt ctcatagctc   4200
acgctgtagg tatctcagtt cggtgtaggt cgttcgctcc aagctgggct gtgtgcacga   4260
accccccgtt cagcccgacc gctgcgcctt atccggtaac tatcgtcttg agtccaaccc   4320
ggtaagacac gacttatcgc cactggcagc agccactggt aacaggatta gcagagcgag   4380
gtatgtaggc ggtgctacag agttcttgaa gtggtggcct aactacggct acactagaag   4440
gacagtattt ggtatctgcg ctctgctgaa gccagttacc ttcggaaaaa gagttggtag   4500
ctcttgatcc ggcaaacaaa ccaccgctgg tagcggtggt ttttttgttt gcaagcagca   4560
gattacgcgc agaaaaaaag gatctcaaga agatcctttg atcttttcta cggggtctga   4620
cgctcagtgg aacgaaaact cacgttaagg gattttggtc atgagattat caaaaaggat   4680
cttcacctag atccttttaa attaaaaatg aagttttaaa tcaatctaaa gtatatatga   4740
gtaaacttgg tctgacagtt accaatgctt aatcagtgag gcacctatct cagcgatctg   4800
tctatttcgt tcatccatag ttgcctgact ccccgtcgtg tagataacta cgatacggga   4860
gggcttacca tctggcccca gtgctgcaat gataccgcga acccacgct caccggctcc   4920 agatttatca gcaataaacc agccagccgg aaggccgag cgcagaagtg gtcctgcaac   4980
tttatccgcc tccatccagt ctattaattg ttgccgggaa gctagagtaa gtagttcgcc   5040
```

```
agttaatagt tgcgcaacg ttgttgccat tgctacaggc atcgtggtgt cacgctcgtc    5100
gtttggtatg gcttcattca gctccggttc ccaacgatca aggcgagtta catgatcccc    5160
catgttgtgc aaaaaagcgg ttagctcctt cggtcctccg atcgttgtca gaagtaagtt    5220
ggccgcagtg ttatcactca tggttatggc agcactgcat aattctctta ctgtcatgcc    5280
atccgtaaga tgcttttctg tgactggtga gtactcaacc aagtcattct gagaatagtg    5340
tatgcggcga ccgagttgct cttgcccggc gtcaatacgg gataataccg cgccacatag    5400
cagaacttta aaagtgctca tcattggaaa acgttcttcg gggcgaaaac tctcaaggat    5460
cttaccgctg ttgagatcca gttcgatgta acccactcgt gcacccaact gatcttcagc    5520
atcttttact tcaccagcg tttctgggtg agcaaaaaca ggaaggcaaa atgccgcaaa    5580
aaagggaata agggcgacac ggaaatgttg aatactcata ctcttccttt ttcaatatta    5640
ttgaagcatt tatcagggtt attgtctcat gagcggatac atatttgaat gtatttagaa    5700
aaataaacaa atagggggttc cgcgcacatt tccccgaaaa gtgccacct    5749

<210> SEQ ID NO 6
<211> LENGTH: 6793
<212> TYPE: DNA
<213> ORGANISM: Artificial Sequence
<220> FEATURE:
<223> OTHER INFORMATION: yeast helper vector pMAT8

<400> SEQUENCE: 6
gacgtccact caaccctatc tcggtctatt cttttgattt ataagggatt ttgccgattt      60
cggcctattg gttaaaaaat gagctgattt aacaaaaatt taacgcgaat tttaacaaaa     120
tattaacgtt tacaatttcc tgatgcggta ttttctcctt acgcatctgt gcggtatttc     180
acaccgcata gggtaataac tgatataatt aaattgaagc tctaatttgt gagtttagta     240
tacatgcatt tacttataat acagtttttt agttttgctg gccgcatctt ctcaaatatg     300
cttcccagcc tgcttttctg taacgttcac cctctacctt agcatccctt ccctttgcaa     360
atagtcctct tccaacaata ataatgtcag atcctgtaga gaccacatca tccacggttc     420
tatactgttg acccaatgcg tctcccttgt catctaaacc cacaccgggt gtcataatca     480
accaatcgta accttcatct cttccaccca tgtctctttg agcaataaag ccgataacaa     540
aatctttgtc gctcttcgca atgtcaacag tacccttagt atattctcca gtagataggg     600
agcccttgca tgacaattct gctaacatca aaaggcctct aggttccttt gttacttctt     660
ctgccgcctg cttcaaaccg ctaacaatac ctgggcccac cacaccgtgt gcattcgtaa     720
tgtctgccca ttctgctatt ctgtatacac ccgcagagta ctgcaatttg actgtattac     780
caatgtcagc aaattttctg tcttcgaaga gtaaaaaatt gtacttggcg ataatgcct     840 ttagcggctt aactgtgccc tccatggaaa aatcagtcaa gatatccaca tgagttttta     900
gtaaacaaat tttgggacct aatgcttcaa ctaactccag taattccttg gtggtacgaa     960
catccaatga agcacacaag tttgtttgct tttcgtgcat gatattaaat agcttggcag    1020
caacaggact aggatgagta gcagcacgtt ccttatatgt agctttcgac atgatttatc    1080
ttcgtttcct gcaggttttt gttctgtgca gttgggttaa gaatactggg caatttcatg    1140 ttcttcaac actacatatg cgtatatata ccaatctaag tctgtgctcc ttccttcgtt    1200
cttccttctg ttcggagatt accgaatcaa aaaatttca agaaaccga atcaaaaaa    1260 aagaataaaa aaaaatgat gaattgaatt gaaaagctgt ggtatggtgc actctcagta    1320
caatctgctc tgatgccgca tagttaagcc agccccgaca cccgccaaca cccgctgacg    1380
```

```
cgccctgacg ggcttgtctg ctcccggcat ccgcttacag acaagctgtg accgtctccg    1440
ggagctgcat gtgtcagagg ttttcaccgt catcaccgaa acgcgcgagg ctagccccac    1500
acaccatagc ttcaaaatgt ttctactcct tttttactct tccagatttt ctcggactcc    1560
gcgcatcgcc gtaccacttc aaaacaccca agcacagcat actaaatttt ccctctttct    1620
tcctctaggg tgtcgttaat tacccgtact aaaggtttgg aaaagaaaaa agagaccgcc    1680
tcgtttcttt ttcttcgtcg aaaaaggcaa taaaaatttt tatcacgttt cttttttcttg   1740 aaatttttt ttttagtttt tttctctttc agtgacctcc attgatattt aagttaataa     1800
acggtcttca atttctcaag tttcagtttc attttttcttg ttctattaca acttttttta   1860
cttcttgttc attagaaaga aagcatagca atctaatcta aggggcggtg ttgacaatta    1920
atcatcggca tagtatatcg gcatagtata atacgacaag gtgaggaact aaaccatggc    1980
caagttgacc agtgccgttc cggtgctcac cgcgcgcgat gtcgccggag cggtcgagtt    2040
ctggaccgac cggctcgggt tctcccggga cttcgtggag gacgacttcg ccggtgtggt    2100
ccgggacgac gtgaccctgt tcatcagcgc ggtccaggac caggtggtgc cggacaacac    2160
cctggcctgg gtgtgggtgc gcggcctgga cgagctgtac gccgagtggt cggaggtcgt    2220
gtccacgaac ttccgggacg cctccggggcc ggccatgacc gagatcggcg agcagccgtg   2280
ggggcgggag ttcgccctgc gcgacccggc cggcaactgc gtgcacttcg tggccgagga    2340
gcaggactga cacgtccgac ggcggcccac gggtcccagg cctcggagat ccgtccccct    2400
tttcctttgt cgatatcatg taattagtta tgtcacgctt acattcacgc cctccccca     2460 catccgctct aaccgaaaag gaaggagtta gacaacctga agtctaggtc cctatttatt    2520
tttttatagt tatgttagta ttaagaacgt tatttatatt tcaaattttt cttttttttc    2580
tgtacagacg cgtgtacgca tgtaacatta tactgaaaac cttgcttgag aaggttttgg    2640
gacgctcgaa ggctttaatt tgcaagctga attcacggat tagaagccgc cgagcgggtg    2700
acagccctcc gaaggaagac tctcctccgt gcgtcctcgt cttcaccggt cgcgttcctg    2760
aaacgcagat gtgcctcgcg ccgcactgct ccgaacaata aagattctac aatactagct    2820
tttatggtta tgaagaggaa aaattggcag taacctggcc ccacaaacct tcaaatgaac    2880
gaatcaaatt aacaaccata ggatgataat gcgattagtt ttttagcctt atttctgggg    2940
taattaatca gcgaagcgat gatttttgat ctattaacag atatataaat gcaaaaactg    3000
cataaccact ttaactaata ctttcaacat tttcggtttg tattacttct tattcaaatg    3060
taataaaagt atcaacaaaa aattgttaat atacctctat actttaacgt caaggagaaa    3120 aaacccccgga tcggactact agcagctgta atacgactca ctatagggaa tattaagcta   3180
attctacttc atacattttc aattaagttt aaaccatgac aatgcctcat cgctatatgt    3240
ttttggcagt ctttacactt ctggcactaa ctagtgtggc ctcaggagcc acttctagat    3300
tggaaggttt gcaatctgaa accacagat tgagaatgaa gattactgaa ttggacaagg     3360
acttggaaga agttactatg caattgcaag acgttggtgg ttgtgcggcc gctgaacaaa    3420
agttgatttc tgaagaagac ttgagctccg gtggtggttc tggtggtggt tccggttctg    3480
gtggtggtgg ttccggtggt ggttccggat cctcaagttt gtcatcatca tcttcaggac    3540
aaatcaccag ctctatcacg tcttcgcgtc caattattac cccattctat cctagcaatg    3600
gaacttctgt gatttcttcc tcagtaattt cttcctcagt cacttcttct ctattcactt    3660
cttctccagt catttcttcc tcagtcattt cttcttctac aacaacctcc acttctatat    3720
tttctgaatc atctaaatca tccgtcattc caaccagtag ttccacctct ggttcttctg    3780
```

```
agagcgaaac gagttcagct ggttctgtct cttcttcctc ttttatctct tctgaatcat    3840
caaaatctcc tacatattct tcttcatcat taccacttgt taccagtgcg acaacaagcc    3900
aggaaactgc ttcttcatta ccacctgcta ccactacaaa aacgagcgaa caaaccactt    3960
tggttaccgt gacatcctgc gagtctcatg tgtgcactga atccatctcc cctgcgattg    4020
tttccacagc tactgttact gttagcggcg tcacaacaga gtataccaca tggtgcccta    4080
tttctactac agagacaaca aagcaaacca aagggacaac agagcaaacc acagaaacaa    4140
caaaacaaac cacggtagtt acaatttctt cttgtgaatc tgacgtatgc tctaagactg    4200
cttctccagc cattgtatct acaagcactg ctactattaa cggcgttact acagaataca    4260
caacatggtg tcctatttcc accacagaat cgaggcaaca aacaacgcta gttactgtta    4320
cttcctgcga atctggtgtg tgttccgaaa ctgcttcacc tgccattgtt tcgacggcca    4380
cggctactgt gaatgatgtt gttacggtct atcctacatg gaggccacag actgcgaatg    4440
aagagtctgt cagctctaaa atgaacagtg ctaccggtga caacaacc aatactttag       4500 ctgctgaaac gactaccaat actgtagctg ctgagacgat taccaatact ggagctgctg    4560
ccatttctca aatcactgac ggtcaaatcc aagctactac cactgctacc accgaagcta    4620
ccaccactgc tgccccatct tccaccgttg aaactgtttc tccatccagc accgaaacta    4680
tctctcaaca aactgaaaat ggtgctgcta aggccgctgt cggtatgggt gccggtgctc    4740
tagctgctgc tgctatgttg ttataagctt gttattactg agtagtattt atttaagtat    4800
tgtttgtgca cttgccccga atttcttatg atttatgatt tttattatta aataagttat    4860
aaaaaaaata agtgtataca aattttaaag tgactcttag gttttaaaac gaaaattctt    4920
attcttgagt aactctttcc tgtaggtcag gttgctttct caggtatagc atgaggtcgc    4980
tcacatgtga gcaaaaggcc agcaaaaggc caggaaccgt aaaaaggccg cgttgctggc    5040 gttttccat aggctccgcc cccctgacga gcatcacaaa aatcgacgct caagtcagag       5100
gtggcgaaac ccgacaggac tataaagata ccaggcgttt ccccctggaa gctccctcgt    5160
gcgctctcct gttccgaccc tgccgcttac cggatacctg tccgcctttc tcccttcggg    5220
aagcgtggcg ctttctcata gctcacgctg taggtatctc agttcggtgt aggtcgttcg    5280
ctccaagctg ggctgtgtgc acgaaccccc cgttcagccc gaccgctgcg ccttatccgg    5340
taactatcgt cttgagtcca acccggtaag acacgactta tcgccactgg cagcagccac    5400
tggtaacagg attagcagag cgaggtatgt aggcggtgct acagagttct tgaagtggtg    5460
gcctaactac ggctacacta gaaggacagt atttggtatc tgcgctctgc tgaagccagt    5520
taccttcgga aaaagagttg gtagctcttg atccggcaaa caaaccaccg ctggtagcgg    5580 tggtttttt gtttgcaagc agcagattac gcgcagaaaa aaggatctc aagaagatcc       5640 tttgatcttt tctacggggt ctgacgctca gtggaacgaa aactcacgtt aagggatttt    5700
ggtcatgaga ttatcaaaaa ggatcttcac ctagatcctt ttaaattaaa aatgaagttt    5760
taaatcaatc taaagtatat atgagtaaac ttggtctgac agttaccaat gcttaatcag    5820
tgaggcacct atctcagcga tctgtctatt tcgttcatcc atagttgcct gactccccgt    5880
cgtgtagata actacgatac gggagggctt accatctggc cccagtgctg caatgatacc    5940
gcgagaccca cgctcaccgg ctccagattt atcagcaata accagccag ccggaagggc       6000 cgagcgcaga agtggtcctg caactttatc cgcctccatc cagtctatta attgttgccg    6060
ggaagctaga gtaagtagtt cgccagttaa tagtttcgc aacgttgttg ccattgctac       6120
aggcatcgtg gtgtcacgct cgtcgtttgg tatggcttca ttcagctccg gttcccaacg    6180
```

```
atcaaggcga gttacatgat cccccatgtt gtgcaaaaaa gcggttagct ccttcggtcc    6240
tccgatcgtt gtcagaagta agttggccgc agtgttatca ctcatggtta tggcagcact    6300
gcataattct cttactgtca tgccatccgt aagatgcttt tctgtgactg gtgagtactc    6360
aaccaagtca ttctgagaat agtgtatgcg gcgaccgagt tgctcttgcc cggcgtcaat    6420
acgggataat accgcgccac atagcagaac tttaaaagtg ctcatcattg gaaaacgttc    6480
ttcggggcga aaactctcaa ggatcttacc gctgttgaga tccagttcga tgtaacccac    6540
tcgtgcaccc aactgatctt cagcatcttt tactttcacc agcgtttctg ggtgagcaaa    6600
aacaggaagg caaaatgccg caaaaaaggg aataagggcg acacggaaat gttgaatact    6660
catactcttc cttttcaat attattgaag catttatcag ggttattgtc tcatgagcgg    6720
atacatattt gaatgtattt agaaaaataa acaaataggg gttccgcgca catttccccg    6780
aaaagtgcca cct                                                       6793
```

<210> SEQ ID NO 7
<211> LENGTH: 7146
<212> TYPE: DNA
<213> ORGANISM: Artificial Sequence
<220> FEATURE:
<223> OTHER INFORMATION: yeast expression vector pMAT19

<400> SEQUENCE: 7

```
gacgtcaatt cgcgttaaat ttttgttaaa tcagctcatt ttttaaccaa taggccgaaa      60
tccccaaaat cccttataaa tcaaaagaat agaccgagat agggttgagt gttgttccag     120
tttggaacaa gagtccacta ttaaagaacg tggactccaa cgtcaaaggg cgaaaaaccg     180
tctatcaggg cgatggccca ctacgtgaac catcacccta atcaagtttt ttggggtcga     240
ggtgccgtaa agcactaaat cggaacccta agggatgccc cgatttaga gcttgacggg     300 gaaagccggc gaacgtggcg agaaaggaag ggaagaaagc gaaggagcg ggcgctaggg     360 cgctggcaag tgtagcggtc acgctgcgcg taaccaccac acccgccgcg cttaatgcgc     420
cgctacaggc gcgtttaat taaacggatt agaagccgcc gagcgggtga cagccctccg     480
aaggaagact ctcctccgtg cgtcctcgtc ttcaccggtc gcgttcctga acgcagatg     540 tgcctcgcgc cgcactgctc cgaacaataa agattctaca atactagctt ttatggttat     600
gaagaggaaa aattggcagt aacctggccc cacaaacctt caaatgaacg aatcaaatta     660
acaaccatag gatgataatg cgattagttt tttagcctta tttctggggt aattaatcag     720
cgaagcgatg atttttgatc tattaacaga tatataaatg caaaaactgc ataaccactt     780
taactaatac tttcaacatt ttcggtttgt attacttctt attcaaatgt aataaaagta     840
tcaacaaaaa attgttaata tacctctata ctttaacgtc aaggagaaaa accccggat     900 cggactacta gctaggtat gtagcgcaac gcaattaatg tgagttagct cactcattac     960
taaccccagg ctttacactt tatgcttcca gctcgtatgt tgtgtggaat tgtgagcgga    1020
taacaattta gtaaggagat ctaaaaaatg cggtttagta cgacactggc gacagcagca    1080
acagcacttt tcttcacagc aagtcaggta agcgcgagct ccgaagtgca gctggtgcag    1140
agcggtgcgg aagtgaaaaa accgggtgaa agcctgaaaa tcagctgcaa aggttccgga    1200
tacaccttca gccgctactg ggttggctgg gtgcgtcaga tgcccgggaa aggtctggaa    1260
tggatgggtg ggatctatcc gggtgacggt tatacccact acaacccgaa attccagggt    1320
caggtgacca tctctgcaga taaaagcatc agcaccgcgt acttgcagtg gagcagcctg    1380
aaagctagcg ataccgcgat gtactactgt gcgcgcttcc cgaactgggg tagcttcgat    1440
```

```
tactggggcc aaggcaccct ggtgaccgtc tcgagcgcaa gcaccaaagg cccatcggta    1500 ttcccccctgg caccctcctc caagagcacc tctggggca cagcggccct gggctgcctg    1560
gtcaaggact acttccccga ccggtgacg gtgtcgtgga actcaggcgc tctgaccagc     1620
ggcgtgcaca ccttcccggc tgtcctacag tcctcaggac tctactccct cagcagcgtg   1680
gtgactgtgc cctccagcag cttgggcacc cagacctaca tctgcaacgt gaatcacaag   1740
cccagcaaca ctaaggtgga caagaaagtt gagcccaaat cttgtgacaa aactcacaca   1800
gcggccgctt atccatacga cgtaccagac tacgcaggag gtcatcacca tcatcaccat    1860
gtcgacggat ctggaggagg tgaggagaag tcccggctgt tggagaagga gaaccgtgaa   1920
ctggaaaaga tcattgctga gaagaggag cgtgtctctg aactgcgcca tcaactccag    1980
tctgtaggag gttgttgagt cgactaatag gcctcgaatt tcttatgatt tatgattttt    2040
attattaaat aagttataaa aaaataagt gtatacaaat tttaaagtga ctcttaggtt     2100
ttaaaacgaa aattcttatt cttgagtaac tctttcctgt aggtcaggtt gctttctcag    2160
gtatagcatg aggtcgctcg gcgcgccacg gattagaagc cgccgagcgg gtgacagccc   2220
tccgaaggaa gactctcctc cgtgcgtcct cgtcttcacc ggtcgcgttc ctgaaacgca    2280
gatgtgcctc gcgccgcact gctccgaaca ataaagattc tacaatacta gcttttatgg   2340
ttatgaagag gaaaaattgg cagtaacctg gccccacaaa ccttcaaatg aacgaatcaa   2400
attaacaacc ataggatgat aatgcgatta gttttttagc cttatttctg gggtaattaa    2460
tcagcgaagc gatgatttt gatctattaa cagatatata aatgcaaaaa ctgcataacc    2520
actttaacta atactttcaa cattttcggt ttgtattact tcttattcaa atgtaataaa    2580
agtatcaaca aaaaattgtt aatataccct tatactttaa cgtcaaggag aaaaaaccct   2640
cagcgtatgt agcgcaacgc aattaatgtg agttagctca ctcattacta accccaggct    2700 ttacactta tgcttccagc tcgtatgttg tgtggaattg tgagcggata caatttagt     2760 aaggagatcg ataaaatgcg gtttagtacg acactggcga cagcagcaac agcactttc    2820 ttcacagcaa gtcaggtaag cgctggatcc gaaatcgtgc tgacccagtc tccgggcacc   2880
ctgagcctgt caccaggtga acgtgcgacc ctgtcttgca aagcctctca gtctctttct   2940
cctacttacc tgcactggta tcagcagaaa ccgggtcagg cgccgcgtct gctgatctac   3000
ggtgcgagca gccgtgcgac cggtatcccg gaccgtttca gcggtagcgg tagcggcacc   3060
gatttcaccc tgaccatcag ccgtctggaa ccggaagact tcgcggtgta ctactgccag   3120
cactacgaga ccttcggtca gggtaccaaa gtggagatca aacgtacggt ggctgcacca   3180
tctgtcttca ttcttcccgcc atctgatgag cagttgaaat ctggaactgc tctgttgtg   3240 tgcctgctga ataacttcta tcccagagag gccaaagtac agtggaaggt ggataacgcc   3300
ctccaatcgg gtaactccca ggagagtgtc acagagcagg acagcaagga cagcacctac   3360
agcctcagca gcaccctgac gctgagcaaa gcagactacg agaaacacaa agtctacgcc   3420
tgcgaagtca cccatcaggg cctgagttcg cccgtcacaa agagcttcaa caggggagag    3480
tgttaatgac cgcggatcat gtaattagtt atgtcacgct tacattcacg ccctcccccc   3540
acatccgctc taaccgaaaa ggaaggagtt agacaacctg aagtctaggt ccctatttat    3600 tttttatag ttatgttagt attaagaacg ttatttatat ttcaaatttt tcttttttt     3660 ctgtacagac gcgtgtacgc atgtaacatt atactgaaaa ccttgcttga aaggttttg    3720 ggacgctcga aggctttaat ttgcaagctg cgcgcgggtc cttttcatca cgtgctataa   3780
aaataattat aatttaaatt ttttaatata aatatataaa ttaaaaatag aaagtaaaaa   3840
```

```
aagaaattaa agaaaaaata gtttttgttt tccgaagatg taaaagactc tagggggatc    3900
gccaacaaat actacctttt atcttgctct tcctgctctc aggtattaat gccgaattgt    3960
ttcatcttgt ctgtgtagaa gaccacacac gaaaatcctg tgattttaca ttttacttat    4020
cgttaatcga atgtatatct atttaatctg cttttcttgt ctaataaata tatatgtaaa    4080
gtacgctttt tgttgaaatt ttttaaacct ttgtttattt tttttcttc attccgtaac    4140

tcttctacct tctttattta ctttctaaaa tccaaataca aaacataaaa ataaataaac    4200
acagagtaaa ttcccaaatt attccatcat taaaagatac gaggcgcgtg taagttacag    4260
gcaagcgatc cgtcctaaga aaccattatt atcatgacat taacctataa aaataggcgt    4320
atcacgaggc cctttcgtct tcaagaaatt cggtcgaaaa aagaaaagga gagggccaag    4380
agggagggca ttggtgacta ttgagcacgt gagtatacgt gattaagcac acaaaggcag    4440
cttggagtat gtctgttatt aatttcacag gtagttctgg tccattggtg aaagtttgcg    4500
gcttgcagag cacagaggcc gcagaatgtg ctctagattc cgatgctgac ttgctgggta    4560

ttatatgtgt gcccaataga aagagaacaa ttgacccggt tattgcaagg aaaatttcaa    4620
gtcttgtaaa agcatataaa aatagttcag gcactccgaa atacttggtt ggcgtgtttc    4680
gtaatcaacc taaggaggat gttttggctc tggtcaatga ttacggcatt gatatcgtcc    4740
aactgcacga gatgagtcg tggcaagaat accaagagtt cctcggtttg ccagttatta    4800
aaagactcgt atttccaaaa gactgcaaca tactactcag tgcagcttca cagaaacctc    4860

atcgtttat tcccttgttt gattcagaag caggtgggac aggtgaactt ttggattgga    4920
actcgatttc tgactgggtt ggaaggcaag agagccccga gagcttacat tttatgttag    4980
ctggtggact gacgccagaa aatgttggtg atgcgcttag atTaaatggc gttattggtg    5040

ttgatgtaag cggaggtgtg gagacaaatg gtgtaaaaga ctctaacaaa atagcaaatt    5100

tcgtcaaaaa tgctaagaaa taggttatta ctgagtagta tttatttaag tattgtttgt    5160
gcacttgccc cgaatttctt atgatttatg аттттттатта ttaaataagt tataaaaaaa    5220

ataagtgtat acaaatttta aagtgactct taggttttaa aacgaaaatt cttattcttg    5280
agtaactctt tcctgtaggt caggttgctt tctcaggtat agcatgaggt cgctcacatg    5340

tgagcaaaag gccagcaaaa ggccaggaac cgtaaaaagg ccgcgttgct ggcgtttttc    5400
cataggctcc gcccccctga cgagcatcac aaaaatcgac gctcaagtca gaggtggcga    5460
aacccgacag gactataaag ataccaggcg tttccccctg gaagctccct cgtgcgctct    5520
cctgttccga ccctgccgct taccggatac ctgtccgcct ttctcccttc gggaagcgtg    5580
gcgctttctc atagctcacg ctgtaggtat ctcagttcgg tgtaggtcgt tcgctccaag    5640
ctgggctgtg tgcacgaacc ccccgttcag cccgaccgct gcgccttatc cggtaactat    5700
cgtcttgagt ccaacccggt aagacacgac ttatcgccac tggcagcagc cactggtaac    5760
aggattagca gagcgaggta tgtaggcggt gctacagagt tcttgaagtg gtggcctaac    5820

tacggctaca ctagaaggac agtatttggt atctgcgctc tgctgaagcc agttaccttc    5880
ggaaaaagag ttggtagctc ttgatccggc aaacaaacca ccgctggtag cggtggtttt    5940

tttgtttgca agcagcagat tacgcgcaga aaaaaggat ctcaagaaga tcctttgatc    6000

ttttctacgg ggtctgacgc tcagtggaac gaaaactcac gttaagggat tttggtcatg    6060
agattatcaa aaaggatctt cacctagatc cttttaaatt aaaaatgaag ttttaaatca    6120

atctaaagta tatatgagta aacttggtct gacagttacc aatgcttaat cagtgaggca    6180
cctatctcag cgatctgtct аттттcgттca tccatagttg cctgactccc cgtcgtgtag    6240
```

```
ataactacga tacgggaggg cttaccatct ggccccagtg ctgcaatgat accgcgagac      6300
ccacgctcac cggctccaga tttatcagca ataaaccagc cagccggaag ggccgagcgc      6360
agaagtggtc ctgcaacttt atccgcctcc atccagtcta ttaattgttg ccgggaagct      6420
agagtaagta gttcgccagt taatagtttg cgcaacgttg ttgccattgc tacaggcatc      6480
gtggtgtcac gctcgtcgtt tggtatggct tcattcagct ccggttccca acgatcaagg      6540
cgagttacat gatccccat gttgtgcaaa aaagcggtta gctccttcgg tcctccgatc      6600
gttgtcagaa gtaagttggc cgcagtgtta tcactcatgg ttatggcagc actgcataat      6660
tctcttactg tcatgccatc cgtaagatgc ttttctgtga ctggtgagta ctcaaccaag      6720
tcattctgag aatagtgtat gcggcgaccg agttgctctt gcccggcgtc aatacgggat      6780
aataccgcgc cacatagcag aactttaaaa gtgctcatca ttggaaaacg ttcttcgggg      6840
cgaaaactct caaggatctt accgctgttg agatccagtt cgatgtaacc cactcgtgca      6900
cccaactgat cttcagcatc ttttactttc accagcgttt ctgggtgagc aaaaacagga      6960
aggcaaaatg ccgcaaaaaa gggaataagg gcgacacgga aatgttgaat actcatactc      7020
ttcctttttc aatattattg aagcatttat cagggttatt gtctcatgag cggatacata      7080
tttgaatgta tttagaaaaa taaacaaata ggggttccgc gcacatttcc ccgaaaagtg      7140
ccacct                                                                7146
```

<210> SEQ ID NO 8
<211> LENGTH: 6804
<212> TYPE: DNA
<213> ORGANISM: Artificial Sequence
<220> FEATURE:
<223> OTHER INFORMATION: mammalian expression vector pMAG10

<400> SEQUENCE: 8

```
tcgcgcgttt cggtgatgac ggtgaaaacc tctgacacat gcagctcccg gagacggtca        60
cagcttgtct gtaagcggat gccggagca gacaagcccg tcagggcgcg tcagcgggtg         120
ttggcgggtg tcggggctgg cttaactatg cggcatcaga gcagattgta ctgagagtgc        180
accatatgcg gtgtgaaata ccgcacagat gcgtaaggag aaaataccgc atcaggcgcc        240
attcgccatt caggctgcgc aactgttggg aagggcgatc ggtgcgggcc tcttcgctat        300
tacgccagct ggcgaaaggg ggatgtgctg caaggcgatt aagttgggta acgccagggt        360
tttcccagtc acgacgttgt aaaacgacgg ccagtgaatt cgcgttaaat ttttgttaaa        420
tcagctcatt ttttaaccaa taggccgaaa tccccaaaat cccttataaa tcaaaagaat        480
agaccgagat agggttgagt gttgttccag tttggaacaa gagtccacta ttaaagaacg        540
tggactccaa cgtcaaaggg cgaaaaaccg tctatcaggg cgatggccca ctacgtgaac        600
catcacccta atcaagtttt tggggtcga ggtgccgtaa agcactaaat cggaaccta         660 aagggatgcc ccgatttaga gcttgacggg gaaagccggc gaacgtggcg agaaaggaag        720
ggaagaaagc gaaaggagcg ggcgctaggg cgctggcaag tgtagcggtc acgctgcgcg        780
taaccaccac acccgccgcg cttaatgcgc cgctacaggg cgcgtttaat taactctagt        840
tattaatagt aatcaattac ggggtcatta gttcatagcc catatatgga gttccgcgtt        900
acataactta cggtaaatgg cccgcctggc tgaccgccca acgacccccg cccattgacg        960
tcaataatga cgtatgttcc catagtaacg ccaatagga cttccattg acgtcaatgg         1020 gtggagtatt tacggtaaac tgcccacttg gcagtacatc aagtgtatca tatgccaagt       1080
acgcccccta ttgacgtcaa tgacggtaaa tggcccgcct ggcattatgc ccagtacatg       1140
```

```
accttatggg actttcctac ttggcagtac atctacgtat tagtcatcgc tattaccatg    1200
catggtcgag gtgagcccca cgttctgctt cactctcccc atctccccc cctcccacc      1260 cccaattttg tatttattta ttttttaatt attttgtgca gcgatggggg cggggggggg    1320
gggggggcgc gcgccaggcg gggcggggcg gggcgagggg cggggcgggg cgaggcggag    1380
aggtgcggcg gcagccaatc agagcggcgc gctccgaaag tttccttta tggcgaggcg     1440 gcggcggcgg cggccctata aaaagcgaag cgcgcggcgg gcgggagtcg tgcgcgctgc    1500
cttcgccccg tgccccgctc cgccgccgcc tcgcgccgcc cgccccggct ctgactgacc    1560
gcgttactcc cacaggtgag cgggcgggac ggcccttctc cttcgggctg taattagcgc    1620
ttggtttaat gacggcttgt ttcttttctg tggctgcgtg aaagccttga ggggctccgg    1680 gagggcccctt tgtgcggggg gagcggctcg gggcgtccg cggggggacg gctgccttcg    1740 gggggacgg ggcagggcgg ggttcggctt ctggcgtgtg accggcggct ctagagcctc     1800
tgctaaccat gttcatgcct tcttcttttt cctacagctc ctgggcaacg tgctggttat    1860
tgtgctgtct catcattttg gcaaagaatt ggatcggacc gaagcttgcg caacgcaatt    1920
aatgtgagtt agctcactca ttaggcaccc caggctttac actttatgct tccggctcgt    1980
atgttgtgtg gaattgtgag cggataacaa tttcacacta aggaggttta aaccatggct    2040
acaggctccc ggacgagtct gctcctggct tttggcctgc tctgcctgcc ctggcttcaa    2100
gagggatccg cgagctccga ggtgcagctg gtgcagagcg gcggcggcgt ggtgcagccg    2160
ggcggcagcc tgcgtctgag ctgcgccgcg agcggctaca ccttcaccaa ctacggcatg    2220
aactggattc gtcaggcccc cgggaagggc ctggagtggg tgggctggat caacacctac    2280
accggcgagc cgacctacgc agctgacttc aagcgtcgtg tcaccttcag cctcgacacc    2340
agcaagagca cggcgtacct gcaactgaac agcctgaggg ccgaggacac tgcagtttac    2400
tactgcgcga ataccccgta ctactacggt cgtagccact ggtacttcga cgtctggggc    2460
caagggaccc ttgtcaccgt ctcgagcggc ggtggcggtt ctggtggtgg tggctctggt    2520
ggcggcggat ccgatatcgt gatgacccag agcccgagca ccctgagcgc gagtccgggt    2580
gagcgcgcga ccatcacctg cagtgcgagc cagagcatca gcacctacct ggcgtggtat    2640
cagcagaaac caggtcaagc gccgcaagtg ctgatctacg ctgcgagcaa cctgcgtcc     2700 ggagtgccga accgtttcag cggtagccgt agcgggaccg atttcaccct gaccatcagc    2760
agcttgcagc cggaagactt cgcggtgtac tactgccagc agtactacag caccccgtgg    2820
accttcggtg gtggtaccaa agtggaaatc aaagcggccg cttatccata cgacgtacca    2880
gactacgcag gaggtcatca ccatcatcac catgtcgacg gatctggagg aggtgaggag    2940
aagtcccggc tgttggagaa ggagaaccgt gaactggaaa agatcattgc tgagaaagag    3000
gagcgtgtct ctgaactgcg ccatcaactc cagtctgtag gaggttgtta ataagtcgac    3060
taatgaagat ctattaacct caggtgcagg ctgcctatca gaaggtggtg gctggtgtgg    3120
ccaatgccct ggctcacaaa taccactgag atcgatcttt tccctctgc caaaaattat     3180 ggggacatca tgaagcccct tgagcatctg acttctggct aataaaggaa atttattttc    3240
attgcaatag tgtgttggaa ttttttgtgt ctctcactcg gaaggacata tgggagggca    3300
aatcatttaa aacatcagaa tgagttttg gtttagagtt tggcaacata tgcccatatg    3360
taactagcat aacccttggg ggcctctaaa cgggtcttga gggttttttt gatatccaga    3420
catgataaga tacattgatg agtttggaca aaccacaact agaatgcagt gaaaaaaatg    3480
ctttatttgt gaaatttgtg atgctattgc tttatttgta accattataa gctgcaataa    3540
```

```
acaagttggg gtgggcgaag aactccagca tgagatcccc gcgctggagg atcatccagc    3600
cggcgtcccg gaaaacgatt ccgaagccca acctttcata gaaggcggcg gtggaatcga    3660
aatctcgtga tggcaggttg ggcgtcgctt ggtcggtcat ttcgcgaacc ccagagtccc    3720
gctcagaaga actcgtcaag aaggcgatag aaggcgatgc gctgcgaatc gggagcggcg    3780
ataccgtaaa gcacgaggaa gcggtcagcc cattcgccgc caagctcttc agcaatatca    3840
cgggtagcca acgctatgtc ctgatagcgg tccgccacac ccagccggcc acagtcgatg    3900
aatccagaaa agcggccatt ttccaccatg atattcggca agcaggcatc gccatgggtc    3960
acgacgagat cctcgccgtc gggcatgcgc gccttgagcc tggcgaacag ttcggctggc    4020
gcgagcccct gatgctcttc gtccagatca tcctgatcga caagaccggc ttccatccga    4080
gtacgtgctc gctcgatgcg atgtttcgct tggtggtcga atgggcaggt agccggatca    4140
agcgtatgca gccgccgcat tgcatcagcc atgatggata ctttctcggc aggagcaagg    4200
tgagatgaca ggagatcctg ccccggcact tcgcccaata gcagccagtc ccttcccgct    4260
tcagtgacaa cgtcgagcac agctgcgcaa ggaacgcccg tcgtggccag ccacgatagc    4320
cgcgctgcct cgtcctgcag ttcattcagg caccggacag gtcggtctt gacaaaaaga    4380 accgggcgcc cctgcgctga cagccggaac acggcggcat cagagcagcc gattgtctgt    4440
tgtgcccagt catagccgaa tagcctctcc acccaagcgg ccgagaaacc tgcgtgcaat    4500
ccatcttgtt caatcatgcg aaacgatcct catcctgtct cttgatcaga tccgaaaatg    4560
gatatacaag ctcccgggag cttttttgcaa aagcctaggc ctccaaaaaa gcctcctcac    4620
tacttctgga atagctcaga ggcagaggcg gcctcggcct ctgcataaat aaaaaaaatt    4680
agtcagccat ggggcggaga atgggcggaa ctgggcggag ttaggggcgg gatgggcgga    4740
gttaggggcg ggactatggt tgctgactaa ttgagatgca tgctttgcat acttctgcct    4800 gctgggagc ctggggactt tccacacctg gttgctgact aattgagatg catgctttgc    4860
atacttctgc ctgcctgggg agcctgggga ctttccacac cctaactgac acacattcca    4920
cagacatgtg agcaaaaggc cagcaaaagg ccaggaaccg taaaaaggcc gcgttgctgg    4980 cgttttttcca taggctccgc cccctgacg agcatcacaa aaatcgacgc tcaagtcaga    5040
ggtggcgaaa cccgacagga ctataaagat accaggcgtt tccccctgga agctccctcg    5100
tgcgctctcc tgttccgacc ctgccgctta ccggatacct gtccgccttt ctcccttcgg    5160
gaagcgtggc gctttctcat agctcacgct gtaggtatct cagttcggtg taggtcgttc    5220
gctccaagct gggctgtgtg cacgaacccc ccgttcagcc cgaccgctgc gccttatccg    5280
gtaactatcg tcttgagtcc aacccggtaa gacacgactt atcgccactg gcagcagcca    5340
ctggtaacag gattagcaga gcgaggtatg taggcggtgc tacagagttc ttgaagtggt    5400
ggcctaacta cggctacact agaaggacag tatttggtat ctgcgctctg ctgaagccag    5460
ttaccttcgg aaaaagagtt ggtagctctt gatccggcaa acaaaccacc gctggtagcg    5520
gtggtttttt tgtttgcaag cagcagatta cgcgcagaaa aaaaggatct caagaagatc    5580
ctttgatctt ttctacgggg tctgacgctc agtggaacga aaactcacgt taagggattt    5640
tggtcatgag attatcaaaa aggatcttca cctagatcct tttaaattaa aaatgaagtt    5700
ttaaatcaat ctaaagtata tatgagtaaa cttggtctga cagttaccaa tgcttaatca    5760
gtgaggcacc tatctcagcg atctgtctat ttcgttcatc catagttgcc tgactccccg    5820
tcgtgtagat aactacgata cgggagggct taccatctgg ccccagtgct gcaatgatac    5880
cgcgagaccc acgctcaccg gctccagatt tatcagcaat aaaccagcca gccggaaggg    5940
```

| | | |
|---|---|---|
| ccgagcgcag | aagtggtcct gcaactttat ccgcctccat ccagtctatt aattgttgcc | 6000 |
| gggaagctag | agtaagtagt tcgccagtta atagtttgcg caacgttgtt gccattgcta | 6060 |
| caggcatcgt | ggtgtcacgc tcgtcgtttg gtatggcttc attcagctcc ggttcccaac | 6120 |
| gatcaaggcg | agttacatga tcccccatgt tgtgcaaaaa agcggttagc tccttcggtc | 6180 |
| ctccgatcgt | tgtcagaagt aagttggccg cagtgttatc actcatggtt atggcagcac | 6240 |
| tgcataattc | tcttactgtc atgccatccg taagatgctt ttctgtgact ggtgagtact | 6300 |
| caaccaagtc | attctgagaa tagtgtatgc ggcgaccgag ttgctcttgc ccggcgtcaa | 6360 |
| tacgggataa | taccgcgcca catagcagaa ctttaaaagt gctcatcatt ggaaaacgtt | 6420 |
| cttcggggcg | aaaactctca aggatcttac cgctgttgag atccagttcg atgtaaccca | 6480 |
| ctcgtgcacc | caactgatct tcagcatctt ttactttcac cagcgtttct gggtgagcaa | 6540 |
| aaacaggaag | gcaaaatgcc gcaaaaaagg gaataagggc gacacggaaa tgttgaatac | 6600 |
| tcatactctt | cctttttcaa tattattgaa gcatttatca gggttattgt ctcatgagcg | 6660 |
| gatacatatt | tgaatgtatt tagaaaaata aacaataggg gttccgcgc acatttcccc | 6720 |
| gaaaagtgcc | acctgacgtc taagaaacca ttattatcat gacattaacc tataaaaata | 6780 |
| ggcgtatcac | gaggccctt cgtc | 6804 |

<210> SEQ ID NO 9
<211> LENGTH: 5416
<212> TYPE: DNA
<213> ORGANISM: Artificial Sequence
<220> FEATURE:
<223> OTHER INFORMATION: mammalian helper vector pMAG2

<400> SEQUENCE: 9

| | | |
|---|---|---|
| tcgcgcgttt | cggtgatgac ggtgaaaacc tctgacacat gcagctcccg gagacggtca | 60 |
| cagcttgtct | gtaagcggat gccgggagca gacaagcccg tcaggcgcg tcagcgggtg | 120 |
| ttggcgggtg | tcgggctgg cttaactatg cggcatcaga gcagattgta ctgagagtgc | 180 |
| accatatgcg | gtgtgaaata ccgcacagat gcgtaaggag aaaataccgc atcaggcgcc | 240 |
| attcgccatt | caggctgcgc aactgttggg aagggcgatc ggtgcgggcc tcttcgctat | 300 |
| tacgccagct | ggcgaaaggg ggatgtgctg caaggcgatt aagttgggta acgcagggt | 360 |
| tttcccagtc | acgacgttgt aaaacgacgg ccagtgaatt cggatcggga gatctcccga | 420 |
| tcccctatgg | tcgactctca gtacaatctg ctctgatgcc gcatagttaa gccagtatct | 480 |
| gctccctgct | tgtgtgttgg aggtcgctga gtagtgcgcg agcaaaattt aagctacaac | 540 |
| aaggcaaggc | ttgaccgaca attgcatgaa gaatctgctt agggttaggc gttttgcgct | 600 |
| gcttcgcgat | gtacgggcca gatatacgcg ttgacattga ttattgacta gttattaata | 660 |
| gtaatcaatt | acggggtcat tagttcatag cccatatatg gagttccgcg ttacataact | 720 |
| tacggtaaat | ggcccgcctg gctgaccgcc caacgacccc cgcccattga cgtcaataat | 780 |
| gacgtatgtt | cccatagtaa cgccaatagg gactttccat tgacgtcaat gggtggacta | 840 |
| tttacggtaa | actgcccact tggcagtaca tcaagtgtat catatgccaa gtacgccccc | 900 |
| tattgacgtc | aatgacggta aatggcccgc ctggcattat gcccagtaca tgaccttatg | 960 |
| ggactttcct | acttggcagt acatctacgt attagtcatc gctattacca tggtgatgcg | 1020 |
| gttttggcag | tacatcaatg ggcgtggata gcggtttgac tcacggggat ttccaagtct | 1080 |
| ccaccccatt | gacgtcaatg ggagtttgtt ttggcaccaa aatcaacggg actttccaaa | 1140 |
| atgtcgtaac | aactccgccc cattgacgca aatgggcggt aggcgtgtac ggtgggaggt | 1200 |

```
ctatataagc agagctctct ggctaactag agaacccact gcttactggc ttatcgaaat    1260
taatacgact cactataggg agacccaagc tggctagcac catgcgaccc tccgggacgg    1320
ccggggcagc gctcctggcg ctgctggctg cgctctgccc ggcgtctaga gctaccagcc    1380
gcctggaggg cctgcagagc gagaaccacc gcctgcgcat gaagatcacc gagctggaca    1440
aggacctgga ggaggtgacc atgcagctgc aggacgtggg cggctgcgcg gccgccgagc    1500
agaagctgat cagcgaggag gacctgaccg gtggaggctc cggaggaggt agcggatccg    1560
gtacgaatgg gcctaagatc ccgtccatcg ccactgggat ggtggggggcc ctcctcttgc    1620 tgctggtggt ggccctgggg atcggcctct tcatgcgaag gcgccacatc gttcggaagc    1680
gcacgctgcg gaggctgctg caggagaggg agcttgtgga gcctcttaca cccagttgat    1740
aagcttgttt aaacccgctg atcagcctcg actgtgcctt ctagttgcca gccatctgtt    1800
gtttgcccct cccccgtgcc ttccttgacc ctggaaggtg ccactcccac tgtcctttcc    1860
taataaaatg aggaaattgc atcgcattgt ctgagtaggt gtcattctat tctgggggt    1920 ggggtggggc aggacagcaa gggggaggat tgggaagaca atagcaggca tgctggggat    1980
gcggtgggct ctatggcttc tgaggcggaa agaaccagct ggggctctag ggggtatccc    2040
cggcgcgcca atttaacgcg aattaattct gtggaatgtg tgtcagttag ggtgtggaaa    2100
gtccccaggc tccccagcag gcagaagtat gcaaagcatg catctcaatt agtcagcaac    2160
caggtgtgga aagtccccag gctccccagc aggcagaagt atgcaaagca tgcatctcaa    2220
ttagtcagca accatagtcc cgcccctaac tccgcccatc ccgcccctaa ctccgcccag    2280
ttccgcccat tctccgcccc atggctgact aatttttttt atttatgcag aggccgaggc    2340
cgcctctgcc tctgagctat tccagaagta gtgaggaggc ttttttggag gcctaggctt    2400
ttgcaaaaag ctcccgggag cttgtatatc cattttcgga tctgatcagc acgtgttgac    2460
aattaatcat cggcatagta tatcggcata gtataatacg acaaggtgag gaactaaacc    2520
atggccaagt tgaccagtgc cgttccggtg ctcaccgcgc gcgacgtcgc cggagcggtc    2580
gagttctgga ccgaccggct cgggttctcc cgggacttcg tggaggacga cttcgccggt    2640
gtggtccggg acgacgtgac cctgttcatc agcgcggtcc aggaccaggt ggtgccggac    2700
aacaccctgg cctgggtgtg ggtgcgcggc ctggacgagc tgtacgccga gtggtcggag    2760
gtcgtgtcca cgaacttccg ggacgcctcc gggccggcca tgaccgagat cggcgagcag    2820
ccgtgggggc gggagttcgc cctgcgcgac ccggccggca actgcgtgca cttcgtggcc    2880
gaggagcagg actgacacgt gctacgagat ttcgattcca ccgccgcctt ctatgaaagg    2940
ttgggcttcg gaatcgtttt ccgggacgcc ggctggatga tcctccagcg cggggatctc    3000
atgctggagt tcttcgccca ccccaacttg tttattgcag cttataatgg ttacaaataa    3060
agcaatagca tcacaaattt cacaaataaa gcatttttt cactgcattc tagttgtggt    3120
ttgtccaaac tcatcaatgt atcttatcat gtctgtatac cgtcgacctc tagctagagc    3180
ttggcgtaat catggtcata gctgtttcct gtgtgaaatt gttatccgct cacaattcca    3240
cacaacatac gagccggaag cataaagtgt aaagcctggg gtgcctaatg agtgagctaa    3300
ctcacattaa ttgcgttgcg ctcactgccc gctttccagt cgggaaacct gtcgtgccag    3360
ctgcattaat gaatcggcca acgcgcgggg agaggcggtt tgcgtattgg gcgctcttcc    3420
gcttcctcgc tcactgactc gctgcgctcg gtcgttcggc tgcggcgagc ggtatcagct    3480
cactcaaagg cggtaatacg ttatccacag aatcaggggg ataacgcagg aaagaacatg    3540
tgagcaaaag gccagcaaaa ggccaggaac cgtaaaaagg ccgcgttgct ggcgtttttc    3600
```

```
cataggctcc gcccccctga cgagcatcac aaaaatcgac gctcaagtca gaggtggcga    3660
aacccgacag gactataaag ataccaggcg tttcccctg gaagctccct cgtgcgctct     3720
cctgttccga ccctgccgct taccggatac ctgtccgcct ttctcccttc gggaagcgtg    3780
gcgctttctc atagctcacg ctgtaggtat ctcagttcgg tgtaggtcgt tcgctccaag    3840
ctgggctgtg tgcacgaacc ccccgttcag cccgaccgct gcgccttatc cggtaactat    3900
cgtcttgagt ccaacccggt aagacacgac ttatcgccac tggcagcagc cactggtaac    3960
aggattagca gagcgaggta tgtaggcggt gctacagagt tcttgaagtg gtggcctaac    4020
tacggctaca ctagaaggac agtatttggt atctgcgctc tgctgaagcc agttaccttc    4080
ggaaaaagag ttggtagctc ttgatccggc aaacaaacca ccgctggtag cggtggtttt    4140
tttgtttgca agcagcagat tacgcgcaga aaaaaggat ctcaagaaga tcctttgatc      4200
ttttctacgg ggtctgacgc tcagtggaac gaaaactcac gttaagggat tttggtcatg    4260
agattatcaa aaaggatctt cacctagatc cttttaaatt aaaaatgaag ttttaaatca    4320
atctaaagta tatatgagta aacttggtct gacagttacc aatgcttaat cagtgaggca    4380
cctatctcag cgatctgtct atttcgttca tccatagttg cctgactccc cgtcgtgtag    4440
ataactacga tacgggaggg cttaccatct ggccccagtg ctgcaatgat accgcgagac    4500
ccacgctcac cggctccaga tttatcagca ataaaccagc cagccggaag ggccgagcgc    4560
agaagtggtc ctgcaacttt atccgcctcc atccagtcta ttaattgttg ccgggaagct    4620
agagtaagta gttcgccagt taatagtttg cgcaacgttg ttgccattgc tacaggcatc    4680
gtggtgtcac gctcgtcgtt tggtatggct tcattcagct ccggttccca acgatcaagg    4740
cgagttacat gatcccccat gttgtgcaaa aaagcggtta gctccttcgg tcctccgatc    4800
gttgtcagaa gtaagttggc cgcagtgtta tcactcatgg ttatggcagc actgcataat    4860
tctcttactg tcatgccatc cgtaagatgc ttttctgtga ctggtgagta ctcaaccaag    4920
tcattctgag aatagtgtat gcggcgaccg agttgctctt gcccggcgtc aatacgggat    4980
aataccgcgc cacatagcag aactttaaaa gtgctcatca ttggaaaacg ttcttcgggg    5040
cgaaaactct caaggatctt accgctgttg agatccagtt cgatgtaacc cactcgtgca    5100
cccaactgat cttcagcatc ttttactttc accagcgttt ctgggtgagc aaaaacagga    5160
aggcaaaatg ccgcaaaaaa gggaataagg gcgacacgga aatgttgaat actcatactc    5220
ttcctttttc aatattattg aagcatttat cagggttatt gtctcatgag cggatacata    5280
tttgaatgta tttagaaaaa taaacaaata ggggttccgc gcacatttcc ccgaaaagtg    5340
ccacctgacg tctaagaaac cattattatc atgacattaa cctataaaaa taggcgtatc    5400
acgaggccct ttcgtc                                                    5416
```

<210> SEQ ID NO 10
<211> LENGTH: 38
<212> TYPE: PRT
<213> ORGANISM: Artificial Sequence
<220> FEATURE:
<223> OTHER INFORMATION: C-terminal sequence of GABAB receptor 1

<400> SEQUENCE: 10

Glu Glu Lys Ser Arg Leu Leu Glu Lys Glu Asn Arg Glu Leu Glu Lys
1               5                   10                  15

Ile Ile Ala Glu Lys Glu Glu Arg Val Ser Glu Leu Arg His Gln Leu
            20                  25                  30

Gln Ser Val Gly Gly Cys

```
<210> SEQ ID NO 11
<211> LENGTH: 38
<212> TYPE: PRT
<213> ORGANISM: Artificial Sequence
<220> FEATURE:
<223> OTHER INFORMATION: C-terminal sequence of GABAB 5 receptor 2

<400> SEQUENCE: 11

Thr Ser Arg Leu Glu Gly Leu Gln Ser Glu Asn His Arg Leu Arg Met
 1               5                  10                  15

Lys Ile Thr Glu Leu Asp Lys Asp Leu Glu Glu Val Thr Met Gln Leu
            20                  25                  30

Gln Asp Val Gly Gly Cys
        35
```

EUKARYOTIC CELL DISPLAY SYSTEMS

CROSS REFERENCE TO RELATED APPLICATIONS

This application is a of U.S. application under 37 CFR 1.53(b) which claims the benefit of U.S. Provisional Application No. 61/003,413 filed Nov. 16, 2007.

TECHNICAL FIELD OF THE INVENTION

This invention relates to the field of protein display and provides display systems which facilitate the display of protein libraries on the surface of eukaryotic host cells, including yeast cells and mammalian cells. The compositions and methods of the invention are particularly useful for identifying proteins with desired properties from a vast repertoire of proteins. This system also provides methods for producing soluble protein for use in functional assays and for directing expressed proteins to different cellular organelles without any molecular manipulation of the display vector.

BACKGROUND OF THE INVENTION

Phage display systems are regarded as a core technology platform for the construction and screening of polypeptide libraries, particularly antibody libraries. This is attributed to numerous practical considerations including, the availability of various genetic tools, the convenience of manipulation, and the high transformation efficiency of *E coli* cells. Today, naive antibody libraries displayed on phage are routinely used for antibody discovery, thereby obviating the need for animal immunizations and the use of traditional hybridoma technology. However, despite the successful use of phage display in antibody discovery and engineering protocols, there are a number of drawbacks associated with the expression and display of eukaryotic proteins in prokaryotic systems.

For example, some eukaryotic proteins cannot be functionally expressed in prokaryotic cells. In addition, prokaryotic host cells are typically not able to accomplish the full range of post-translational modifications that are characteristic of eukaryotic host cells. Some of the limitations associated with the use of a prokaryotic display system can be overcome by the use of a eukaryotic display system. For example, a unique advantage associated with the use of a yeast display system is attributed to the fact that yeast cells can be cultivated to high densities using relatively simple and inexpensive culture medium. Generally speaking, eukaryotic host cells can accommodate the display of relatively large proteins, and are capable of post translation modifications including complex glycosylation. In addition, because eukaryotic cells are larger in size than prokaryotic cells, the members of a display libraries can be efficiently screened for single cells expressing proteins with desired properties (i.e., binding specificities) by flow cytometry.

The display of heterologous protein on the cell surface of *Saccharomyces cerevisiae* was first described in 1993 using a cell wall protein-based fusion protein design in which alpha-galactosidase was fused to the C-terminal half of cell wall protein alpha-agglutinin AGA 1 (Schreuder M P et al, Yeast 9:399-409). Since then, numerous yeast display systems based on fusing a library of proteins of interest to cell wall proteins have been reported (Kondo M et al). Among all of the cell wall fusion protein-based display systems, the system created by Dane Wittrup based on a-agglutinin receptor has been widely used to display various proteins libraries including various formats of antibody libraries (U.S. Pat. No. 6,300,065, U.S. Pat. No. 6,423,538, U.S. Pat. No. 6,696,251, and U.S. Pat. No. 6,699,658).

Similarly, a number of approaches have been designed to achieve the display of proteins on the surface of mammalian cells using display vectors which comprise a membrane anchor proteins fused to the members of a protein library comprising a diverse repertoire of protein sequences. Typically, the anchor protein comprises a protein derived from the membrane domain of a cell surface receptor (Chestnut et al, 1996, *J Immunological Methods*; Ho et al, 2006, PNAS, 103: 9637-9642), such as a GPI anchor sequences (U.S. Pat. No. 6,838,446), or a non-cleavable type 11 signal anchor sequence (U.S. Pat. No. 7,125,973). For example, the pDISPLAY vector (Invitrogen Life Technologies), is a commercially available vector which directs the cell surface display of proteins on mammalian cell utilizes the membrane domain of cell surface platelet derived growth factor receptor PDGFR. Proteins expressed from the pDISPLAY vector are anchored to the plasma membrane of the host cell and displayed on the extracellular side of the plasma membrane.

There are a number of drawbacks associated with the use of a cell surface display system based on fusing the protein library to a cell surface anchor protein. For example, because the proteins of interest are directly fused to the outer surface anchor protein, the protein of interest can only be expressed as a part of the membrane protein. In order to obtain soluble protein for evaluation in screening and/or functional assays, additional molecular cloning steps are required in order to transfer the coding sequences of interest to an expression vector which directs the expression of soluble protein. Use of a cell wall fusion protein-based design also eliminates the possibility of evaluating the functional properties of expressed proteins inside cellular organelles such as mitochondria, Golgi apparatus, endoplasmic reticulum etc.

Therefore, there is an unmet need for an alternative protein display system which facilitates the display of protein libraries on eukaryotic cell surfaces, using a vector design which can also be used to direct expression of library proteins as either soluble proteins or as intracellular proteins without any molecular manipulations to reengineer the display vector.

SUMMARY OF THE INVENTION

This invention provides protein display systems that are capable of displaying diverse libraries of polypeptides on the surface of eukaryotic cells. The compositions and methods of the invention can be used to display the protein products encoded by a diverse repertoire of coding sequences on the surface of yeast cells or mammalian cells. The compositions and methods of the invention are particularly useful for the display of antibody libraries for antibody discovery (i.e. screening) and/or optimization (e.g., molecular evolution) protocols. Notably, the displayed library members are not anchored to the cell membrane as a consequence of being directly fused to a coding sequence that encodes a cell wall outer membrane protein.

In one embodiment, the invention provides a method for displaying a repertoire of polypeptide sequences on the surface of eukaryotic cells. As depicted in FIG. 1, the disclosed display systems generally have two components: 1) an expression (or display) vector and 2) a corresponding helper vector. As disclosed herein a display system comprises a pair of vectors (i.e., a display vector and a corresponding helper vector) that are chosen based on the identity of the host cell. Accordingly, an alternative embodiment of the invention provides kits in suitable packaging comprising at least one display vector and a helper vector designed to direct the display of a collection of protein sequences on the surface of particular eukaryotic host cells.

The display vector comprises a fusion protein in which the members of the encoded protein library are fused to a first adapter sequence (referred to herein as "adapter1"). Introduction of a display vector, in the absence of a helper vector, into a eukaryotic host cells, such as yeast cells, or mammalian cells, leads to expression and secretion of polypeptides that are fused in-frame with adapter1.

More specifically, the invention provides the yeast expression vectors embodied by the library display vectors pMAT9, and pMAT12 (see FIGS. 2A & 2B). In pMAT9 and pMAT12 vectors, the expression of the adapter1 fusion protein is under control of a yeast promoter. Suitable strains of yeast host cells for use with the vectors and display systems of the invention include but are not limited to *S. cerevisiae, Pichia pastoris, H. polymorphs*, and *C. albicans*. Generally speaking, the disclosed yeast display vector comprises at least one expression cassette for an adapter1 fusion protein, which comprises the following functional elements: (1) a yeast promoter; (2) a yeast signal sequence; (3) a gene of interest; (4) adapter1 coding sequence.

In an alternative embodiment the invention provides the mammalian expression vector pMAG10 (see FIG. 7). In the pMAG10 vector, the expression of adapter1 fusion protein is under control of a mammalian promoter. Suitable mammalian host cells for use with the vectors and display systems of the invention include but are not limited to HEK293 and CHO cells.

Generally speaking, the disclosed helper vectors encode a fusion protein comprising a cell surface anchor protein in combination with a second adapter sequence (referred to herein as adapter2) that is capable of interacting in a pair-wise manner with a corresponding adapter sequence fused to the protein product of the library display vector. In specific embodiments the invention provides the yeast helper vectors pMAT7 (FIG. 3A) and pMAT8 (FIG. 3B). Each of the yeast helper display vectors directs the expression of a fusion protein comprising adapter 2 fused to different yeast cell outer wall proteins. More specifically, pMAT 3 directs the expression of adapter 2 fused to the Aga2 proteins, and pMAT8 directs the expression of adapater2 Cwp2 fusion proteins.

The invention also provides the mammalian helper vectors pMAG2 (see FIG. 8). pMAG2 directs expression of adapter2 sequences fused to the transmembrane domain of human EGF receptor. An alternative embodiment, the invention provides eukaryotic (i.e., yeast and mammalian) host cells comprising a helper vectors of the invention. For example, a suitable host cell comprising a chromosomal integrant of one of the helper display vectors of the invention.

Co-expression of an expression vector of the invention in combination with a corresponding helper vector directs the display of the polypeptide product of the display library members anchored to the cell membrane or cell wall of the host cell. Surface display results from the pairwise interaction of the adapters (i.e., adapter1 fused to the protein product of the display library, and adapter2 fused to a host cell specific anchor protein) which has the effect of directing the display of the protein library on the surface of the host cell.

For example, co-expression of a helper vector comprising an adapter sequence fused to a yeast outer cell wall protein, in combination with a yeast display vector comprising a library of fusion proteins comprising a corresponding adapter sequence present in the fusion proteins expressed by the fusion proteins encoded by the display vector provides a yeast cell surface display system. Similarly, co-expression of a mammalian helper vector comprising an adapter a corresponding adapter sequence fused to a mammalian cell surface anchor protein in combination with a mammalian display vector comprising an adapter sequence that interacts with in a pairwise manner with the adapter present in the helper vector provides a mammalian cell surface display system.

The use of an expression vector of the invention in the absence of a helper vector, results in the expression of the encoded proteins as soluble proteins by the host cells. Therefore, the disclosed display vectors also facilitate the direct expression of library proteins as either soluble protein or as intracellular proteins without any molecular manipulation (i.e., DNA digestion and/or ligation) of the vector. Accordingly, the invention also provides an efficient method to evaluate the functional characteristics of the members of the display library proteins.

BRIEF DESCRIPTION OF THE DRAWINGS

FIGS. 1A and 1B provides schematic representations of the components of the yeast display system (FIG. 1A) and mammalian display system (FIG. 1B) of the invention.

FIG. 5A represents the fluorescent signal detected on the surface of yeast cells that are contransfected with the pMAT9 display vector and the pMAT8 helper vector. The control micrograph presented in panel (a) shows a lack of fluorescence by cells that are not induced. The fluorescence micrograph presented in panel (b) shows a fluorescent signal on the surface of induced yeast cells. Panel (c) provides a phase contrast micrograph of the same cells depicted in the fluorescence micrograph of provided in panel (d). The surface fluorescence (green signal) detected in panel (d) illustrates the surface expression of Myc-tagged adapter2 fusion proteins anchored to the outer wall of the induced yeast cells. FIG. 5B provides the results of a flow cytometry (FACScan) analysis of yeast cells displaying HA-tagged scFv antibodies on their surface resulting from the expression of vectors pMAT9 and pMAT12. FIG. 5C shows the co-localization of adapter1 fusion proteins and adapter2 fusion proteins on the outer membrane of yeast cells after galactose induction. HA-tagged adapter 1 fusion proteins (product of the display vector) expressed on the cell surface are detected by a green fluorescent signal illustrated by the cells panel a). Myc-tagged adapter2 fusion proteins (products of the helper vector) expressed on the cell surface are detected by a red fluorescent signal illustrated by the cells in panel b). The presence of a yellow fluorescent signal on the surface of the cell in panel c) establishes the co-localization of the two fusion proteins and results from the merger of the green and red fluorescence.

FIG. 10 sets forth the nucleotide and amino acid sequences of the adapter sequences used in the examples disclosed herein to practice the disclosed eukaryotic surface display systems. SEQ ID NO: 1 provides the nucleotide sequence encoding the adapter element referred to as adapter1. SEQ ID NO:2 provides the nucleotide sequence of the adapter element referred to as adapter2. SEQ ID NOS:10 and 11 provides the amino acid sequences of adapter1 and adapter2, respectively.

FIG. 11 sets forth the nucleotide sequence of a polynucleotide encoding an anti-VEGF scFv antibody fused with adapter1 (GR1) (SEQ ID NO: 3).

FIGS. 12A and 12B set forth the nucleotide sequence of the yeast pMAT12 display vector (SEQ ID NO: 4).

FIGS. 13A and 13B set forth the nucleotide sequence of the yeast helper vector pMAT7 (SEQ ID NO: 5).

FIGS. 14A and 14B set forth the nucleotide sequence of the yeast helper vector pMAT8 (SEQ ID NO: 6).

FIGS. 15A and 15B set forth the nucleotide sequence of the yeast expression vector pMAT19 (SEQ ID NO: 7).

FIGS. 16A and 16B set forth the nucleotide sequence of the mammalian display vector pMAG10 (SEQ ID NO: 8).

FIGS. 17A and 17B set forth the nucleotide sequence of the mammalian helper vector pMAG2 (SEQ ID NO: 9).

DETAILED DESCRIPTION OF THE INVENTION

Figure 2A:
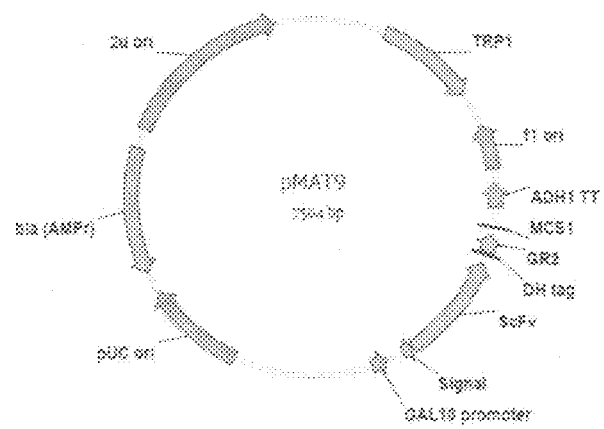
FIGS. 2A and 2B provide schematic representations of the yeast display vectors pMAT9 (FIG. 2A) and pMAT12 (FIG. 2B).

As used in this specification and claims, the singular form "a," "an," and "the" include plural references unless the context clearly dictates otherwise. As used herein the term "species" refers to a group of organisms which are very similar in morphology, anatomy, physiology and genetics due to having relatively recent common ancestors. Different species usually demonstrate common features in performing common function of life regardless their other differences. For example, human and mouse cells share certain molecular landmarks, and are considered to be members of the same species (i.e., mammalian cells) while human cells and yeast cells are different species of eukaryotic host cells.

As used herein the term "genetic packages" refers to viruses or cells, in which polynucleotide sequences encoding proteins of interest are packaged for expression and/or surface display.

The terms "prokaryotic system" and "prokaryotic genetic packages" are used interchangeably herein to refer to prokaryotic cells such as bacterial cells or prokaryotic viruses such as phages or bacterial spores.

The term "eukaryotic system" and "eukaryotic host cells" are used interchangeably herein to refer to eukaryotic cells including cells of animal, plants, fungi and protists, and eukaryotic viruses such as retrovirus, adenovirus, beculovirus.

As used herein the term "gene," is used to refer to a DNA sequence which codes for a protein. The term does not include untranslated flanking regions such as RNA transcription initiation signals, polyadenylation addition sites, promoters or enhancers.

The term "expression cassette" is used here to refer to a functional unit that is built in a vector for the purpose of expressing recombinant proteins/peptides. It usually consists of a promoter or promoters, a ribosome binding site or ribosome binding sites, and the cDNA of the expression target. Other accessory components can be added to construct an expression cassette.

As used herein the term "vector" refers to a nucleic acid molecule, preferably self replicating, which transfers an inserted nucleic acid molecule into and/or between host cells. Typically vectors are circular DNA comprising a replication origin, a selection marker, and or viral package signal, and other regulatory elements. Vector, vector DNA, plasmid DNA are interchangeable terms in description of this invention. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions.

As used herein the term "expression vector" is a polynucleotide which, when introduced into an appropriate host cell, can be transcribed and translated into a polypeptide(s). The terms "expression vector," multi-species expression vector" and "cross species expression vector" refer to vectors that direct the soluble expression of proteins of interest fused in frame with an adapter sequence which is characterized by an ability to associate in a pairwise fashion with an adapter sequence produced by a helper vector of the invention.

The term "helper vector" refers to a genetic package, or host cell-specific vector designed to produce fusion proteins comprising an anchor protein fused in frame with an adapter sequence which is characterized by an ability to associate in a pairwise fashion with an adapter sequence produced by an expression vector of the invention. Helper vectors can be introduced into recipient host cells, in combination with an expression vector, transiently by cotransformation, or permanently by integration into host genome.

Figure 7:
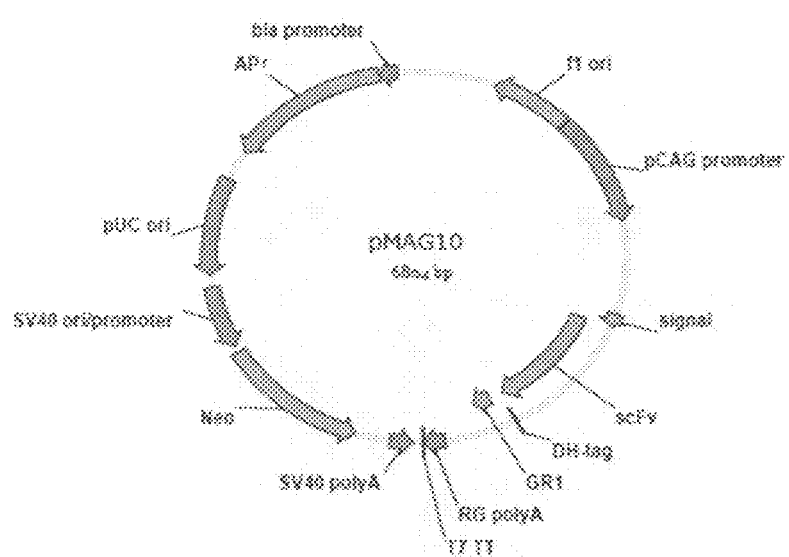
FIG. 7 provides a schematic representation of the mammalian expression vector pMAG10. Expression of the adapter1 (GR1) fusion proteins encoded by the pMAG10 vector is under control of a mammalian promoter.
Figure 8:
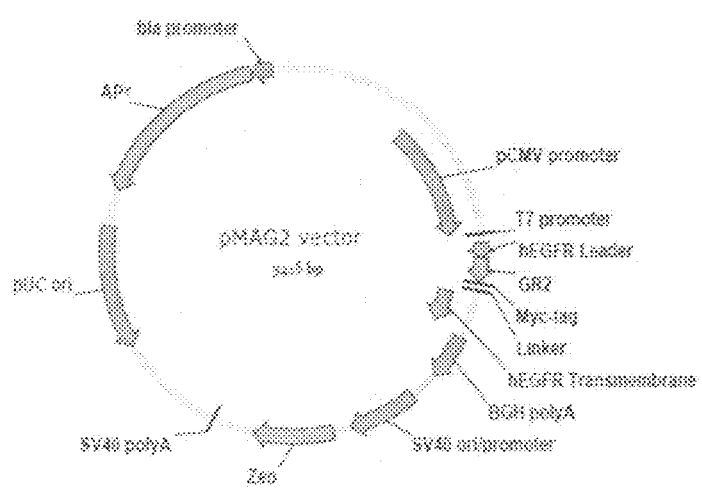
FIG. 8 provides a schematic representation of the mammalian helper vector pMAG2, which produces a fusion protein comprising an adapter2 (GR2) sequence fused to the transmembrane domain of the human EGF receptor.

As used herein the term "display vector set" refers to particular combinations of expression vectors and helper vectors which are designed to comprise complementary adapter sequences which function to display polypeptides on the surface of particular species of genetic packages or host cells. For example, a set of vectors pMAG10 (FIG. 7) and pMAG2 (FIG. 8) for mammalian display, a set of vectors pMAT9 (FIG. 2A) and pMAT8 (FIG. 3B) for yeast display.

As used herein the term "expression system" usually connotes a suitable host cell comprised of an expression vector that can function to yield a desired expression product.

As used herein, the term "surface antigen" refers to the plasma membrane components of a cell. It encompasses integral and peripheral membrane proteins, glycoproteins, polysaccharides and lipids that constitute the plasma membrane. An "integral membrane protein" is a transmembrane protein that extends across the lipid bilayer of the plasma membrane of a cell. A typical integral membrane protein consists of at least one "membrane spanning segment" that generally comprises hydrophobic amino acid residues. Peripheral membrane proteins do not extend into the hydrophobic interior of the lipid bilayer and they are bound to the membrane surface by noncovalent interaction with other membrane proteins.

The term "outer surface anchor" as used herein is to refer a polypeptide, or protein, or protein domain, which will be integrated into or attached on the out surface of a genetic package. It may be from the nature, or be artificially created by any means. The term as used interchangeably with the terms "surface anchor sequence" or "signal coat protein", "outer surface sequences", "outer membrane protein", "membrane anchor protein", "anchor protein", "cell wall protein", "GPI anchor signal," "GPI attachment signal," and signal anchor sequence.

The term "signal sequence" and "leader sequence" are used interchangeably herein to refer a DNA sequence encoding a secretory peptide that is a component of a larger peptide on DNA level. It may also refer the amino acide sequence of a secretory peptide. The function of secretory peptide is to direct the larger polypeptide through a secretory pathway of a cell.

As used herein the terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

As used herein the term "amino acid" refers to either natural and/or unnatural or synthetic amino acids, including glycine and both the D or L optical isomers, and amino acid analogs and peptidomimetics.

As used herein the terms "polypeptide", "peptide, "protein," and "protein of interest" are used interchangeably herein to refer to polymers of amino acids of any length. The polymer may be linear, cyclic, or branched, it may comprise modified amino acids, and it may be interrupted by non amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component.

As used herein the term "antibody" refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains interconnected by disulfide bonds. The immunoglobulins represent a large family of molecules that include several types of molecules, such as IgD, IgG, IgA, 1gM and IgE. The term "immunoglobulin molecule" includes, for example, hybrid antibodies, chimeric antibodies, humanized antibodies and fragments thereof. Non-limiting examples of antibody fragments include a Fab fragment consisting of the VL, VH, CL and CH1 domains; (4) an Fd fragment consisting of the VH and CH1 domains; (5) an Fv fragment consisting of the VL and VH domains of a single arm of an antibody; (6) an F(ab')$_2$ fragment, a bivalent fragment comprising two Fab fragments linked by a disulfide bridge at the hinge region; (7) a diabody consisting of two identical single chain Fv with shorter linker; (8) a ccFv antibody consisting of Fv stabilized by a pair of coiled-coil domains interaction.

As used herein the term "pair-wise interaction" means that the two adapters can interact with and bind to each other to form a stable complex. The stable complex must be sufficiently long-lasting to permit packaging the polypeptide onto the outer surface of a genetic package. In practice, the resulting complex or dimer must be able to withstand whatever conditions exist or are introduced between the moment of formation and the moment of detecting the displayed polypeptide, these conditions being a function of the assay or reaction which is being performed.

As used herein the term "host cell" includes an individual cell or cell culture which can be, or has been, a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

As used herein the term "repertoire" refers to the total collection of variant members of a functional or physical origin. A library is the total collection of homologous variant members. In general, a repertoire depicts much wider and larger functional and physical landscape, therefore, it can include libraries that are functionally defined. For example, the entire genetic capacity of immunoglobulin in a species is its immunoglobulin repertoire; for the purpose of protein engineering, a library usually refers to a collection of variant molecules that derived from one or defined number of parental (or ancestor) proteins. A repertoire created for a particular purpose, such as a collection of sequences generated during the optimization of a therapeutic antibody, includes all libraries generated for such a purpose.

As used herein the term "adapters" refer to complementary elements or components that are capable of a pair-wise interaction with each other to form a physical unity based on the physical and/or functional match between the two different interacting protein sequences. Adapters can be proteins, protein domains, peptides, compounds of non-polypeptide, etc. derived from natural or artificial origins. Typical examples for adapters include two interacting polypeptides that form a coiled-coil heterodimer such as GM and GR2 (SEQ ID NOS: 10 and 11 respectively) polypeptide sequences, c-fos and c-jun, natural and artificial leucine zippers, specific protein domains derived from a ligand and its cognate receptor, sequences derived from specific binding domains of heterodimeric complexes which are known to interact with each other to form a functional unit, or protein sequences derived from two different non-polypeptide components such as biotin and strepavidin. Generally speaking adapters suitable for use in surface display systems described in this disclosure can be endogenous or exogenous to the host species, and/or artificially derived.

As used herein, a linear sequence of peptide is "essentially identical" to another linear sequence, if both sequences exhibit substantial amino acid or nucleotide sequence homology. Generally, essentially identical sequences are at least about 60% identical with each other, after alignment of the homologous regions. Preferably, the sequences are at least about 70% identical, more preferably, they are at least about 80% identical, more preferably, they are at least about 90% identical, of more preferably, the sequences are at least about 95% identical.

The display of polypeptides on the surface of genetic packages represents a powerful methodology for screening libraries of polypeptide sequences. The ability to construct libraries of enormous molecular diversity and to select for molecules with desired properties has made this technology broadly applicable to numerous applications, including screening/discovery protocols as well as molecular evolution protocols. The origins of phage display date to the mid 1980s when George Smith first expressed an exogenous segment of a protein on the surface of bacteriophage M13 virus particles by fusing the exogenous sequence to a phage coat protein 30 (Science (1985) 228: 1315 1317). Since then, a range of display systems have been developed based on George Smith's findings. These systems can be broadly classified into two categories (U.S. Pat. Nos. 5,969,108 and 5,837,500). The first generation system is a one-vector system. The vector in this system contains the entire phage genome, insert therein an exogenous sequence in-frame with a coat protein gene. Because the resulting phage particles carry the entire phage genomes, they are relatively unstable and less infectious. The second generation system, commonly referred to as the phagemid system, has two components: (1) a phagemid vector carrying the exogenous sequence fused to phage coat protein, and a phage-derived origin of replication to allow packaging of the phagemid into a phage particle; and (2) a helper phage carrying all other sequences required for phage packaging.

The helper phage is typically replication-defective such as M13K07 helper phage manufactured by Amersham Pharmacia Biotech and its derivative VC SM13 that is produced by Stratagene. Upon superinfection of a bacterial cell with the helper phages, newly packaged phages carrying the phagemid vector and displaying the exogenous sequence are produced. As such, the prior phagemid system requires fusion of the exogenous sequence to at least part of a phage outer-surface sequence (i.e. the coat sequence). The fusion or display sites most commonly used are within genes III and VIII of M13 bacteriophage, although genes VI, VII and IX fusions have been reported.

Alternative to the coat protein fusion system, various modifications to the fusion phagemid system have been described. Crameri et al. devised a system to display cDNA products, in which Fos oncogene was inserted adjacent to the exogenous sequence to be displayed on a phagemid vector, and Jun oncogene was inserted adjacent to gene III on the same vector (see Crameri et al. (1993) Gene 137:69 75). The Crameri approach exploits the preferential interaction between fos and jun proteins: as the Fos-exogenous polypeptide is expressed and secreted into the periplasmic space, it forms a complex with pIII-Jun which is then packaged into the phage particles upon super infection with M13K07 helper phage.

Another variant similar to the Crameri system is the "cysteine-coupled" display system described in WO 01/05950, U.S. Pat. No. 6,753,136. The attachment and display of the exogenous polypeptide are mediated by the formation of disulfide bond between two cysteine residues in the bacterial periplasmic space, one of which is contained in the exogenous sequence, and the other is inserted in the outer-surface sequence. Although those two systems avoid the expression of a fusion comprising the exogenous protein linked to an outer-surface protein, the systems fails to minimize the toxicity of coat proteins to the host cells because of the constitutive expression of the coat protein pill in display vectors. In addition, the formation of disulfide bond between two cysteine residues requires high level expression of both of exogenous sequence and coat protein pill. Therefore, any lower expression member will lose the chance to display.

Recently, Wang et al described an alternative phage display system based on an adapter-directed display system (U.S. Pat. No. 7,175,983), which comprise: (a) an expression vector comprising a coding sequence that encodes the exogenous polypeptide fused in-frame to a first adapter sequence; (b) a helper vector comprising outer-surface sequences encoding outer-surface proteins necessary for packaging the phage particle, and one of the outer-surface proteins is fused in-frame to a second adapter. Therefore, displays of the exogenous polypeptides are achieved by pairwise interaction between the first and second adapters.

Display of polypeptides on the surface of *E. coli* was developed as an alternative to phage display technology. Similar to phage display, bacterial display is an attractive method due to the availability of various genetic tools and mutant strains, and its high transformation efficiency that makes it ideal for large size library construction and screening. In gram-negative bacteria, surface display systems based on fusion of protein to be display to various anchoring proteins have been reported, in which outer membrane proteins (Chang and Lo 2000, *J Biotechnol* 78:115-122; Lee et al. 2004, *Appl Environ Microbiol* 70:5074-5080), pili and flagella (Westerlund-Wikstrom et al. 1997, *Protein Eng* 10:1319-1326), modified lipoproteins (Georgiou et al. 1996, *Protein Eng* 9: 239-247), ice nucleation proteins (Jung et al. 1998, *Nat Biotechnol* 16:576-580), and autotransporters (Veiga et al. 2003, *J Bacterial* 185:5585-5590) were used as the anchors for display.

The display of heterologous protein on the cell wall of the eukaryotic host cell *Saccharornyces cerevisiae* was first described in 1993 by fusion of alpha-galactosidase to C-terminal half of cell well protein alpha-agglutinin AGA1 (Schreuder M P et al, *Yeast* 9:399-409). Since then, various yeast display systems base on fusion of the protein of interest to various cell well proteins were reported (Kondo M et al). Almost all of the cell-surface display systems developed for yeast are glycosyl phosphatidylinositol (GPI) anchor-dependent. More than a dozen of yeast cell well proteins with a putative GPI attachment signal at the C-termini have been proven capable of displaying peptides and proteins, which includes a-agglutinin (Aga1 and Aga2), Cwp1, Cwp2, Gas1p, Yap3p, Flo1p, Crh2p, Pir1, Pir2, Pir4, and Icwp in *S. cerevisiae*; HpSEDI, HpGASI, HpTIPI, HPWPI in *Hansenula polymorpha*, and Hwp1p, Als3p, Rbt5p in *Candida albicans*. To date, over twenty heterologous proteins have been successfully displayed on yeast cell surface.

Among all of the cell-surface display systems described above, the system created by Dane Wittrup base on a-agglutinin receptor has been widely used for display various peptides and proteins such as scFv antibody and antibody libraries (U.S. Pat. No. 6,300,065, U.S. Pat. No. 6,423,538, U.S. Pat. No. 6,696,251, and U.S. Pat. No. 6,699,658). In *S. cerevisiae*, the a-agglutinin receptor acts as an adhesion molecule to stabilize cell-cell interactions and facilitate fusion between mating "a" and a haploid yeast cells. The receptor consists of a core subunit Aga1 and small subunit Aga2. Aga1 is secreted from the cell and becomes covalently attached to El-linked glucans in the extra cellular matrix of the yeast cell wall though its GPI anchor-attachment signal. Aga2 binds to Aga1 through two disulfide bonds, presumably in the golgi, and after secretion remains attached to the cell via Aga1. This yeast display system takes advantage of the association of Aga1 and Aga2 proteins to display a recombinant protein on the yeast cell surface through fusion of protein with the Aga2 subunit.

The Wittrup system has been adapted for multi-chain polypeptides such as immunoglobulin Fab fragments (Hufton et al, US patent application 2003/0186374 A1). Hufton et al mention the possible use of the Fos/Jun interaction as the basis of a display system suitable for use in eukaryotic cells. However, Hufton et at did not provide an enabling description of how the Fos/Jun interaction can be utilized to direct protein display in eukaryotic host cells. However the reference only teaches how to use Ag2 fusion developed by Dane Wittrup (U.S. Pat. No. 6,300,065, U.S. Pat. No. 6,423,538, U.S. Pat. No. 6,696,251, and U.S. Pat. No. 6,699,658) for yeast display of Fab antibody, and how to transfer gene from phage display vector to yeast vector by molecular cloning.

A number of approaches have been used to achieve display of proteins on the surface of mammalian cells based on the use of display vectors that are designed to display a repertoire of proteins of interest directly fused to various membrane anchor proteins, which includes membrane domains of cell surface receptors (Chesnut et al, 1996, *J Immunological Methods*; Ho et al, 2006, PNAS, 103:9637-9642), GPI anchor sequences (U.S. Pat. No. 6,838,446), non-cleavable type 11 signal anchor sequences (U.S. Pat. No. 7,125,973). A typical example is the pDISPLAY vector, that is a commercially available vector to display protein on mammalian cell surface provided by Invitrogen Corp. In this vector, the protein of interest will be fused with a membrane domain of cell surface receptor PDGFR. An alternative approach was also reported in U.S. Pat. No. 6,919,183. In this system, a cell surface capture molecule such as protein G, protein A was used to capture the antibody molecules on mammalian cell surface.

Display Systems of the Invention

The invention provides a new display system that is capable of multi-species eukaryotic display. More specifically, using the same display vector, without any molecular manipulations such as DNA digestions and cloning, a protein of interest can be displayed on the surface of multi-species such as yeast cells and mammalian cells, or expressed as a soluble protein in a eukaryotic host cells. The display systems of the invention utilize particular pairs of display vectors and helper vectors for each species. The different vector sets of the invention comprise a multi-species expression vector, encoding a library of polypeptide sequences fused to a first adapter (i.e. adapted), in combination with a helper vectors that is specific for particular genetic packages or host cell. Each of the helper vectors comprise a cell surface anchor protein fused to a second adapter (i.e., adapter2). As shown herein, the co-expression of a multi-species display vector in combination with a helper vector which comprises a corresponding adapter produces a collection of genetic packages (or host cells) which has a repertoire of polypeptide sequences displayed on its surface via the pairwise interaction of the adapters (i.e. adapter1 and adapter2).

Components of the Vectors

Adapters

Adapter sequences applicable for constructing the display and helper vectors of the subject display system can be derived from a variety of sources. Generally, any protein sequences involved in the formation of stable multimers are candidate adapter sequences. As such, these sequences may be derived from any homomultimeric or heteromultimeric protein complexes, Representative homomultimeric proteins are homodimeric receptors (e.g. plateletderived growth factor homodimer BB (PDGF), homodimeric transcription factors (e.g. Max homodimer, NF-kappaB p65 (RelA) homodimer), and growth factors (e.g. neurotrophin homodimers). Non-limiting examples of heteromultimeric proteins are complexes of protein kinases and SH2-domain-containing proteins (Cantley et al. (1993) *Cell* 72: 767 778; Cantley et al. (1995) *J. Biol. Chem.* 270(44): 26029 26032), heterodimeric transcription factors, and heterodimeric receptors. A vast number of heterodimeric receptors are known, including but not limited to receptors that bind to growth factors (e.g. heregulin), neurotransmitters (e.g. gamma.Aminobutyric acid), and other organic or inorganic small molecules (e.g. mineralocorticoid, glucocorticoid). Preferred heterodimeric receptors are nuclear hormone receptors (Belshaw et al (1996) *Proc. Natl. Acad. Sci. U.S.A* 93(10):4604 4607), erbB3 and erbB2 receptor complex, and G-protein-coupled receptors including but not limited to opioid (Gomes et al. (2000) *J. Neuroscience* 20(22): RC110); Jordan et al. (1999) *Nature* 399:697 700), muscarinic, dopamine, serotonin, adenosine/dopamine, and gamma-aminobutyric acid GABA families of receptors. Generally speaking, the majority of the known heterodimeric receptors, comprise C-terminal sequences that mediate heterodimer formation.

$GABA_B$-R1/$GABA_B$-R2 receptors exhibit the above-mentioned physical properties. These two receptors are essentially incapable of forming homodimers under physiological conditions (e.g. in vivo) and at physiological body temperatures, Research by Kuner et al. and White et al. (*Science* (1999) 283: 74 77); *Nature* (1998) 396: 679 682)) has demonstrated the heterodimerization specificity of $GABA_B$-R1 and $GABA_B$-R2 C-terminus in vivo. In fact, White et al. were able to clone $GABA_B$-R2 from yeast cells based on the exclusive specificity of this heterodimeric receptor pair. In vitro studies by Kammerer et al. (*Biochemistry*, 1999, 38: 13263-13269) has shown that neither $GABA_B$-R1 nor $GABA_B$-R2 C-terminal sequence is capable of forming homodimers in physiological buffer conditions when assayed at physiological body temperatures. Specifically, Kammerer et al. have demonstrated by sedimentation experiments that the heterodimerization sequences of $GABA_B$ receptor 1 and 2, when tested alone, sediment at the molecular mass of the monomer under physiological conditions and at physiological body temperatures. When mixed in equimolar amounts, $GABA_B$ receptor 1 and 2 heterodimerization sequences sediment at the molecular mass corresponding to the heterodimer of the two sequences (see Table I of Kammerer et al.). However, when the GABA$_B$-R1 and GABA$_B$ R2 C-terminal sequences are linked to a cysteine residue, homodimers may occur via formation of disulfide bond.

A diverse variety of coiled coils involved in multimer formation can be employed as the adapters in the subject display system. Preferred coiled coils are derived from heterodimeric receptors. Accordingly, the present invention encompasses coiled-coil adapters derived from GABA$_B$ receptors 1 and 2. In one aspect, the subject coiled coils adapters comprises a C-terminal sequences of GABA$_B$ receptor 1, referred to herein as GR1 EEKSRLLEKENRELEKIIAEKEERVSELRHQLQSVGGC (SEQ ID NO:10) and a sequence of GABA$_B$ receptor 2, referred to herein as GR2 TSRLEGLQSENHRLRMKITELDKDLEEVTMQLQDVGGC (SEQ ID NO:11).

It is to be understood that although the examples describe the use of vector sets which comprise the same pair of adapter sequences (referred to as adapter1 in the context of expression vectors and adapter2 in the context of helper display vectors), the vectors described herein can be prepared, and the methods of the invention can be practiced, using alternative adapters.

For example, based on the disclosure provided herein suitable adapter sequence can be derived from any of a number of coiled coil domains including for example Winzip-A2B1 (Katj a M Arndt et al, *Structure*, 2002, 10:1235-1248); Winzip-A1B1(Katja M Arndt et al, JMB, 2000, 295:627-639); FNfn1 O(Sanjib Dutta et al, *Protein Science*, 2005, 14:2838-2848), IAAL 15 E3/K3 (Jennifer R. Litowski and Robert S Hodges, JBC, 2002, 277(40) 37272-37279), PcrV/PcrG (Max Nanao et al, *BMC Microbiology*, 2003:1-9), bZip and derivatives (Jumi A. Shin, Pure Appl. Chem., 2004, 76(7-8): 1579-1590), ESCRT-III (David J. Gill et al, *The EMBO Journal*, 2007, 26:600-612), EE1234/RR1234 and derivatives (Johnthan R. Moll et al, *Protein Science*, 2001, 10:649-655), Laminin a, b, g, (Atsushi Utani et al, *JBC* 1995, 270(7):3292-3298), Peptides A/B and derivatives (Ilian Jelesarov and Hans Rudolf Bosshard, *JMB*, 1996, 263:344358), artificially designed peptides (Derek N. Woolfson and Tom Alber, *Protein Science*, 1995, 4:1596-1607), DcoH-HNF-p1 (Robert. B Rose et al, Nat. Struct. Biol., 2000, 7(9):744-748), and APC peptides (Catherine L. Day and Tom Alber, *JMB*, 2000, 301: 147-156).

Depending upon the affinity of the adapter subunit interaction associated with a particular pair of adapter subunits it may be possible to eliminate the need for using a disulfide bond to stabilize the resulting coiled coil interaction. For example, the affinities reported in the literature for some of the coiled coil domains listed above range from. 00001 nM to 70 nM (4.5 nM for Winzip-A2B1, 24 nM for Winzip-AIB1, 3 nM for FNfn10; 70 nM for 1 AL-E3/K3, 15.6 nM for PcrV/PcrG and 0.0001 nM for EE1234/RR1234 and derivatives).

Alternative heterodimeric transcription factors that are suitable for use as adapters include alpha-Pal/Max complexes and Hox/Pbx complexes Hox represents a large family of transcription factors involved in patterning the anterior-posterior axis during embryogenesis. Hox proteins bind DNA with a conserved three alpha helix homeodomain. In order to bind to specific DNA sequences, Hox proteins require the presence of hetero-partners such as the Pbx homeodomain. Wolberger et al. solved the 2.35 ANG. crystal structure of a Hox13I-Pbx1-DNA ternary complex in order to understand how Hox-Pbx complex formation occurs and how this complex binds to DNA. The structure shows that the homeodomain of each protein binds to adjacent recognition sequences on opposite sides of the DNA. Heterodimerization occurs through contacts formed between a six amino acid hexapeptide Nterminal to the homeodomain of HoxB1 and a pocket in Pbx1 formed between helix 3 and helices 1 and 2. A C-terminal extension of the Pbx1 homeodomain forms an alpha helix that packs against helix 1 to form a larger four helix homeodomain (Wolberger et al. (1999) *Cell* 96: 587 597; Wolberger et al. *J Mol Biol.* 291: 521 530).

For example, sequences from novel hetermultimeric proteins can be employed as adapters. In such situation, the identification of candidate sequences involved in formation of heteromultimers can be determined by any genetic or biochemical assays without undue experimentation. Additionally, computer modeling and searching technologies further facilitates detection of heteromultimeric sequences based on sequence homologies of common domains appeared in related and unrelated genes. Non-limiting examples of programs that allow homology searches are Blast, Fasta (Genetics Computing Group package, Madison, Wis.), DNA Star, Clustlaw, TOFFEE, COBLATH, Genthreader, and MegAlign. Any sequence databases that contains DNA sequences corresponding to a target receptor or a segment thereof can be used for sequence analysis. Commonly employed databases include but are not limited to GenBank, EMBL, DDBJ, PDB, SWISS-PROT, EST, STS, GSS, and HTGS.

Suitable adapters that are derived from heterodimerization sequences can be further characterized based on their physical properties. Preferred heterodimerization sequences exhibit pairwise affinity resulting in predominant formation of heterodimers to a substantial exclusion of homodimers. Preferably, the predominant formation yields a heteromultimeric pool that contains at least 60% heterodimers, more preferably at least 80% heterodimers, more preferably between 85 to 90% heterodimers, and more preferably between 90 to 95% heterodimers, and even more preferably between 96-99% heterodimers that are allowed to form under physiological buffer conditions and/or physiological body temperatures. In certain embodiments of the present invention, at least one of the heterodimerization sequences of the adapter pair is essentially incapable of forming a homodimer in a physiological buffer and/or at physiological body temperature. By "essentially incapable" is meant that the selected heterodimerization sequences when tested alone do not yield detectable amounts of homodimers in an in vitro sedimentation experiment as detailed in Kammerer et al. (1999) *Biochemistry* 38: 13263 13269), or in the in vivo two-hybrid yeast analysis (see e.g. White et al. *Nature* (1998) 396: 679 682). In addition, individual heterodimerization sequences can be expressed in a host cell and the absence of homodimers in the host cell can be demonstrated by a variety of protein analyses including but not limited to SDS-PAGE, Western blot, and immunoprecipitation. The in vitro assays must be conducted under a physiological buffer conditions, and/or preferably at physiological body temperatures. Generally, a physiological buffer contains a physiological concentration of salt and at adjusted to a neutral pH ranging from about 6.5 to about 7.8, and preferably from about 7.0 to about 7.5. A variety of physiological buffers is listed in Sambrook et al. (1989) supra and hence is not detailed herein. Preferred physiological conditions are described in Kammerer et al., (*Biochemistry*, 1999, 38: 13263-13269)

Adapters can be further characterized based on their secondary structures. Preferred adapters consist of amphiphilic peptides that adopt a coiled-coil helical structure. The helical coiled coil is one of the principal subunit oligomerization sequences in proteins. Primary sequence analysis reveals that approximately 2 3% of all protein residues form coiled coils (Wolf et al., (1997) *Protein Sci.* 6:1179 1189). Well-characterized coiled-coil-containing proteins include members of the cytoskeletal family (e.g. alpha.-keratin, vimentin), cytoskeletal motor family (e.g. myosine, kinesins, and dyneins), viral membrane proteins (e.g. membrane proteins of Ebola or HIV), DNA binding proteins, and cell surface receptors (e.g., $GABA_B$ receptors 1 and 2).

Coiled-coil adapters of the present invention can be broadly classified into two groups, namely the left-handed and right-handed coiled coils. The left-handed coiled coils are characterized by a heptad repeat denoted "abcdefg" with the occurrence of polar residues preferentially located at the first (a) and fourth (d) position. The residues at these two positions typically constitute a zig-zag pattern of "knobs and holes" that interlock with those of the other stand to form a tight-fitting hydrophobic core. In contrast, the second (b), third (c) and sixth (f) positions that cover the periphery of the coiled coil are preferably charged residues. Examples of charged amino acids include basic residues such as lysine, arginine, histidine, and acidic residues such as aspartate, glutamate, asparagine, and glutamine. Uncharged or polar amino acids suitable for designing a heterodimeric coiled coil include but are not limited to glycine, alanine, valine, leucine, isoleucine, serine and threonine. While the uncharged residues typically form the hydrophobic core, inter-helical and intra-helical salt-bridge including charged residues even at core positions may be employed to stabilize the overall helical coiled-coiled structure (Burkhard et al (2000) J. Biol. Chem. 275:11672-11677). Whereas varying lengths of coiled coil may be employed, the subject coiled coil adapters preferably contain two to ten heptad repeats. More preferably, the adapters contain three to eight heptad repeats, even more preferably contain four to five heptad repeats.

In designing optimal coiled-coil adapters, a variety of existing computer software programs that predict the secondary structure of a peptide can be used. An illustrative computer analysis uses the COILS algorithm which compares an amino acid sequence with sequences in the database of known two-stranded coiled coils, and predicts the high probability coiled-coil stretches (Kammerer et al. (1999) *Biochemistry* 38:13263 13269). Base on design and selection, a variety of engineered coiled coil sequences were reported, with affinity of nanomole to fentomole region (*Structure*, 2002, 10(9): 1235-48; *J Mol. Biol.* 2000, 21; 295(3):627-39; *Protein Sci.* 2005, 14(11):283848; *J* 13iol Chem. 2002, 277(40):37272-9; *BMC Microbiol.* 2003, 18:3:21; *Protein Science*, 2001, 10:649-655). For Example, engineered heterodimeric coiled coil sequences derived from human B-ZIP give a fentomole dissociate constant, which is similar to that for Biotin/Streptavidin interaction.

Another class of preferred coiled coil adapters are leucine zippers. The leucine zipper have been defined in the art as a stretch of about 35 amino acids containing 4 5 leucine residues separated from each other by six amino acids (Maniatis and Abel, (1989) *Nature* 341:24). The leucine zipper has been found to occur in a variety of eukaryotic DNA-binding proteins, such as GCN4, C/EBP, c-fos gene product (Fos), c jun gene product (Jun), and c-Myc gene product. In these proteins, the leucine zipper creates a dimerization interface wherein proteins containing leucine zippers may form stable homodimers and/or heterodimers. Molecular analysis of the protein products encoded by two proto-oncogenes, c-fos and c-jun, has revealed such a case of preferential heterodimer formation (Gentz et al., (1989) *Science* 243:1695; Nakabeppu et al., (1988) *Cell* 55:907; Cohen et al., (1989) *Genes Dev.* 3:173). Synthetic peptides comprising the leucine zipper regions of Fos and Jun have also been shown to mediate heterodimer formation, and, where the amino-termini of the synthetic peptides each include a cysteine residue to permit intermolecular disulfide bonding, heterodimer formation occurs to the substantial exclusion of homodimerization.

The leucine-zipper adapters of the present invention have the general structural formula known as the heptad repeat (Leucine-$X_1$—$X_2$—$X_3$—$X_4$—$X_5$—$X_6$)$_n$, where X may be any of the conventional 20 amino acids, but are most likely to be amino acids with alpha-helix forming potential, for example, alanine, valine, aspartic acid, glutamic acid, and lysine, and n may be 2 or greater, although typically n is 3 to 10, preferably 4 to 8, more preferably 4 to 5. Preferred sequences are the Fos or Jun leucine zippers.

Sequence of antibody chains that are involved in dimerizing the L and H chains can also be used as adapters for constructing the subject display systems. These sequences include but are not limited to constant region sequences of an L or H chain. Additionally, adapter sequences can be derived from antigen-binding site sequences and its binding antigen. In such case, one adapter of the pair contains antigen-binding site amino acid residues that is recognized (i.e. being able to stably associate with) by the other adapter containing the corresponding antigen residues.

The pairwise interaction between the first and second adapters may be covalent or non-covalent interactions. Non-covalent interactions encompass every exiting stable linkage that do not result in the formation of a covalent bond. Non-limiting examples of noncovalent interactions include electrostatic bonds, hydrogen bonding, Van der Waal's forces, steric interdigitation of amphiphilic peptides. By contrast, covalent interactions result in the formation of covalent bonds, including but not limited to disulfide bond between two cysteine residues, C—C bond between two carbon-containing molecules, C—O or C—H between a carbon and oxygen or hydrogen-containing molecules respectively, and 0-P bond between an oxygen- and phosphate-containing molecule.

Based on the wealth of genetic and biochemical data on vast families of genes, 5 one of ordinary skill will be able to select and obtain suitable adapter sequences for constructing the subject display system without undue experimentation.

Outer Surface Anchor Protein

For yeast display, suitable outer surface anchor proteins can be any of the outer wall proteins, with or without, GPI signal, which includes a-agglutinin (Aga1 and Aga2) Cwp1, Cwp2, Gas1p, Yap3p, Flo1p, Crh2p, Pir1, Pir2, Pir4, and imp in *S. cerevisiae*; HpSED1, HpGASI, HpTIP1, HPWPI in *Hansenula polymorpha*, and Hwp1p, Als3p, Rbt5p in *Candida albicans*. Alternatively, the methods of the invention can be practiced in the context of yeast using a cell surface anchor which is an artificial sequence that can be assembled into, or attached to the outer wall of yeast. As shown herein, Example 7 shows yeast display of scFv antibody by using helper vector pMAT7, or pMAT8, in which the yeast outer surface anchor protein is from Cwp2, or Aga2 depicted in FIGS. 4A and 4B.

Mammalian cell surface display can be practiced using a transmembrane domain of any known cell membrane proteins, or a polypeptides with GPI anchor sequences, or a noncleavable type 1 signal anchor sequences as a surface anchor. Alternatively, the methods of the invention can be practiced in the context of mammalian cells using a cell surface anchor which is an artificial sequence that can be assembled into, or attached to the cell membrane of mammalian cells. As shown herein, Example 11 shows the display of scFv protein on the mammalian cells by using helper vector pMAG2 (FIG. 8), in which the transmembrane domain of human EGF receptor fused to adapter2 is used as surface anchor for display.

Signal Sequences

Signal sequences from both prokaryotes and eukaryotes are built along the same general lines. They are about 15-30 amino acids in length and consist of three regions: a positively charged N-terminal region, a central hydrophobic region, and a more polar C-terminal region. There is a large amount of functional and structural homology between the signal peptides of prokaryotic and eukaryotic systems. Therefore, it is expected that some native signal peptides will function in both prokaryotes and eukaryotes.

Consistent with this expectation, some eukaryotic signal peptides have been reported to be functional in prokaryotic cells. For example, the signal peptide from human 10 growth hormone (hGH) and rat proinsulin protein function in *E. coli* (*Gene*, 1985, 39:247-254); yeast signal peptide of Endo-beta-1,3-glucanase are also functional in *E coli* (*Protein Exp. Puri*, 2000, 20.252-264). In addition, the prokaryotic signal peptides of *Staphlococcal* protein A, bacterial b-lactamase protein, and bacterial OmpA are functional in mammalian cells (Humphreys et al, *Protein Exp. Purif.* 2000, 20:252-264). Examples of signal peptides that work cross between yeast and mammalian cells are the signal peptides for human pancreatic lipase protein 1 (HPLRPI), human interferon, Human bile salt-stimulated lipase, and yeast *Saccharomyces cerevisiae* invertase (SUC2) (Tohoku *J Exp Med*, 1996, 180: 297-308; *Protein Exp. Puri*, 2006, 47:415-421; Protein Exp. Purif, 1998, 14:425-433).

Any of the native signal peptides including those identified above for their ability to function in a specific species may be used as signal peptides for the expression vector of this invention. In addition, an artificial signal peptide sequence characterized by the ability to function in eukaryotic host cells may also be used to practice the methods disclosed herein. The artificial signal peptides may be isolated from the design signal peptide libraries.

The vectors of the present invention generally comprise transcriptional or translational control sequences required for expressing the exogenous polypeptide. Suitable transcription or translational control sequences include but are not limited to replication origin, promoter, enhancer, repressor binding regions, transcription initiation sites, ribosome binding sites, translation initiation sites, and termination sites for transcription and translation.

The origin of replication (generally referred to as an ori sequence) permits replication of the vector in a suitable host cell. The choice of ori will depend on the type of host cells and/or genetic packages that are employed. Where the host cells are prokaryotes, the expression vector typically comprises two ori sequences, one directing autonomous replication of the vector within the prokaryotic cells, and the other ori supports packaging of the phage particles. Preferred prokaryotic ori is capable of directing vector replication in bacterial cells. Non-limiting examples of this class of ori include pMB1, pUC, as well as other *E. Coli* origins. Preferred ori supporting packaging of the phage particles includes but is not limited to f1 ori, Pf3 phage replication ori. For example, the pUC ori and f1 ori are built in the expression vectors in this invention for yeast and mammalian display.

In the eukaryotic system, higher eukaryotes contain multiple origins of DNA replication (estimated 10e4-10e6 ori/mammalian genome), but the ori sequences are not so clearly defined. The suitable origins for mammalian vectors are normally from eukaryotic viruses. Preferred eukaryotic ori includes but is not limited to SV40 ori, EBV ori, HSV oris. The suitable ori for yeast cells includes but is not limited to 2u ori CEN6/ARS4 ori.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters will often, but not always, contain "TATA" boxes and "CAT" boxes.

The choice of promoters will largely depend on the host cells in which the vector is introduced. For prokaryotic cells, a variety of robust promoters are known in the art. Preferred promoters are lac promoter, Trc promoter, T7 promoter and pBAD promoter. Normally, to obtain expression of exogenous sequence in multiple species, the prokaryotic promoter can be placed immediately after the eukaryotic promoter, or inside an intron sequence downstream of the eukaryotic promoter.

Suitable promoter sequences for other eukaryotic cells include the promoters for 3-phosphoglycerate kinase, or other glycolytic enzymes, such as enolase, glyceraldehyde-3phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Preferred promoters for mammalian cells are SV40 promoter, CMV promoter, β-actin promoter and their hybrids. Preferred promoter for yeast cell includes but is not limited to GAL 10, GAL I, TEFI in *S. cerevisia*, and GAP, AOX1 in *P. pastoris*.

In constructing the subject vectors, the termination sequences associated with the exogenous sequence are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various yeast transcriptional termination sequences or mammalian polyadenylation sequences that are known in the art, widely available, and exemplified below. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, zeocin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In one embodiment of the invention, the expression vector is a shuttle vector, capable of replicating in at least two unrelated host systems. In order to facilitate such replication, the vector generally contains at least two origins of replication, one effective in each host system. Typically, shuttle vectors are capable of replicating in a eukaryotic host system and a prokaryotic host system. This enables detection of protein expression in the eukaryotic host (the expression cell type) and amplification of the vector in the prokaryotic host (the amplification cell type). Preferably, one origin of replication is derived from SV40 or 2u and one is derived from pUC, although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized In one embodiment of the invention, the expression vector comprises more than one expression cassettes for multi-chain protein complex. Each cassette comprises promoter, signal sequence, gene of interest, and transcription termination sequence. To display multi-chain complex on the eukaryotic cell surface, at lease one of the expression cassettes will express adapter1 fusion with one chain of the multi-chain complex. For example, to display full length antibody or antibody Fab fragment (heavy chain and light chain), at least one expression cassette will express adapter1 fusion with either heavy chain or light chain. Alternatively, yeast mating system can be used for display of multi-chain complex. The expression cassettes for multi-chains can be split into two expression vectors. The first expression vector can be introduced into one mating type MATa strain, second vector will be induced into another mating type MATα strain. The two vectors will be brought together in a single diploid by yeast mating. For display, at least one expression vector comprises at least one express cassette for adapter1 fusion with one chain of the multi-chain complex.

The vectors encompassed by the invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art. Additionally, using well-known restriction and ligation techniques, appropriate sequences can be excised from various DNA sources and integrated in operative relationship with the exogenous sequences to be expressed in accordance with the present invention.

The examples and figures provided with this disclosure illustrate practice of the present invention in multi-species display of protein of interest on the eukaryotic systems. The following examples are meant to be illustrative of an embodiment of the present invention and should not limit the scope of the invention in any way. A number of modifications and variations will be apparent to the skilled artisan from reading this disclosure. Such modifications and variations constitute part of the invention.

The practice of the present invention employs, unless otherwise indicated, conventional techniques of cell biology, molecular biology, cell culture and the like which are in the skill of one in the art. All publications and patent applications cited in the specification are indicative of the level of skill of those skilled in the art to which this invention pertains and are hereby incorporated by reference in their entirety.

Although the various compositions and methods of the invention (multi-species and cross-species display strategies) of the invention are exemplified herein using a coding sequence for an anti-VEGF antibody, a skilled artisan will readily appreciate that libraries of expression cassettes encoding diverse libraries of antibody sequences can be used in the expression and display vector sets of the invention to accomplish antibody discovery and engineering protocols.

The practice of the present invention will employ, unless otherwise indicated, conventional techniques of immunology, biochemistry, chemistry, molecular biology, microbiology, cell biology, genomics and recombinant DNA, which are within the skill of the art. See, e.g., PHAGE DISPLAY OF PEPTIDES AND PROTEINS (B. K. Kay et al., 1996); PHAGE DISPLAY, A LABORATORY MANUAL (C. F. Barbas III et al., 2001) Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR. 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Further illustration of the development and use of subject vectors, display systems and host cells are provided in the EXAMPLES section below. The examples are provided as a guide to a practitioner of ordinary skill in the art, and are not meant to be limiting in any way.

EXAMPLES

Example 1

Construction Yeast Expression Vector pMAT9 pMAT9 vector (FIG. 2A) comprise a expression cassette for an anti-VEGF scFv antibody fused with adapter1 (GR1) (SEQ ID NO:1) and detectable HA and His6 tag (DH tag). It was constructed by insertion of a fully synthetic gene fragment into a commercial pESC-TRP vector (Stratagene) through cloning sites EcoRI and PacI. The scFv-GR1 fusion protein is under the control of a galactose-induced promoter GAL10 and a signal sequence of yeast endo-beta-1,3-glucanase (Bgl2). The fusion gene sequence (SEQ ID NO:3) was confirmed by standard DNA sequencing method.

Example 2

Figure 2B:
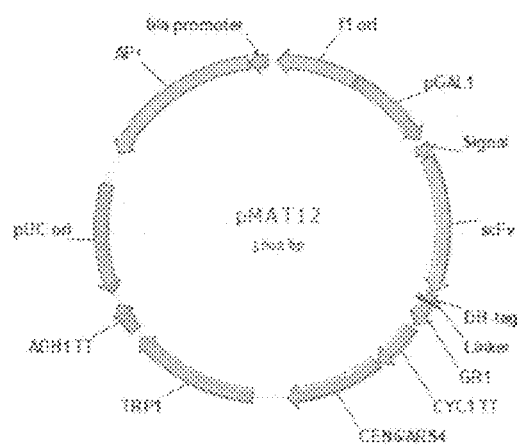

Construction Yeast Expression Vector pMAT12 pMAT12 (SEQ ID NO: 4) provides an expression vectors that is suitable for expression in yeast cells. As shown in FIG. 2B, pMAT12 is created on the backbone of commercial vector pUC 19 by insertion at AatII and PciI sites with a fully synthetic DNA fragment (Codon Devices). This fully synthetic DNA fragment comprises (1) fl ori; (2) a expression cassette for the adapter GR1 (SEQ ID NO:1) fusion, which is driven by a yeast pGAL1 promoter. The sequence of anti-VEGF scFv antibody is built in the downstream of a yeast signal sequence (yeast endo-B-1,3-glucanase protein Bgl2p). The HA-His6 tag (DH-tag) sequences are upstream of GR1 sequence for protein detection and Ni-NTA purification. (3) yeast CEN/ARS ori for replication; and (4) a expression cassette for yeast TRP1 auxotrophic marker. The synthetic DNA sequence was confirmed by standard DNA sequencing method.

Example 3

Figure 3A:
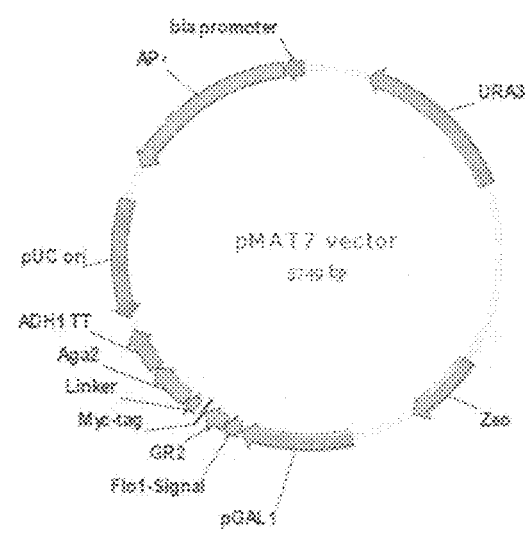
FIGS. 3A and 3B provide schematic representations of the yeast helper display vectors pMAT7 (FIG. 3A) and pMAT8 (FIG. 3B).

Yeast Helper Vector pMAT7 pMAT7, which is graphically depicted in FIG. 3A, is another yeast display helper vector which expresses a fusion protein comprising the yeast outer surface protein Aga2 in frame with adapter 2 (GR2) (SEQ ID NO: 2). This vector was created from the yeast helper vector pMAT3 by replacing BamHI-HindIII fragment with a synthetic DNA fragment of 208 bp. This synthetic DNA comprises the sequence encoding yeast out well protein Aga2. Using BioFab platform technology of Codon Devices, the errors generated from oligo synthesis were corrected by oligo selection with sequences complementary to the synthetic genes, and affinity purification of Mut-S protein column. The nucleotide sequence of pMAT7 (SEQ ID NO: 5) was confirmed by standard DNA sequencing.

Example 4

Construction of Yeast Helper Vector pMAT8

Figure 3B:
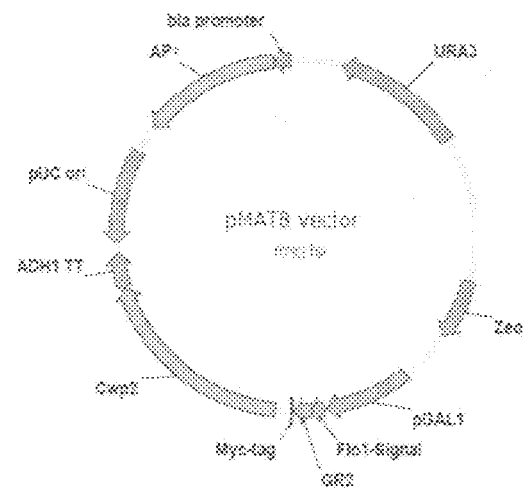

The vector pMAT8 shown in FIG. 3B is yeast helper vector, which expresses a fusion protein of adapter 2 with yeast out surface GPI anchoring protein Cwp2. This vector was constructed on the backbone of commercial vector pUC19 by insertion at AatII and PciI sites with a fully synthetic DNA fragment. This fully synthetic DNA comprises sequences for three expression cassettes: (1) yeast URA3 selection marker; (2) Zeocin marker for yeast selection; (3) adapter GR2 fusion with yeast out well protein Cwp2 and Flo1 SIT rich region, under control of yeast pGAL1 promoter and the secretory signal sequence of Flo1. Using BioFab platform technology of Codon Devices at Boston, the errors in synthetic DNA was corrected by oligo selection with sequences complementary to the synthetic genes, and affinity purification of Mut-S protein column. The nucleotide sequence of pMAT8 (SEQ ID NO: 6) was confirmed by standard DNA sequencing.

Example 5

Yeast Strain with a Chromosomal Integrant of Yeast Helper Vector pMAT7

Figure 4:
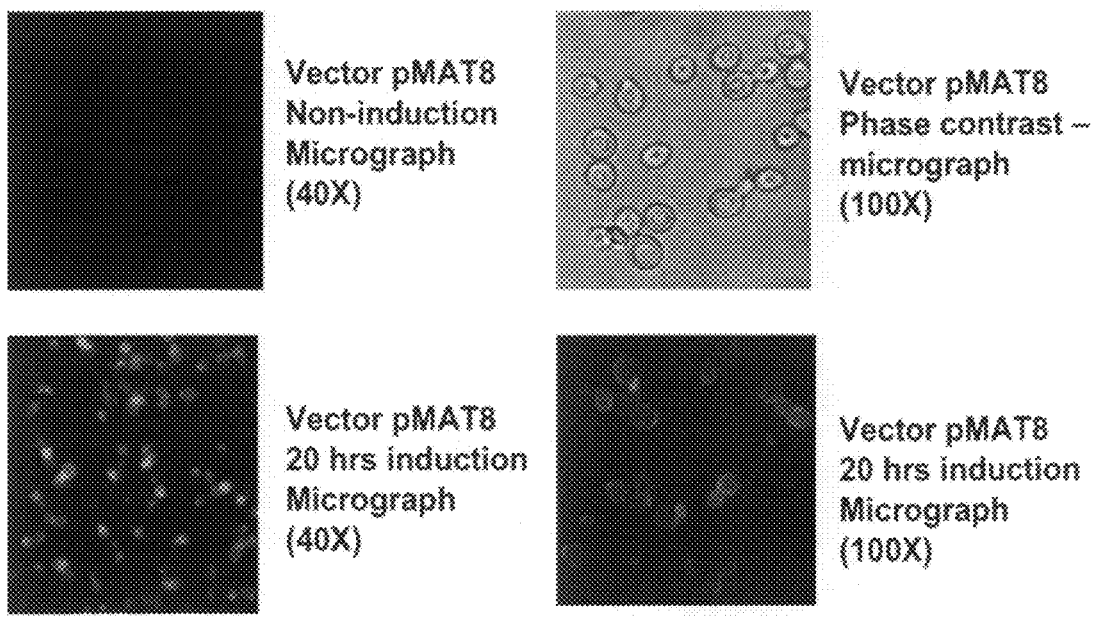
FIG. 4 provides a series of micrograph images of yeast cells transfected with a yeast helper vector comprising an adapter2 sequences fused to the outer cell membrane protein Cwp2. Yeast cells comprising a chromosomal integrant of the yeast helper vector pMAT8 were stained with mouse anti-Myc antibody and Alexa-488 conjugated anti-mouse antibody. The control micrograph presented in panel (a) shows a lack of fluorescence by cells that are not induced. The fluorescence micrograph presented in panel (b) shows a fluorescent signal on the surface of induced yeast cells. Panel (c) provides a phase contrast micrograph of the same cells depicted in the fluorescence micrograph of provided in panel (d). The surface fluorescence (green signal) detected in panel (d) illustrates the surface expression of Myc-tagged adapter2 fusion proteins anchored to the outer wall of induced yeast cells.

Vector DNA of pMAT7 was first linearizd with restriction enzyme ApaI, then transformed into yeast S. cerevisiae strain YPH499 (Stratagene) using Frozen-EZ Yeast Transformation II Kit according to Zymo Research's instruction. Clones with pMAT7 integration was selected and grown on the CM glucose minus URA plate (Teknova). In order to test the surface expression of adapter 2 (GR2) fusion protein in yeast cells carrying pMAT7 vector, the Galactose induction experiment was performed. Briefly, cells from single colony were grown in 50 ml of YDP medium at 30° C. overnight (OD600=15~20), thus transferred to 50 ml SG-CAA-minus URA medium (20 g/L galactose, 6.7 g/L yeast nitrogen base, 5 g/L Casamino Acids/-URA, 10.19 g/L $Na_2HPO_4.7H_2O$, 8.56 g/L $NaH_2PO_4.H_2O$) for 48 hrs growth at 25° C. to 10-15 OD600. The cells were harvested, washed with PBS, and incubated with mouse monoclonal anti-myc antibody (Upstate Biotechnologies) for 1 hr at room temperature. The PBS-washed cells were then probed with Goat anti-mouse-Alexa 488 (invitrogen) for 30 min in the dark. After PBS wash, fluorescent labeled GR2 fusion protein on the yeast cell surface was visualize under a Zeiss Axiovert 135 fluorescent microscope with Plan-Neofluar X40/0.75 Ph2 and X100 oil objective lens. FIG. 4A showed clear surface localization of myc-tagged GR2-Aga2 fusion in green fluorescence, demonstrating the functional cell surface expression of adapter2 fusion by yeast helper vector pMAT7.

Example 6

Yeast Strain with a Chromosomal Integrant of Yeast Helper Vector pMAT8

The procedure of generation yeast stain with chromosomal integration of pMAT8 vector was similar as described Example 5, except only 20 hours induction for adapter 2 fusion expression. Briefly, PMAT8 vector DNA was linearizd with restriction enzyme ApaI, and transformed into yeast S. cerevisiae strain YPH499 (Stratagene). Clones with pMAT8 integration was selected and grown on the CM glucose minus URA plate (Teknova). To test the surface expression of adapter 2 (GR2)-Cwp2 fusion protein in yeast cells carrying pMAT8 vector, the Galactose induction experiment was performed. Briefly, cells from single colony were grown in 50 ml of YDP medium at 30° C. overnight. (OD600=15~20), thus transferred to 50 ml SG-CAA-minus URA medium (20 g/L galactose, 6.7 g/L yeast nitrogen base, 5 g/L Casamino Acids/-URA, 10.19 g/L $Na_2HPO_4.7H_2O$, 8.56 g/L $NaH_2PO4.H_2O$) for 20 hrs growth at 25° C. to 10~15 OD600. The cells were harvested, washed with PBS, and incubated with mouse monoclonal anti-myc antibody (Upstate Biotechnologies) for 1 hr at room temperature. The PBS-washed cells were then probed with Goat anti-mouse-Alexa 488 (invitrogen) for 30 min in the dark. After PBS wash, fluorescent labeled GR2 fusion protein on the yeast cell surface was visualize under a Zeiss Axiovert 135 fluorescent microscope with Plan-Neofluar X40/0.75 Ph2 and X100 oil objective lens. FIG. 4B showed clear surface localization of myc-tagged GR2-Cwp2 fusion in green fluorescence, demonstrating the functional cell surface expression of adapter2 fusion by yeast helper vector pMAT8. In comparison with pMAT7, vector pMAT8 produced higher density of adapter 2 fusion on yeast surface after 20 hours induction.

Example 7

Yeast Surface Display of scFv Antibody Proteins by Using Expression Vector pMAT9 or pMAT12, with Helper Vector pMAT8

Figure 5A:
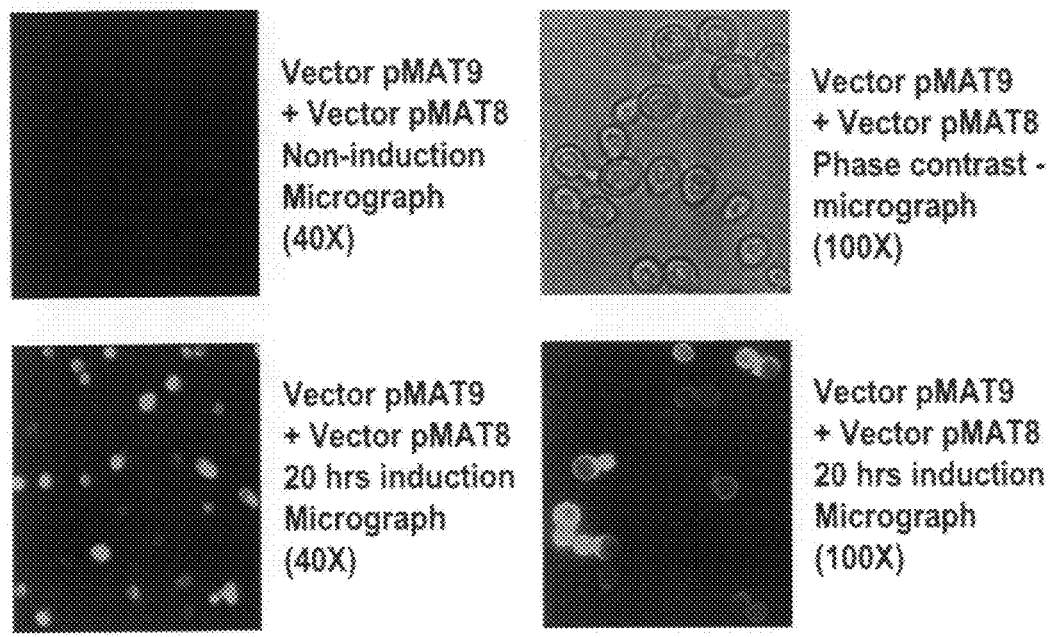
FIGS. 5A through 5C illustrates the functional surface display of scFv antibody on yeast cells comprising the pMAT9 and pMAT12 display vectors.
Figure 5B:
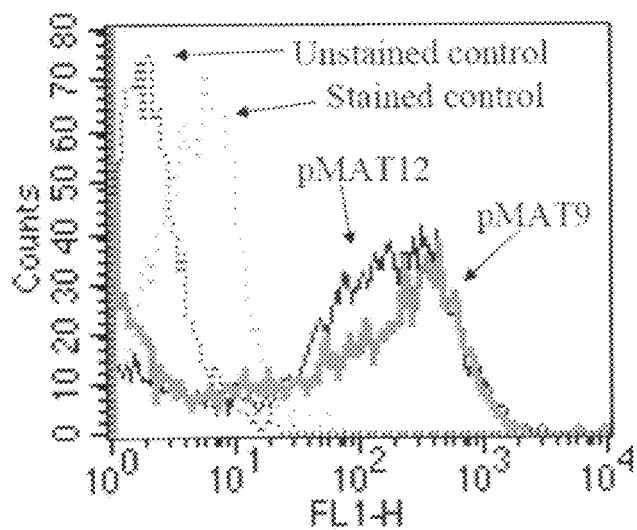

The yeast strain with chromosomal integration of pMAT8 vector was used for yeast surface display of antibody. The expression vector pMAT9 or pMAT12 was transformed into YPH499-pMAT8 strain created from Example 6 according to the protocol of Frozen-EZ Yeast Transformation II Kit (Zymo Research). Cells from a single colony on CM glucose minus TRP & URA plate (Teknova) were grown in the 50 ml SD- CAA-minus TRP & URA medium (20 g/L Dextrose, 6.7 g/L yeast nitrogen base, 5 g/L Casamino Acids/-URA, 10.19 g/L $Na_2HPO_4.7H_2O$, 8.56 g/L $NaH_2PO4.H_2O$) overnight at 30° C. (OD600=15-20), thus transferred to 50 ml SG-CAA-minus TRP & URA medium for 20 hrs growth at 25° C., to induce the expression of scFv-DH-GR1 fusion from expression vector and expression of GR2-Myc-GR2 from helper vector. The cells were harvested, washed with PBS, and incubated with mouse monoclonal anti-HA antibody (Santa Cruz Biotechnologies) for 1 hr at room temperature. The PBS-washed cells were then probed with Goat anti-mouse-Alexa 488 (invitrogen) for 30 min in the dark. After PBS wash, fluorescent labeled scFv-DH-GR1 fusion protein on the yeast cell surface was visualize under a Zeiss Axiovert 135 fluorescent microscope. FIG. 5A showed clear surface localization of HA-tagged scFv in green fluorescence, demonstrating the say display on yeast cell surface by using pMAT9 vector. In addition, the fluorescence associated with scFv displayed on cell surface was also measured in FACS Cailibur flow cytometry. The FACScan results in FIG. 5B showed a peak of ~70-80% positive cells with high fluorescence intensity, and there was no significant difference on the display level between vector pMAT9 (with high copy replication ori) and pMAT12 (with low copy replication ori).

Figure 5C:
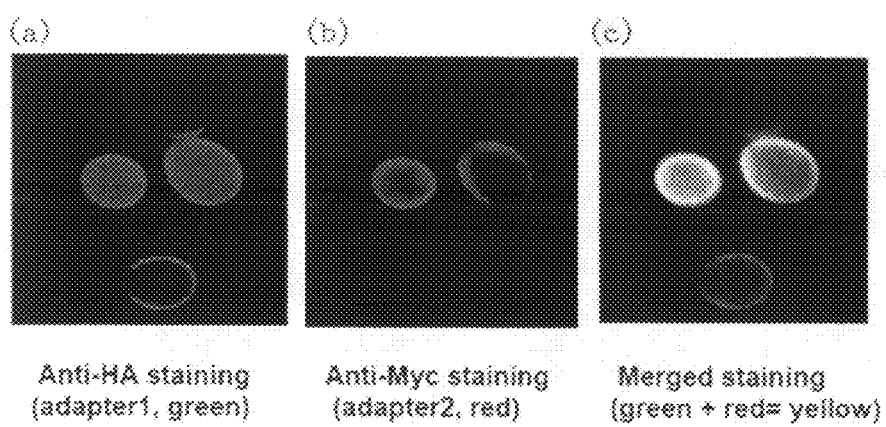

Furthermore, in order to show the interaction of adapter1 and adapter2 on yeast cell surface, the post-induction cells (using pMAT9 vector) were incubated with rat anti-HA antibodies (Roche) plus mouse anti-myc antibodies (Upstate Biotechnologies) for 60 min to probe both adapters. Cells were washed three times with PBS and incubated with Alexa 488 conjugated chicken anti-rat antibody antibody plus Alex 594 conjugated goat anti-mouse antibody (Invitrogen) in PBS for 60 min. After three times washing with PBS, cells on slides were observation under a Zeiss Axiovert 200M microscope with Plan-Neofluar X40/0.75 Ph2 and X100 oil objective lens. The results in FIG. 5C showed clear surface localization of HA-tagged adapter I (GR1) in green fluorescence, myc-tagged adapter 2 (GR2) on surface in red fluorescence. The yellow fluorescence merged from green and red fluorescence indicated the co-localization of both adapters on the cell surface, confirmed the surface display mechanism through adapter interaction.

Example 8

Yeast Expression Vector pMAT19 for Surface Display of Fab Antibody

Figure 6:
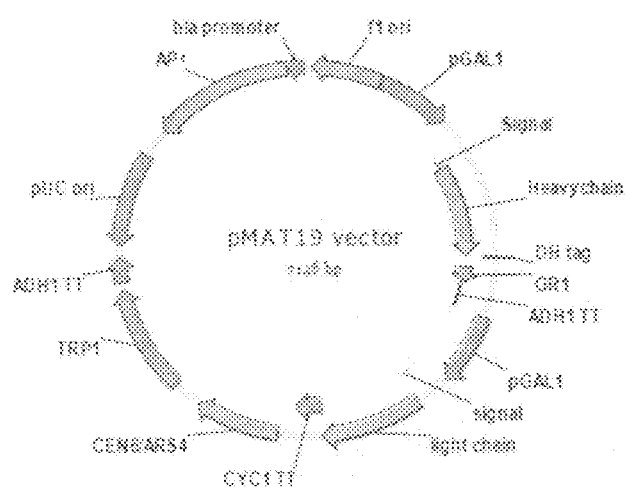
FIG. 6 provides a graphic representation of the yeast expression vector pMAT19 which comprises two expression cassettes, one for adapter1 fusion to heavy chain, and a second cassette for a light chain, and is suitable for the display of a library comprising a repertoire of Fab-formatted antibodies.

Vector pMAT19 (FIG. 6, SEQ ID NO:7) was derived from pMAT12 vector. It was created on the backbone of pMAT12 by insertion after pGAL1 promoter at Aatll and SacII sites with a fully synthetic DNA fragment (Codon Devices). This fully synthetic DNA fragment comprises (1) yeast endo-B-1, 3-glucanase signal sequence-heavy chain of anti-IL13R Fab antibody-HA tag-GR1 adapter-ADH terminator; (2) an expression cassette for the light chain of anti-IL13R Fab, which is driven by a yeast pGAL1 promoter, and yeast endo-B-1,3-glucanase signal. The synthetic DNA sequence was confirmed by standard DNA sequencing method.

Example 9

Construction of Mammalian Expression Vector pMAG10

The vector pMAG10 is a mammalian expression vector to produce soluble adapter1 fusion in mammalian cells. The elements of the pMAG10 vector as depicted in the schematic representation provided in FIG. 7. The vector was built on the backbone of commercial vector pUC19 by insertion at EcoRI and PciI sites with a fully synthetic DNA fragment. This fully synthetic DNA comprises the following elements: (1) fl ori for phage package; (2) an expression cassette, in which the expression of the adapter GR1 fusion with a scFv is driven by a CMV enhancer/Chicken β-actin promoter. The HA-His6 tag (DH-tag) sequences are upstream of GR1 sequence for protein detection and Ni-NTA purification. (3) an expression cassette for mammalian selection marker neomycin. The synthetic DNA was generated by fully gene synthesis using Codon Devices BioFab platform technology at Boston. The errors generated from gene synthesis were corrected by oligo selection with sequences complementary to the synthetic genes, and affinity purification of Mut-S protein column. The nucleotide sequence of pMAG10 (SEQ ID NO: 8) was confirmed by standard DNA sequencing method.

Example 10

Construction of Mammalian Helper Vector pMAG2

The mammalian helper vector pMAG2 (FIG. 8) was created on the backbone of commercial vector pUC19 by insertion at EcoRI and PciI sites with a fully synthetic DNA fragment of 3134 bp. This fully synthetic DNA comprises sequences for two expression cassettes: (1) Zeocin expression cassette, with SV40 ori/promoter and SV40 polyA; (2) adapter GR2 fusion with transmembrane domain of human epidermal growth factor receptor (hEGFR), driven by a CMV promoter and terminated by BGH polyA. The secretory signal sequence for adapter GR2 fusion is from hEGFR. The gene synthesis was briefly described below. The synthetic DNA was divided into 4 pieces of segments of 808, 790, 829, and 817 by for gene synthesis by using BioFab platform technology (Codon Devices). The errors generated from oligo synthesis were corrected by oligo selection with sequences complementary to the synthetic genes, and affinity purification of Mut-S protein column. These DNA with tag sequences containing type II restriction sites were digested and ligated into full DNA fragment, which was then cloned into pUC19 vector. The nucleotide sequence of pMAG2 (SEQ ID NO:9) was confirmed by standard DNA sequencing method.

Example 11

Adapter-directed Mammalian Cell Surface Display

COS 6 cells were grown on coverslips in 6-well plates with Dulbecco's modified Eagle's medium supplemented with 10% fetal bovine serum, 100 units/ml penicillin G, 100 µg/ml streptomycin, pAMG10 expression vector and mammalian helper vector pMAG2 were co-transfected into COS 6 cells using FuGene 6 transfection reagent (Roche Applied Science) according to the manufacturer's instructions. Briefly, 800 ng of plamid DNA (400 ng of pMAG10+400 ng of pMAG2) was added to diluted FuGENE 6 reagent at 3:2 ratio of FuGene 6 reagent (ul):DNA complex (ug) in serum-free medium. The FuGENE reagent DNA complex was incubated for 15 min at room temperature and then added to the cells. After 48 hr of transfection, HA tagged scFv –GR1 fusion protein (from pMAG10 vector) and myc tagged GR2-EGFR-TM displayed on the cell surface were detected with anti-HA and anti-Myc antibody, then labeled with Alexa 488 and Alex 594.

Briefly, COS 6 cells were fixed with 4% formaldehyde for 20 min, blocked with 5% BSA in PBS for 30 min at 25° C. and then incubated with rat anti-HA antibodies (Roche) plus mouse anti-myc antibodies (Upstate Biotechnologies) for 60 min to probe both adapters. Cells were washed three times with PBS and incubated with Alexa 488 conjugated chicken anti-rat antibody antibody plus Alex 594 conjugated goat anti-mouse antibody (Invitrogen) in PBS for 60 min. After three times washing with PBS, cells on slides were observation under a Zeiss Axiovert 200M microscope with Plan-Neofluar×40/0.75 Ph2 and X100 oil objective lens. Panel 9 presents photomicrographs that illustrate the surface expression and co-localization of the fusion proteins on the surface of the host cells. As a negative control, wild-type COS 6 cells that were not transfected with either a display vector or a helper vector of the invention were stained with the same fluorochromes. No cell surface fluorescence was detected on any of the negative control samples.

Figure 9:
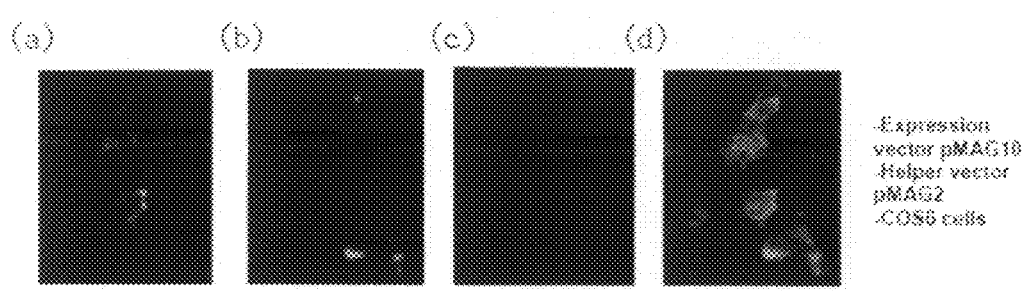
FIG. 9 provides the fluorescence microscopy images of COS 6 cells displaying HA-tagged anti-VEGF scFv antibodies on their surface. The COS 6 cells depicted in the upper row of images (panels a-d) were transfected with the display vector pMAG10 and helper vector pMAG2. The surface expression of HA-tagged scFv-adapter1 fusion proteins on the plasma membrane of the co-transfected COS 6 cells depicted in panel (a) by a (green) fluorescent signal. The co-localization of the myc-tagged adapter2 fusion proteins on the surface of the COS 6 cells is depicted in panel (b) by a red fluorescent signal. The co-localization of the display vector Adapter 1 fusion protein and the helper vector plasma membrane Adapter2 fusion protein can be detected by the presence of a third color fluorescent signal, such as the yellow to orange fluorescent signal depicted in panel d) resulting from the merger of the green and red fluorescent signals contributed by the display vector and helper vector fusion proteins. The cells depicted in panel (c) were stained with a nuclear stain.

The photomicrographs presented in panel (a) of FIG. 9 demonstrates the plasma membrane localization of HA-tagged adapter1 (GR1) fusion proteins as green fluorescence. Panel (b) of FIG. 9 demonstrates the plasma membrane localization of myc-tagged adapter2 (GR2) fusion protein which was detected as red fluorescence on the surface of the COS 6 cells. The cells in panel (c) of FIG. 9, which are devoid of fluorescence were stained with nuclear stain. Panel (d) of FIG. 9 demonstrates the co-localization of the two fusion proteins on the plasma membrane of the COS 6 cells. Detection of the co-localization of the two adapter tagged fusion proteins can be detected by the presence of cells displaying a third color fluorescent signal (using the fluorochromes described in this example the third fluorescent signal will be a yellowish-orange color). For example, the co-localization signal depicted in panel (d) results from the merger of the two other fluorescent signals used to detect the surface expression of each of the other fusion proteins.

REFERENCES

1) George Smith, Science (1985) 228: 1315-1317
2) U.S. Pat. No. 5,969,108
3) U.S. Pat. No. 5,837,500
4) Crameri, et al. (1993) Gene 137:69 75
5) WO 01/05950, U.S. Pat. No. 6,753,136, (Cis-display)
6) U.S. Pat. No. 7,175,983, (Adapter-directed display system)
7) Chang H H, Lo S J (2000) Modification with a phosphorylation tag of PKA in the TraT-based display vector of *Escherichia coli*. J Biotechnol 78:115-122
8) Lee S H, Choi J I, Park S J, Lee S Y, Park B C (2004) Display of bacterial lipase on the *Escherichia coli* cell surface by using FadL as an anchoring motif and use of the enzyme in enantioselective biocatalysis. Appl Environ Microbiol 70:5074-5080
9) Westerlund-Wikström B et al (1997) Functional expression of adhesive peptides as fusions to *Escherichia coli* flagellin. Protein Eng 10:1319-1326
10) Georgiou G, Stephens D L, Stathopoulos C, Poetschke H I, Mendenhall J, Earhart C F (1996) Display of β-lactamase on the *Escherichia coli* surface: outer membrane phenotypes conferred by Lpp'-OmpA'-β-lactamase fusions. Protein Eng 9: 239-247
11) Jung H C et al (1998) Surface display of *Zymomonas mobilis* levansucrase by using the ice-nucleation protein of *Pseudomonas syringae*. Nat Biotechnol 16:576-580
11) Veiga E et al (2003) Autotransporters as scaffolds for novel bacterial adhesins: surface properties of *Escherichia coli* cells displaying Jun/Fos dimerization domains. J Bacterial 185:5585-5590
12) Schreuder M P, Brekelmans S, Van den Ende H, Klis F M (1993) Targeting of a heterologous protein to the cell wall of *Saccharomyces cerevisiae*. Yeast 9:399-409
13) U.S. Pat. Nos. 6,300,065, 6,423,538, 6,696,251, and 6,699,658
14) Georgiou G et al (1997) Display of heterologous proteins on the surface of microorganisms: from the screening of combinatorial libraries to live recombinant vaccines. Nat Biotechnol 15:29-34
15) Ashiuchi M, Misono H (2002) Biochemistry and molecular genetics of poly-γ-glutamate synthesis. Appl Microbiol Biotechnol 59:9-14
16) Ashiuchi M, Nawa C, Kamei T, Song J J, Hong S P, Sung M H, Soda K, Yagi T, Misono H (2001) Physiological and biochemical characteristics of poly γ-glutamate synthetase complex of *Bacillus subtilis*. Eur J Biochem 268:5321-5328
17) Benhar I (2001) Biotechnological applications of phage and cell display. Biotechnol Adv 19:1-33
18) Dubois M, Gilles K A, Hamilton J K, Rebers P A, Smith F (1956) Colorimetric method for determination of sugars and related substances. Anal Chem 28:350-356
19) Georgiou G, Stathopoulos C, Daugherty P S, Nayak A R, Iverson B L, Curtiss R III (1997) Display of heterologous proteins on the surface of microorganisms: from the screening of combinatorial libraries to live recombinant vaccines. Nat Biotechnol 15:29-34
20) Jose J, von Schwichow S (2004) Autodisplay of active sorbitol dehydrogenase (SDH) yields a whole cell biocatalyst for the synthesis of rare sugars. Chembiochem 5:491-499
21) Jose J, Bernhardt R, Hannemann F (2002) Cellular surface display of dimeric Adx and whole cell P450-mediated steroid synthesis on *E. coli*. J Biotechnol 95:257-268
22) Jung H C, Lebeault J M, Pan J G (1998) Surface display of *Zymomonas mobilis* levansucrase by using the ice-nucleation protein of *Pseudomonas syringae*. Nat Biotechnol 16:576-580
23) Kaieda M, Nagayoshi M, Hama S, Kondo A, Fukuda H (2004) Enantioselective transesterification using immobilized *Aspergillus oryzae* overexpressing lipase. Appl Microbiol Biotechnol 65:301-305
24) Kano K, Negi S, Kawashima A, Nakamura K (1997) Optical resolution of 1-arylethanols using transesterification catalyzed by lipases. Enantiomer 2:261-266
24) Lee S Y, Choi J H, Xu Z (2003) Microbial cell-surface display. Trends Biotechnol 21:45-52
25) Lee S H, Choi J I, Park S J, Lee S Y, Park B C (2004) Display of bacterial lipase on the *Escherichia coli* cell surface by using FadL as an anchoring motif and use of the enzyme in enantioselective biocatalysis. Appl Environ Microbial 70:5074-5080
26) Lee S H, Choi J I, Han M J, Choi J H, Lee S Y (2005) Display of lipase on the cell surface of *Escherichia coli* using OprF as an anchor and its application to enantioselective resolution in organic solvent. Biotechnol Bioeng 90:223-230
27) Matsumoto T, Ito M, Fukuda H, Kondo A (2004) Enantioselective transesterification using lipase-displaying yeast whole-cell biocatalyst. Appl Microbiol Biotechnol 64:481-485

28) Narita J, Nakahara S, Fukuda I-I, Kondo A (2004) Efficient production of L-(+)-lactic acid from raw starch by *Streptococcus bovis* 148. J Biosci Bioeng 97:423-425
28) Poo H, Song J J, Hong S P, Choi Y H, Yun S W, Kim J H, Lee S C, Lee S G, Sung M H (2002) Novel high-level constitutive expression system, pHCE vector, for a convenient and cost-effective soluble production of human tumor necrosis factor-α. Biotechnol Lett 24:1185-1189
29) Richins R D, Kaneva I, Mulchandani A, Chen W (1997) Biodegradation of organophosphorus pesticides by surface-expressed organophosphorus hydrolase. Nat Biotechnol 15:984-987
30) Robyt J F, Whelan W J (1972) Reducing value methods for maltodextrins. I. Chain-length dependence of alkaline 3,5-dinitrosalicylate and chain-length independence of alkaline copper. Anal Biochem 45:510-516
31) Satoh E, Niimura Y, Uchimura T, Kozaki M, Komagata K (1993) Molecular cloning and expression of two α-amylase genes from *Streptococcus bovis* 148 in *Escherichia coli*. Appl Environ Microbiol 59:3669-3673
32) Shigechi H, Koh J, Fujita Y, Matsumoto T, Bito Y, Ueda M, Satoh E, Fukuda H, Kondo A (2004) Direct production of ethanol from raw corn starch via fermentation by use of a novel surface-engineered yeast strain codisplaying glucoamylase and α-amylase. Appl Environ Microbial 70:5037-5040
33) Sung M H, Hong S P, Lee J S, Jung C M, Kim C J, Soda K, Ashiuchi M (2003) Surface expression vectors having pgsBCA, the gene coding poly-gamma-glutamate synthetase, and a method for expression of target protein at the surface of microorganism using the vector. International Patent WO 03/014360
34) Uppenberg J, Hansen M T, Patkar S, Jones T A (1994) The sequence, crystal structure determination and refinement of two crystal forms of lipase B from *Candida antarctica*. Structure 2:293-308
35) Veiga E, de Lorenzo V, Fernandez L A (2003) Autotransporters as scaffolds for novel bacterial adhesins: surface properties of *Escherichia coli* cells displaying Jun/Fos dimerization domains. Bacteriol 185:5585-5590
36) von Heijne G (1986) A new method for predicting signal sequence cleavage sites. Nucleic Acids Res 14:4683-4690
37) Wan H M, Chang B Y, Lin S C (2002) Anchorage of cyclodextrin glucanotransferase on the outer membrane of *Escherichia coli*. Biotechnol Bioeng 79:457-464

What is claimed is:

1. A method for displaying a repertoire of polypeptide sequences of interest on yeast host cells, comprising:
   a) introducing at least one expression vector comprising an expression cassette encoding a polypeptide of interest fused in frame to a first adapter sequence, into yeast host cells
   b) introducing a helper vector encoding a fusion protein consisting of a second adapter sequence fused to an outer surface anchoring protein expressed by the host cells of (a), and
   c) maintaining the host cells under suitable conditions for expression of the proteins encoded by the expression cassette and helper vector wherein the polypeptides of interest are displayed on the surface of the yeast host cell wherein the expression vector is selected from pMAT9, and pMAT12, and the helper vector is selected from pMAT7, and pMAT8.

2. The method of claim 1 wherein the repertoire of polypeptide sequences of interest is an antibody scFv library.

3. The method of claim 1 wherein the yeast cells are selected from a group consisting of *S. cerevisiae, P. pichia, H. polymorpha*, and *C. albicans*.

4. The method of claim 1 wherein the yeast outer surface anchoring sequences are selected from the group consisting of Aga1 and Aga2, Cwp1, Cwp2, Gaslp, Yap3p, Flo1p, Crh2p, Pir1, Pir2, Pir4, Icwp in *S. cerevisiae*; HpSEDI, HpGASI, HpTIPI, HPWPI in *H. polymorpha*, and Hwp1p, Als3p, Rbt5p in *C. albicans*.

5. The method of claim 1 wherein the first adapter and second adapter are homodimer sequences.

6. The method of claim 1 wherein the first adapter sequence consists of SEQ ID NO:1 and the second adapter sequence consists of SEQ ID NO: 2.

* * * * *